(12) United States Patent
Goosens

(10) Patent No.: US 10,317,418 B2
(45) Date of Patent: *Jun. 11, 2019

(54) USE OF GHRELIN OR FUNCTIONAL GHRELIN RECEPTOR AGONISTS TO PREVENT AND TREAT STRESS-SENSITIVE PSYCHIATRIC ILLNESS

(71) Applicant: Massachusetts Institute of Technology, Cambridge, MA (US)

(72) Inventor: Ki Ann Goosens, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/052,110

(22) Filed: Feb. 24, 2016

(65) Prior Publication Data

US 2016/0243197 A1   Aug. 25, 2016

Related U.S. Application Data

(60) Provisional application No. 62/119,898, filed on Feb. 24, 2015.

(51) Int. Cl.

| | | |
|---|---|---|
| A01N 57/00 | (2006.01) |
| A61K 31/66 | (2006.01) |
| A61K 39/00 | (2006.01) |
| C12N 15/113 | (2010.01) |
| G01N 33/74 | (2006.01) |
| A61K 31/165 | (2006.01) |
| A61K 31/395 | (2006.01) |
| A61K 31/40 | (2006.01) |
| A61K 31/404 | (2006.01) |
| A61K 31/415 | (2006.01) |
| A61K 31/4439 | (2006.01) |
| A61K 31/4545 | (2006.01) |
| A61K 31/7076 | (2006.01) |
| A61K 38/25 | (2006.01) |

(52) U.S. Cl.
CPC .......... *G01N 33/74* (2013.01); *A61K 31/165* (2013.01); *A61K 31/395* (2013.01); *A61K 31/40* (2013.01); *A61K 31/404* (2013.01); *A61K 31/415* (2013.01); *A61K 31/4439* (2013.01); *A61K 31/4545* (2013.01); *A61K 31/7076* (2013.01); *A61K 38/25* (2013.01); *G01N 2800/30* (2013.01); *G01N 2800/54* (2013.01)

(58) Field of Classification Search
None
See application file for complete search history.

(56) References Cited

U.S. PATENT DOCUMENTS

| | | |
|---|---|---|
| 4,857,637 A | 8/1989 | Hammonds et al. |
| 4,997,815 A | 3/1991 | Perrine et al. |
| 7,479,271 B2 | 1/2009 | Marquis et al. |
| 7,632,809 B2 | 12/2009 | Chen |
| 7,666,833 B2 | 2/2010 | Ghigo et al. |
| 7,901,679 B2 | 3/2011 | Marquis et al. |
| 8,013,015 B2 | 9/2011 | Harran et al. |
| 8,293,709 B2 | 10/2012 | Ross et al. |
| 9,724,396 B2 * | 8/2017 | Goosens ............... A61K 38/27 |
| 9,821,042 B2 * | 11/2017 | Goosens ............ A61K 39/0005 |
| 10,039,813 B2 | 8/2018 | Goosens |
| 2002/0187938 A1 | 12/2002 | Deghenghi |
| 2003/0032636 A1 | 2/2003 | Cremers et al. |
| 2004/0033948 A1 | 2/2004 | Chen |
| 2005/0070712 A1 | 3/2005 | Kosogof et al. |
| 2005/0148515 A1 | 7/2005 | Dong |
| 2005/0187237 A1 | 8/2005 | Distefano et al. |
| 2005/0191317 A1 | 9/2005 | Bachmann et al. |
| 2005/0201938 A1 | 9/2005 | Bryant et al. |
| 2005/0257279 A1 | 11/2005 | Qian et al. |
| 2006/0025344 A1 | 2/2006 | Lange et al. |
| 2006/0025566 A1 | 2/2006 | Hoveyda et al. |
| 2006/0293370 A1 | 12/2006 | Saunders et al. |
| 2007/0021331 A1 | 1/2007 | Fraser et al. |
| 2007/0025991 A1 | 2/2007 | Pothoulakis et al. |
| 2007/0037857 A1 | 2/2007 | Perrissoud et al. |
| 2007/0191283 A1 | 8/2007 | Polvino |
| 2007/0237775 A1 | 10/2007 | Kikly et al. |
| 2007/0275877 A1 | 11/2007 | Baron et al. |
| 2008/0058405 A1 | 3/2008 | Lewy |
| 2008/0119540 A1 | 5/2008 | Thompson |
| 2008/0242619 A1 | 10/2008 | Dong |
| 2008/0261873 A1 | 10/2008 | Geesaman |
| 2008/0262042 A1 | 10/2008 | Kajino et al. |
| 2008/0300194 A1 | 12/2008 | Mann et al. |
| 2009/0069245 A1 | 3/2009 | Bowers et al. |

(Continued)

FOREIGN PATENT DOCUMENTS

| | | |
|---|---|---|
| WO | WO 1993/018761 A1 | 9/1993 |
| WO | WO 1997/011178 A1 | 3/1997 |

(Continued)

OTHER PUBLICATIONS

Yamada et al., Int. Rev. Neurobiol., 2014, 119:373-93.*
Carvajal et al., Central ghrelin increases anxiety in the Open Field test and impairs retention memory in a passive avoidance task in neonatal chicks. Neurobiol Learn Mem. May 2009;91(4):402-7. doi: 10.1016/j.nlm.2008.12.008. Epub Jan. 31, 2009.
Lutter et al., The orexigenic hormone ghrelin defends against depressive symptoms of chronic stress. Nat Neurosci. Jul. 2008;11(7):752-3. doi: 10.1038/nn.2139. Epub Jun. 15, 2008.
Meyer et al., A ghrelin-growth hormone axis drives stress-induced vulnerability to enhanced fear. Mol Psychiatry. Dec. 2014;19(12):1284-94. doi: 10.1038/mp.2013.135. Epub Oct. 15, 2013.

(Continued)

*Primary Examiner* — Olga N Chernyshev
(74) *Attorney, Agent, or Firm* — Wolf, Greenfield & Sacks, P.C.

(57) ABSTRACT

The invention relates to methods of treating stress-sensitive psychiatric diseases arising from trauma in a subject by enhancing ghrelin signaling in the BLA of the subject. The invention also relates to methods of reversing ghrelin resistance.

39 Claims, 18 Drawing Sheets

(56) References Cited

U.S. PATENT DOCUMENTS

| | | |
|---|---|---|
| 2009/0131478 A1 | 5/2009 | Dong et al. |
| 2009/0143310 A1 | 6/2009 | Polvino et al. |
| 2009/0149512 A1 | 6/2009 | Raun et al. |
| 2009/0156483 A1 | 6/2009 | Dong et al. |
| 2009/0156642 A1 | 6/2009 | Nishida et al. |
| 2009/0163416 A1 | 6/2009 | Tulipano et al. |
| 2009/0253673 A1 | 10/2009 | Ge et al. |
| 2009/0275511 A1 | 11/2009 | Dong |
| 2009/0275648 A1 | 11/2009 | Fraser et al. |
| 2010/0021487 A1 | 1/2010 | Zorrilla et al. |
| 2010/0086955 A1 | 4/2010 | Harran et al. |
| 2010/0196330 A1 | 8/2010 | Ghigo et al. |
| 2010/0196396 A1 | 8/2010 | Szentirmai et al. |
| 2010/0227806 A1 | 9/2010 | Giovanni |
| 2010/0254994 A1 | 10/2010 | Raso |
| 2010/0272734 A1 | 10/2010 | Berger et al. |
| 2010/0286152 A1 | 11/2010 | Bernasconi et al. |
| 2011/0021420 A1 | 1/2011 | Bloom et al. |
| 2011/0245160 A1 | 10/2011 | Van Der Lely |
| 2011/0245161 A1 | 10/2011 | Mintz |
| 2011/0257086 A1 | 10/2011 | Cole et al. |
| 2011/0269777 A1 | 11/2011 | Bachurin et al. |
| 2011/0318807 A1 | 12/2011 | Harran et al. |
| 2012/0095070 A1 | 4/2012 | Springer et al. |
| 2012/0129767 A1 | 5/2012 | Tulipano et al. |
| 2012/0232113 A1 | 9/2012 | Mann et al. |
| 2012/0237521 A1 | 9/2012 | Berger et al. |
| 2013/0123170 A1 | 5/2013 | Dong |
| 2013/0289068 A1 | 10/2013 | Polvino |
| 2013/0344091 A1 | 12/2013 | Berger et al. |
| 2014/0031393 A1 | 1/2014 | Nishida et al. |
| 2014/0088139 A1 | 3/2014 | Zollers et al. |
| 2014/0274900 A1 | 9/2014 | Goosens |
| 2014/0287997 A1 | 9/2014 | Goosens |
| 2014/0328848 A1 | 11/2014 | Feige et al. |
| 2015/0031615 A1 | 1/2015 | Dong |
| 2015/0297691 A1 | 10/2015 | Goosens |
| 2016/0058851 A1 | 3/2016 | Goosens |
| 2016/0106821 A1 | 4/2016 | Goosens |
| 2017/0007618 A1 | 1/2017 | Goosens et al. |

FOREIGN PATENT DOCUMENTS

| | | |
|---|---|---|
| WO | WO 1997/041878 A1 | 11/1997 |
| WO | WO 2001/000676 A1 | 1/2001 |
| WO | WO 2003/092725 A1 | 11/2003 |
| WO | WO 2004/021984 A2 | 3/2004 |
| WO | WO 2005/097830 A2 | 10/2005 |
| WO | WO 2005/112903 A2 | 12/2005 |
| WO | WO 2006/019577 A1 | 2/2006 |
| WO | WO 2008/004972 A2 | 1/2008 |
| WO | WO 2010/051447 A1 | 5/2010 |
| WO | WO 2010/132580 A2 | 11/2010 |
| WO | WO 2011/053821 A1 | 5/2011 |
| WO | WO 2013/119800 A1 | 8/2013 |
| WO | WO 2013/155504 A1 | 10/2013 |
| WO | WO 2014/027899 A1 | 2/2014 |

OTHER PUBLICATIONS

Spencer et al., Ghrelin regulates the hypothalamic-pituitary-adrenal axis and restricts anxiety after acute stress. Biol Psychiatry. Sep. 15, 2012;72(6):457-65. doi: 10.1016/j.biopsych.2012.03.010. Epub Apr. 21, 2012.

Albarran-Zeckler et al., Growth hormone secretagogue receptor (GHS-R1a) knockout mice exhibit improved spatial memory and deficits in contextual memory. Behav Brain Res. Jun. 15 2012;232(1):13-9. doi:10.1016/j.bbr.2012.03.012. Epub Mar. 31, 2012.

Alvarez-Crespo et al., The amygdala as a neurobiological target for ghrelin in rats: neuroanatomical, electrophysiological and behavioral evidence. PLoS One. 2012;7(10):e46321. doi: 10.1371/journal.pone.0046321. Epub Oct. 10, 2012.

Anagnostaras et al., Hippocampus and contextual fear conditioning: recent controversies and advances. Hippocampus. 2001;11(1):8-17.

Andero et al., Amygdala-dependent fear is regulated by Oprl1 in mice and humans with PTSD. Sci Transl Med. Jun. 5, 2013;5(188):188ra73. doi: 10.1126/scitranslmed.3005656.

Arafat et al., Glucagon inhibits ghrelin secretion in humans. Eur J Endocrinol. Sep. 2005;153(3):397-402.

Banasch et al., Glucagon-like peptide 2 inhibits ghrelin secretion in humans. Regul Pept. Dec. 10, 2006;137(3):173-8. Epub Aug. 22, 2006.

Bangasser et al., The hippocampus is necessary for enhancements and impairments of learning following stress. Nat Neurosci. Nov. 2007;10(11):1401-3. Epub Sep. 30, 2007.

Banks et al., Extent and direction of ghrelin transport across the blood-brain barrier is determined by its unique primary structure. J Pharmacol Exp Ther. Aug. 2002;302(2):822-7.

Bednarek et al., Structure-function studies on the new growth hormone-releasing peptide, ghrelin: minimal sequence of ghrelin necessary for activation of growth hormone secretagogue receptor 1a. J Med Chem. Nov. 16, 2000;43(23):4370-6.

Belanoff et al., Cortisol activity and cognitive changes in psychotic major depression. Am J Psychiatry. Oct. 2001;158(10):1612-6.

Bernstein et al., Symptom features of postpartum depression: are they distinct? Depress Anxiety. 2008;25(1):20-6.

Betley et al., Neurons for hunger and thirst transmit a negative-valence teaching signal. Nature. May 14, 2015;521(7551):180-5. doi: 10.1038/nature14416. Epub Apr. 27, 2025.

Birzniece et al., Growth hormone receptor modulators. Rev Endocr Metab Disord. Jun. 2009;10(2):145-56. doi: 10.1007/s11154-008-9089-x.

Bloch et al., Effects of gonadal steroids in women with a history of postpartum depression. Am J Psychiatry. Jun. 2000;157(6):924-30.

Bloch et al., Endocrine factors in the etiology of postpartum depression. Compr Psychiatry. May-Jun. 2003;44(3):234-46.

Bramham et al., BDNF function in adult synaptic plasticity: the synaptic consolidation hypothesis. Prog Neurobiol. Jun. 2005;76(2):99-125.

Briggs et al., Evidence that diet-induced hyperleptinemia, but not hypothalamic gliosis, causes ghrelin resistance in NPY/AgRP neurons of male mice. Endocrinology. Jul. 2014;155(7):2411-22. doi:10.1210/en.2013-1861. Epub Apr. 17, 2014.

Brioni et al., Involvement of the amygdala GABAergic system in the modulation of memory storage. Brain Res. May 15, 1989;487(1):105-12.

Cahill et al., Amygdala activity at encoding correlated with long-term, free recall of emotional information. Proc Natl Acad Sci U S A. Jul. 23, 1996;93(15):8016-21.

Carlini et al., Differential role of the hippocampus, amygdala, and dorsal raphe nucleus in regulating feeding, memory, and anxiety-like behavioral responses to ghrelin. Biochem Biophys Res Commun. Jan. 16, 2004;313(3):635-41.

Carlini et al., Ghrelin increases anxiety-like behavior and memory retention in rats. Biochem Biophys Res Commun. Dec. 20, 2002;299(5):739-43.

Castellano et al., Interaction of beta-endorphin and GABAergic drugs in the regulation of memory storage. Behav Neural Biol. Sep. 1993;60(2):123-8.

Chaplin et al., Improvements in behaviour and self-esteem following growth hormone treatment in short prepubertal children. Horm Res Paediatr. 2011;75(4):291-303. doi: 10.1159/000322937. Epub Feb. 5, 2011.

Chen et al., Rapid loss of dendritic spines after stress involves derangement of spine dynamics by corticotropin-releasing hormone. J Neurosci. Mar. 12, 2008;28(11):2903-11. doi: 10.1523/JNEUROSCI.0225-08.2008.

Clark et al., Long-acting growth hormones produced by conjugation with polyethylene glycol. J Biol Chem. Sep. 6, 1996;271(36):21969-77.

Codner et al., Effects of oral administration of ibutamoren mesylate, a nonpeptide growth hormone secretagogue, on the growth hormone-insulin-like growth factor I axis in growth hormone-deficient children. Clin Pharmacol Ther. Jul. 2001;70(1):91-8.

(56) References Cited

OTHER PUBLICATIONS

Conrad, A critical review of chronic stress effects on spatial learning and memory. Prog Neuropsychopharmacol Biol Psychiatry. Jun. 30, 2010;34(5):742-55. doi:10.1016/j.pnpbp.2009.11.003. Epub Nov. 10, 2009.

Cook et al., The pharmacokinetic and pharmacodynamic characteristics of a long-acting growth hormone (GH) preparation (nutropin depot) in GH-deficient adults. J Clin Endocrinol Metab. Oct. 2002;87(10):4508-14.

Cordero et al., A role for brain glucocorticoid receptors in contextual fear conditioning: dependence upon training intensity. Brain Res. Mar. 9, 1998;786(1-2):11-7.

Cowley et al., The distribution and mechanism of action of ghrelin in the CNS demonstrates a novel hypothalamic circuit regulating energy homeostasis. Neuron. Feb. 20, 2003;37(4):649-61.

Cummings et al., A preprandial rise in plasma ghrelin levels suggests a role in meal initiation in humans. Diabetes. Aug. 2001;50(8):1714-9.

Davies et al., Origins and evolution of antibiotic resistance. Microbiol Mol Biol Rev. Sep. 2010;74(3):417-33. doi: 10.1128/MMBR.00016-10.

De Quervain et al., Stress and glucocorticoids impair retrieval of long-term spatial memory. Nature. Aug. 20, 1998;394(6695):787-90.

De Vriese et al., Ghrelin degradation by serum and tissue homogenates: identification of the cleavage sites. Endocrinology. Nov. 2004;145(11):4997-5005. Epub Jul. 15, 2004.

Diano et al., Ghrelin controls hippocampal spine synapse density and memory performance. Nat Neurosci. Mar. 2006;9(3):381-8. Epub Feb. 19, 2006.

Dienes et al., The stress sensitization hypothesis: understanding the course of bipolar disorder. J Affect Disord. Oct. 2006;95(1-3):43-9. Epub Jul. 11, 2006.

Dietrich et al., Hypothalamic Agrp neurons drive stereotypic behaviors beyond feeding. Cell. Mar. 12, 2015;160(6):1222-32. doi:10.1016/j.cell.2015.02.024. Epub Mar. 5, 2015.

Dogrukol-AK et al., Isolation of peptide transport system-6 from brain endothelial cells: therapeutic effects with antisense inhibition in Alzheimer and stroke models. J Cereb Blood Flow Metab. Feb. 2009;29(2):411-22. doi: 10.1038/jcbfm.2008.131. Epub Nov. 12, 2008.

Donahue et al., Growth hormone is produced within the hippocampus where it responds to age, sex, and stress. Proc Natl Acad Sci U S A. Apr. 11, 2006;103(15):6031-6. Epub Mar 30, 2006.

Donahue et al., Transcriptional profiling reveals regulated genes in the hippocampus during memory formation. Hippocampus. 2002;12(6):821-33.

Dudai, The neurobiology of consolidations, or, how stable is the engram? Annu Rev Psychol. 2004;55:51-86.

Ellicott et al., Life events and the course of bipolar disorder. Am J Psychiatry. Sep. 1990;147(9):1194-8.

Finsterwald et al., Stress and glucocorticoid receptor-dependent mechanisms in long-term memory: from adaptive responses to psychopathologies. Neurobiol Learn Mem. Jul. 2014;112:17-29. doi: 10.1016/j.nlm.2013.09.017. Epub Oct. 7, 2013.

Fleshner et al., The neurobiology of the stress-resistant brain. Stress. Sep. 2011;14(5):498-502. doi: 10.3109/10253890.2011.596865. Epub Jul. 26, 2011.

Foust et al., Intravascular AAV9 preferentially targets neonatal neurons and adult astrocytes. Nat Biotechnol. Jan. 2009;27(1):59-65. doi: 10.1038/nbt.1515. Epub Dec. 21, 2008.

Fumoto et al., Targeted Gene Delivery. Importance of Administration Routes. Intech. 2013;3-31.

Garin et al., Clinical review: The human experience with ghrelin administration. J Clin Endocrinol Metab. May 2013;98(5):1826-37. doi: 10.1210/jc.2012-4247. Epub Mar. 26, 2013.

Ghersi et al., Ghrelin increases memory consolidation through hippocampal mechanisms dependent on glutamate release and NR2B-subunits of the NMDA receptor. Psychopharmacology (Berl). May 2015;232(10):1843-57. doi:10.1007/s00213-014-3817-6. Epub Dec. 4, 2014.

Gold et al., Organization of the stress system and its dysregulation in melancholic and atypical depression: high vs low CRH/NE states. Mal Psychiatry. 2002;7(3):254-75.

Goldstone et al., Ghrelin mimics fasting to enhance human hedonic, orbitofrontal cortex, and hippocampal responses to food. Am J Clin Nutr. Jun. 2014;99(6):1319-30. doi: 10.3945/ajcn.113.075291. Epub Apr. 23, 2014.

Goosens, Hippocampal regulation of aversive memories. Curr Opin Neurobiol. Jun. 2011;21(3):460-6. doi: 10.1016/j.conb.2011.04.003. Epub May 3, 2011.

Graham et al., Recombinant human growth hormone in abstinent androgenic-anabolic steroid use: psychological, endocrine and trophic factor effects. Curr Neurovasc Res. Feb. 2007;4(1):9-18.

Guan et al., Distribution of mRNA encoding the growth hormone secretagogue receptor in brain and peripheral tissues. Brain Res Mol Brain Res. Aug. 1997;48(1):23-9.

Guardiola-Lemaitre et al., Agomelatine: mechanism of action and pharmacological profile in relation to antidepressant properties. Br J Pharmacal. Aug. 2014;171(15):3604-19. doi:10.1111/bph.12720.

Hagemann et al., Glucagon-like peptide 1 (GLP-1) suppresses ghrelin levels in humans via increased insulin secretion. Regul Pept. Oct. 4, 2007;143(1-3):64-8. Epub Mar. 20, 2007.

Hansson et al., Influence of ghrelin on the central serotonergic signaling system in mice. Neuropharmacology. Apr. 2014;79:498-505. doi: 10.1016/j.neuropharm.2013.12.012 1 page.

Harrison et al., Exploring the Structure of Human Defensive Responses from Judgments of Threat Scenarios. PLoS One. Aug. 21, 2015;10(8):e0133682. doi: 10.1371/journal.pone.0133682. eCollection 2015.

Holbrook et al., Morphine use after combat injury in Iraq and past-traumatic stress disorder. N Engl J Med. Jan 14, 2010;362(2):110-7. doi: 10.1056/NEJMoa0903326.

Huang et al., Efficient gene delivery targeted to the brain using a transferrin-conjugated polyethyleneglycol-modified polyamidoamine dendrimer. FASEB J. Apr. 2007;21(4):1117-25. Epub Jan. 11, 2007.

Hui et al., Memory enhancement of classical fear conditioning by post-training injections of corticosterone in rats. Neurobiol Learn Mem. Jan. 2004;81(1):67-74.

Jacks et al., MK-0677, a potent, novel, orally active growth hormone (GH) secretagogue: GH, insulin-like growth factor I, and other hormonal responses in beagles. Endocrinology. Dec. 1996;137(12):5284-9.

Jasnow et al., Thy1-expressing neurons in the basolateral amygdala may mediate fear inhibition. J Neurosci. Jun. 19, 2013;33(25):10396-404. doi:10.1523/JNeurosci.5539-12.2013.

Jeneson et al., Working memory, long-term memory, and medial temporal lobe function. Learn Mem. Dec. 16, 2011;19(1):15-25. doi: 10.1101/lm.024018.111. Print Jan. 2012.

Jostel et al., A new sustained-release preparation of human growth hormone and its pharmacokinetic, pharmacodynamic and safety profile. Clin Endocrinol (Oxf). May 2005;62(5):623-7.

Juster et al., A transdisciplinary perspective of chronic stress in relation to psychopathology throughout life span development. Dev Psychopathol. Aug. 2011;23(3):725-76. doi: 10.1017/S0954579411000289.

Kaufer et al., Restructuring the neuronal stress response with anti-glucocorticoid gene delivery. Nat Neurosci. Sep. 2004;7(9):947-53. Epub Aug. 8, 2004.

Kearns et al., Early interventions for PTSD: a review. Depress Anxiety. Oct. 2012;29(10):833-42. doi: 10.1002/da.21997. Epub Aug. 31, 2012.

Kojima et al., Ghrelin is a growth-hormone-releasing acylated peptide from stomach. Nature. Dec. 9, 1999;402(6762):656-60.

Krishnan et al. Animal models of depression: molecular perspectives. Curr Top Behav Neurosci. 2011;7:121-47. doi: 10.1007/7854_2010_108.

Krishnan et al., Linking molecules to mood: new insight into the biology of depression. Am J Psychiatry. Nov. 2010;167(11):1305-20. doi:10.1176/appi.ajp.2009.10030434. Epub Sep. 15, 2010.

(56) References Cited

OTHER PUBLICATIONS

Kumar et al., Differential effects of chronic social stress and fluoxetine on meal patterns in mice. Appetite. May 2013;64:81-8. doi:10.1016/j.appet.2012.12.023. Epub Jan. 11, 2013.

Lakshminarasimhan et al., Stress leads to contrasting effects on the levels of brain derived neurotrophic factor in the hippocampus and amygdala. PloS One. 2012;7(1):e30481. doi: 10.1371/journal.pone.0030481. Epub Jan. 17, 2012.

Le Grevès et al., Growth hormone induces age-dependent alteration in the expression of hippocampal growth hormone receptor and N-methyl-D-aspartate receptor subunits gene transcripts in male rats. Proc Natl Acad Sci U S A. May 14, 2002;99(10):7119-23.

Lederbogen et al., City living and urban upbringing affect neural social stress processing in humans. Nature. Jun. 22, 2011;474(7352):498-501. doi: 10.1038/nature10190.

Lee et al., Sampling blood from the lateral tail vein of the rat. J Vis Exp. May 18, 2015;(99):e52766. doi: 10.3791/52766.

Liu et al., Brain-targeting gene delivery and cellular internalization mechanisms for modified rabies virus glycoprotein RVG29 nanoparticles. Biomaterials. Sep. 2009;30(25):4195-202. doi:10.1016/j.biomaterials.2009.02.051. Epub May 20, 2009.

Lockie et al., Diet-induced obesity causes ghrelin resistance in reward processing tasks. Psychoneuroendocrinology. Dec. 2015;62:114-20. doi: 10.1016/j.psyneuen.2015.08.004. Epub Aug. 11, 2015.

Magariños et al., Stress-induced atrophy of apical dendrites of hippocampal CA3c neurons: involvement of glucocorticoid secretion and excitatory amino acid receptors. Neuroscience. Nov. 1995;69(1):89-98.

Mahajan et al., Atypical depression in growth hormone deficient adults, and the beneficial effects of growth hormone treatment on depression and quality of life. Eur J Endocrinol. Sep. 2004;151(3):325-32.

Mahmoud et al., Growth hormone enhances excitatory synaptic transmission in area CA1 of rat hippocampus. J Neurophysiol. May 2006;95(5):2962-74. Epub Feb. 15, 2006.

Makatsori et al., Modulation of neuroendocrine response and nonverbal behavior during psychosocial stress in healthy volunteers by the glutamate release-inhibiting drug lamotrigine. Neuroendocrinology. Jan. 2004;79(1):34-42.

Mancuso et al., Paradoxical reactions to benzodiazepines: literature review and treatment options. Pharmacotherapy. Sep. 2004;24(9):1177-85.

Maric et al., Psychiatric and neuropsychological changes in growth hormone-deficient patients after traumatic brain injury in response to growth hormone therapy. J Endocrinol Invest. Dec. 2010;33(11):770-5. doi: 10.3275/7045. Epub May 17, 2010.

Marin et al., Metyrapone administration reduces the strength of an emotional memory trace in a long-lasting manner. J Clin Endocrinol Metab. Aug. 2011;96(8):E1221-7. doi: 10.1210/jc.2011-0226. Epub May 18, 2011.

Mayorov et al., Catalytic antibody degradation of ghrelin increases whole-body metabolic rate and reduces refeeding in fasting mice. Proc Natl Acad Sci U S A. Nov. 11, 2008;105(45):17487-92. doi: 10.1073/pnas.0711808105. Epub Nov. 3, 2008.

McEwen, Protective and damaging effects of stress mediators. N. Engl J Med. Jan. 15, 1998;338(3):171-9.

McIntyre et al., Amygdala norepinephrine levels after training predict inhibitory avoidance retention performance in rats. Eur J Neurosci. Oct. 2002;16(7):1223-6.

Meyer et al., Chronic ghrelin receptor activation enhances Pavlovian fear learning without increasing anxiety. Society for Neuroscience Abstract Viewer and Itinerary Planner. 2009;39.

Meyer et al., Poster B7: Ghrelin signaling modulates amygdala-dependent Learning. The Neuroscience of Emotion: From Reaction to Regulation. Jun. 4, 2009.

Miller et al., If it goes up, must it come down? Chronic stress and the hypothalamic-pituitary-adrenocortical axis in humans. Psychol Bull. Jan. 2007;133(1):25-45.

Molina et al., Growth hormone modulates hippocampal excitatory synaptic transmission and plasticity in old rats. Neurobiol Aging. Sep. 2012;33(9):1938-49. doi: 10.1016rj.neurobiolaging.2011.09.014. Epub Oct. 19, 2011.

Nass et al., Effects of an oral ghrelin mimetic on body composition and clinical outcomes in healthy older adults: a randomized trial. Ann Intern Med. Nov. 4, 2008;149(9):601-11.

Natalucci et al., Spontaneous 24-h ghrelin secretion pattern in fasting subjects: maintenance of a meal-related pattern. Eur J Endocrinol. Jun. 2005;152(6):845-50.

Nyberg et al., Growth hormone and its receptors in the central nervous system—location and functional significance. Horm Res. 1996;45(1-2):18-22.

Ohara et al., Rates and risk of postpartum depression—a meta-analysis. Int Rev Psych. 1996;8(1):37-54.

Pacold et al., Biologically active pituitary hormones in the rat brain amygdaloid nucleus. Science. Feb. 17, 1978;199(4330):804-6.

Pardridge, Drug transport across the blood-brain barrier. J Cereb Blood Flow Metab. Nov. 2012;32(11):1959-72. doi: 10.1038/jcbfm.2012.126. Epub Aug. 29, 2012.

Pardridge, The blood-brain barrier: bottleneck in brain drug development. NeuroRx. Jan. 2005;2(1):3-14.

Parsons et al., Implications of memory modulation for post-traumatic stress and fear disorders. Nat Neurosci. Feb. 2013;16(2):146-53. doi:10.1038/nn.3296. Epub Jan. 28, 2013.

Ransome et al., Growth hormone signaling and hippocampal neurogenesis: insights from genetic models. Hippocampus. 2008;18(10):1034-50. doi: 10.1002/hipo.20463.

Raybuck et al., Double dissociation of amygdala and hippocampal contributions to trace and delay fear conditioning. PLoS One. Jan. 19, 2011;6(1):e15982. doi: 10.1371/journal.pone.0015982.

Reiter et al., A multicenter study of the efficacy and safety of sustained release GH in the treatment of naive pediatric patients with GH deficiency. J Clin Endocrinol Metab. Oct. 2001;86(10):4700-6.

Ribeiro et al., Ghrelin triggers the synaptic incorporation of AMPA receptors in the hippocampus. Proc Natl Acad Sci U S A. Jan. 7, 2014;111(1):E149-58. doi:10.1073/pnas.1313798111. Epub Dec. 23. 2013.

Rivera et al., Long-term regulated expression of growth hormone in mice after intramuscular gene transfer. Proc Natl Acad Sci U S A. Jul. 20, 1999;96(15):8657-62.

Robertson et al., Antenatal risk factors for postpartum depression: a synthesis of recent literature. Gen Hasp Psychiatry. Jul.-Aug. 2004;26(4):289-95.

Santarelli et al., Requirement of hippocampal neurogenesis for the behavioral effects of antidepressants. Science. Aug. 8, 2003;301(5634):805-9.

Schellekens et al., Promiscuous dimerization of the growth hormone secretagogue receptor (GHS-R1a) attenuates ghrelin-mediated signaling. J Biol Chem. Jan. 4, 2013;288(1):181-91. doi: 10.1074/jbc.M112.382473.

Schellekens et al., Taking two to tango: a role for ghrelin receptor heterodimerization in stress and reward. Front Neurosci. Aug. 30, 2013;7:148. doi: 10.3389/fnins.2013.00148.

Shanks et al., Are animal models predictive for humans? Philos Ethics Humanit Med. Jan. 15, 2009;4:2. doi: 10.1186/1747-5341-4-2.

Shors et al., Sex differences and opposite effects of stress on dendritic spine density in the male versus female hippocampus. J Neurosci. Aug. 15, 2001;21(16):6292-7.

Siegrist, Chronic psychosocial stress at work and risk of depression:evidence from prospective studies. Eur Arch Psychiatry Clin Neurosci. Nov. 2008;258 Suppl 5:115-9. doi: 10.1007/s00406-008-5024-0.

Sivertsen et al., Functionally biased signaling properties of 7TM receptors—opportunities for drug development for the ghrelin receptor. Br J Pharmacol. Dec. 2013;170(7):1349-62. doi: 10.1111/bph.12361.

Song et al., Ghrelin modulates lateral amygdala neuronal firing and blocks acquisition for conditioned taste aversion. PLoS One. Jun. 7, 2013;8(6):e65422. doi:10.1371/journal.pone.0065422. Print 2013.

(56) References Cited

OTHER PUBLICATIONS

Spencer et al., Ghrelin's Role in the Hypothalamic-Pituitary-Adrenal Axis Stress Response: Implications for Mood Disorders. Biol Psychiatry. Jul. 1, 2015;78(1):19-27. doi:10.1016/j.biopsych.2014.10.021. Epub Oct. 31, 2014.
Sun et al., Local expression of GH and IGF-1 in the hippocampus of GH-deficient long-lived mice. Neurobiol Aging. Jun. 2005;26(6):929-37.
Telegdy et al., Neurotransmitter-mediated action of an antagonist of growth hormone-releasing hormone on anxiolysis in mice. Behav Brain Res. Jul. 15, 2012;233(1):232-6. doi: 10.1016/j.bbr.2012.04.011. Epub May 5, 2012.
Tibshirani, Regression shrinkage and selection via the lasso. J R Stat Soc: Ser B (Method) 1996;58(1):267-288.
Tolle et al., Ultradian rhythmicity of ghrelin secretion in relation with GH, feeding behavior, and sleep-wake patterns in rats. Endocrinology. Apr. 2002;143(4):1353-61.
Treacy et al., Functional glucocorticoid inducible enhancer activity in the 5'-flanking sequences of the rat growth hormone gene. J Steroid Biochem Mol Biol. Jan. 1991;38(1):1-15.
Tronson et al., Molecular mechanisms of memory reconsolidation. Nat Rev Neurosci. Apr. 2007;8(4):262-75.
Tschop et al., Ghrelin induces adiposity in rodents. Nature. Oct. 19, 2000;407(6806):908-13.
Tsigos et al., Hypothalamic-pituitary-adrenal axis, neuroendocrine factors and stress. J Psychosom Res. Oct. 2002;53(4):865-71.
Vaiva et al., Low posttrauma GABA plasma levels as a predictive factor in the development of acute posttraumatic stress disorder. Biol Psychiatry. Feb. 1, 2004;55(3):250-4.
Valvassori et al., Contributions of animal models to the study of mood disorders. Rev Bras Psiquiatr. 2013;35 Suppl 2:S121-31. doi:10.1590/1516-4446-2013-1168.
Vander Weele et al., Restoration of hippocampal growth hormone reverses stress-induced hippocampal impairment. Front Behav Neurosci. Jun. 14, 2013;7:66. doi: 10.3389/fnbeh.2013.00066. eCollection 2013.
Varga et al., Synthesis and biological evaluation of antagonists of growth hormone-releasing hormone with high and protracted in vivo activities. Proc Natl Acad Sci U S A. Jan. 19, 1999;96(2):692-7.
Vyas et al., Chronic stress induces contrasting patterns of dendritic remodeling in hippocampal and amygdaloid neurons. J Neurosci. Aug. 1, 2002;22(15):6810-8.
Wanisch et al., Tackling obstacles for gene therapy targeting neurons: disrupting perineural nets with hyaluronidase improves transduction. PLoS One. 2013;8(1):e53269. doi: 10.1371/journal.pone.0053269. Epub Jan. 3, 2013.
Warner-Schmidt et al., Hippocampal neurogenesis: opposing effects of stress and antidepressant treatment. Hippocampus. 2006;16(3):239-49.
Wilensky et al., Functional inactivation of the amygdala before but not after auditory fear conditioning prevents memory formation. J Neurosci. Dec. 15, 1999;19(24):RC48.
Wren et al., Ghrelin enhances appetite and increases food intake in humans. J Clin Endocrinol Metab. Dec. 2001;86(12):5992.

Xin et al., Discovery and pharmacological evaluation of growth hormone secretagogue receptor antagonists. J Med Chem. Jul. 27, 2006;49(15):4459-69.
Yao et al., Unexpected Reaction Pathway for butyrylcholinesterase-catalyzed inactivation of "hunger hormone" ghrelin. Sci Rep. Feb. 29, 2016;6:22322. doi: 10.1038/srep22322.
Zarouna et al., Mood disorders: A potential link between ghrelin and leptin on human body? World J Exp Med. May 20, 2015;5(2):103-9. doi: 10.5493/wjem.v5.i2.103. eCollection May 20, 2015.
Zearfoss et al., A molecular circuit composed of CPEB-1 and c-Jun controls growth hormone-mediated synaptic plasticity in the mouse hippocampus. J Neurosci. Aug. 20, 2008;28(34):8502-9. doi: 10.1523/JNEUROSCI.1756-08.2008.
Zhang et al., Drug delivery strategies to enhance the permeability of the blood-brain barrier for treatment of glioma. Drug Des Devel Ther. Apr. 9, 2015;9:2089-100. doi: 10.2147/DDDT.S79592. eCollection 2015.
Zhao et al., Ghrelin secretion stimulated by {beta}1-adrenergic receptors in cultured ghrelinoma cells and in fasted mice. Proc Natl Acad Sci U S A. Sep. 7, 2010;107(36):15868-73. doi: 10.1073/pnas.1011116107. Epub Aug. 16, 2010.
Bijanki et al., Hippocampal and left subcallosal anterior cingulate atrophy in psychotic depression. PLoS One. Oct. 22, 2014;9(10):e110770. doi: 10.1371/journal.pone.0110770. eCollection 2014.
Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.
Busatto, Structural and functional neuroimaging studies in major depressive disorder with psychotic features: a critical review. Schizophr Bull. Jul. 2013;39(4):776-86. doi: 10.1093/schbul/sbt054. Epub Apr. 24, 2013.
Deligiannidis et al., GABAergic neuroactive steroids and resting-state functional connectivity in postpartum depression: a preliminary study. J Psychiatr Res. Jun. 2013;47(6):816-28. doi:10.1016/j.jpsychires.2013.02.010. Epub Mar. 15, 2013.
Elvsashagen et al., Evidence for reduced dentate gyrus and fimbria volume in bipolar II disorder. Bipolar Disord. Mar. 2013;15(2):167-76. doi: 10.1111/bdi.12046. Epub Jan. 15, 2013.
Hoogenboom et al., Feasibility of studying brain morphology in major depressive disorder with structural magnetic resonance imaging and clinical data from the electronic medical record: a pilot study. Psychiatry Res. Mar. 30, 2013;211(3):202-13. doi:10.1016/j.pscychresns.2012.07.007. Epub Nov. 11, 2012.
Koresh et al., The long-term abnormalities in circadian expression of Period 1 and Period 2 genes in response to stress is normalized by agomelatine administered immediately after exposure. Eur Neuropsychopharmacol. Mar. 2012;22(3):205-21. doi:10.1016/j.euroneuro.2011.07.012. Epub Sep. 16, 2011.
Otto et al., De novo fear conditioning across diagnostic groups in the affective disorders: evidence for learning impairments. Behav Ther. Sep. 2014;45(5):619-29. doi:10.1016/j.beth.2013.12.012. Epub Jan. 5, 2014.
Palmerston Mendes et al., Dendrimers as Nanocarriers for Nucleic Acid and Drug Delivery in Cancer Therapy. Molecules. Aug. 23, 2017;22(9). pii: E1401. doi: 10.3390/molecules22091401.

* cited by examiner

USE OF GHRELIN OR FUNCTIONAL GHRELIN RECEPTOR AGONISTS TO PREVENT AND TREAT STRESS-SENSITIVE PSYCHIATRIC ILLNESS

RELATED APPLICATIONS

This application claims priority under 35 U.S.C. § 119(e) to U.S. Provisional Application Ser. No. 62/119,898, entitled "USE OF GHRELIN OR FUNCTIONAL GHRELIN RECEPTOR AGONISTS TO PREVENT AND TREAT STRESS-SENSITIVE PSYCHIATRIC ILLNESS" filed on Feb. 24, 2015, which is herein incorporated by reference in its entirety.

FEDERALLY SPONSORED RESEARCH

This invention was made with government support under Grant No. W911NF-10-1-0059 awarded by the U.S. Army Research Office and government support under Grant No. R01 MH084966 awarded by the National Institutes of Health. The government has certain rights in the invention.

BACKGROUND OF INVENTION

Ghrelin, often called "the hunger hormone", is an omnipresent circulating hormone that is released by the stomach and other peripheral organs into the bloodstream. In its acylated form (acyl-ghrelin), it can cross the blood-brain barrier and bind to central ghrelin receptors (growth hormone secretagogue receptor 1a, or GHSR). GHSRs are abundant in classic hypothalamic hunger regions. Also, ghrelin levels can be rapidly elevated within minutes during anticipatory hunger states. GHSRs are widely distributed throughout the brain including brain regions not typically associated with hunger, such as the basolateral complex of the amygdala (BLA), a brain region important for regulating fear. There are many contradictory findings on the role of the hormone ghrelin in aversive processing.

SUMMARY OF INVENTION

The present disclosure provides several surprising findings. For instance, in unstressed subjects, endogenous peripheral acyl-ghrelin robustly inhibits fear memory consolidation through actions in the amygdala. Higher levels of ghrelin after a traumatic exposure, as well as pharmacological agonism of the ghrelin receptor during the memory consolidation period following the traumatic exposure, decrease long-term fear memory strength. The invention is based, at least in part, on the surprising findings that a subject who has been exposed to trauma can be administered ghrelin or a functional ghrelin receptor agonist during the memory consolidation period or following re-activation of the memory (during reconsolidation) of a traumatic experience can reduce consolidation or reconsolidation of the memory, and reduce the impact of the trauma on stress-sensitive mental disorders. Further provided herein is the novel finding that chronic stress induces a persistent resistance to ghrelin, mediated by long-term downregulation of its receptor in the brain. Accordingly, the new link between stress, a novel type of metabolic ghrelin resistance, and vulnerability to excessive fear memory formation affords opportunity for formulating new therapeutics for stress-sensitive psychiatric disorders. Some aspects of the present disclosure provide methods of treating stress-sensitive psychiatric diseases arising from trauma exposure in a subject, including administering to the subject a therapeutically effective amount of ghrelin or an agent that enhances ghrelin signaling in the basolateral complex of the amygdala (BLA), within a memory consolidation period following the trauma exposure.

In some embodiments, the memory consolidation period is 0 hours-1 week, 0 hours-5 days, 0 hours-48 hours, or 0-24 hours following the trauma exposure. In some embodiments the memory consolidation period is 0-6 hours following the trauma exposure. In some embodiments the memory consolidation period is 0-1 hour following the trauma exposure.

In some embodiments, ghrelin is administered to the subject. In some embodiments, the ghrelin is in the form of acyl-ghrelin. In some embodiments, the agent targets the ghrelin receptor (GHSR). In some embodiments, the agent is a functional GHSR agonist. For example, the functional GHSR agonist may be: Adenosine, alexamorelin, Anamorelin, Capromorelin, CP-464709, Cortistatin-14, Examorelin (hexarelin), Growth Hormone Releasing Peptide-1 (GHRP-1), Growth Hormone Releasing Peptide-2 (GHRP-2), Growth Hormone Releasing Peptide-3 (GHRP-3), Growth Hormone Releasing Peptide-4 (GHRP-4), Growth Hormone Releasing Peptide-5 (GHRP-5), Growth Hormone Releasing Peptide-6 (GHRP-6), Hexamorelin, Ibutamoren (MK-677), Ibutamoren mesylate (IBU), Ipamorelin, L-692585, LY-426410, LY-444711, Macimorelin, Pralmorelin, Relamorelin, SM-130,686, Tabimorelin, Ulimorelin, or combination thereof. In some embodiments, the functional ghrelin receptor agonist is ibutamoren mesylate (IBU).

In some embodiments, the agent is a compound that enhances or facilitates the synthesis or release of ghrelin from the stomach.

In some embodiments, the agent is a compound that enhances or facilitates the acylation of ghrelin.

In some embodiments, the agent is a compound that reduces or decreases the de-acylation or breakdown of ghrelin.

In some embodiments, a therapeutically effective amount of ghrelin and the agent that enhances ghrelin signaling is administered.

In some embodiments, wherein the administering is via systemic administration, injection, or infusion directly into the BLA of the subject.

In some embodiments, the stress-sensitive psychiatric disease is selected from the group consisting of: Post-traumatic Stress Disorder (PTSD), Depressive Disorder, Major Depressive Disorders, Post-partum Depression, Bipolar Disorder, Acute Stress Disorder, Generalized Anxiety Disorder, Obsessive-Compulsive Disorder, Panic Disorders, Schizophrenia, and Trichotillomania.

In some embodiments, the subject is unstressed. In some embodiments, the subject is a human.

Further provided herein, are methods of treating stress-sensitive psychiatric diseases arising from trauma exposure in a subject, including administering to the subject a therapeutically effective amount of ghrelin or an agent that enhances ghrelin signaling in the basolateral complex of the amygdala (BLA), within a memory re-consolidation period following re-activation of a memory of a previous trauma exposure.

In some embodiments, the memory re-consolidation period is 0 hours-1 week, 0 hours-5 days, 0 hours-48 hours, or 0-24 hours following the re-activation of a memory of a previous trauma exposure. In some embodiments, the memory re-consolidation period is 0-6 hours following the re-activation of a memory of a previous trauma exposure. In some embodiments, the memory re-consolidation period is 0-1 hour following the re-activation of a memory of a previous trauma exposure.

In some embodiments, ghrelin is administered to the subject. In some embodiments, the ghrelin is in the form of acyl-ghrelin.

In some embodiments, the agent targets the ghrelin receptor (GHSR). In some embodiments, the agent is a functional GHSR agonist. For example, the functional ghrelin receptor agonist may be: Adenosine, alexamorelin, Anamorelin, Capromorelin, CP-464709, Cortistatin-14, Examorelin (hexarelin), Growth Hormone Releasing Peptide-1 (GHRP-1), Growth Hormone Releasing Peptide-2 (GHRP-2), Growth Hormone Releasing Peptide-3 (GHRP-3), Growth Hormone Releasing Peptide-4 (GHRP-4), Growth Hormone Releasing Peptide-5 (GHRP-5), Growth Hormone Releasing Peptide-6 (GHRP-6), Ibutamoren (MK-677), Ibutamoren mesylate (IBU), Ipamorelin, L-692585, LY-426410, LY-444711, Macimorelin, Pralmorelin, Relamorelin, SM-130,686, Tabimorelin, Ulimorelin, or combination thereof. In some embodiments, the functional ghrelin receptor agonist is ibutamoren mesylate (IBU).

In some embodiments, the agent is a compound that enhances or facilitates the synthesis or release of ghrelin from the stomach.

In some embodiments, ghrelin and the agent that enhances ghrelin signaling are administered to the subject.

In some embodiments, the administering is via systemic administration, injection, or infusion directly into the basolateral complex of the amygdala (BLA) of the subject.

In some embodiments, the stress-sensitive psychiatric disease is selected from the group consisting of: Post-traumatic Stress Disorder (PTSD), Depressive Disorder, Major Depressive Disorders, Bipolar Disorder, Acute Stress Disorder, Generalized Anxiety Disorder, Obsessive-Compulsive Disorder, Panic Disorders, Schizophrenia, and Trichotillomania.

In some embodiments, the subject is unstressed. In some embodiments, the subject is a human.

In some embodiments, the memory of the previous trauma exposure is a long-term memory.

Other aspects of the present disclosure provide methods of treating stress-sensitive psychiatric diseases arising from trauma exposure in a subject who has been exposed to chronic stress, including steps of: (a) upregulating the endogenous level of ghrelin receptors (GSHRs) of the subject; and (b) administering to the subject a therapeutically effective amount of ghrelin or an agent that enhances ghrelin signaling in the basolateral complex of the amygdala (BLA) of the subject, within a memory consolidation period following the trauma exposure.

In some embodiments, the step of upregulating includes administering to the subject a therapeutically effective amount of a ghrelin antagonist. In some embodiments, the ghrelin antagonist targets ghrelin or reduces endogenous ghrelin level of the subject. In some embodiments, the ghrelin antagonist is an anti-ghrelin vaccine. In some embodiments, the ghrelin antagonist targets ghrelin O-acyltransferase (GOAT). In some embodiments, the ghrelin antagonist is an anti-GOAT vaccine. In some embodiments, the ghrelin antagonist is a compound that reduces or inhibits the synthesis or release of ghrelin by the stomach. In some embodiments, the ghrelin antagonist is a compound that reduces or prevents ghrelin from crossing the blood-brain barrier.

In some embodiments, the memory consolidation period is 0 hours-1 week, 0 hours-5 days, 0 hours-48 hours, or 0-24 hours following the trauma exposure. In some embodiments, the memory consolidation period is 0-6 hours following the trauma exposure. In some embodiments, the memory consolidation period is 0-1 hour following the trauma exposure.

In some embodiments, wherein the step of administering to the subject ghrelin or the agent involves the methods of treating stress-sensitive psychiatric diseases disclosed herein.

In some embodiments, the step of upregulating further includes measuring the endogenous ghrelin levels in the subject. In some embodiments, the subject who have been exposed to chronic stress has elevated endogenous ghrelin levels compared to that of a control.

In some embodiments, the control is a subject not exposed to chronic stress. In some embodiments, the subject is a human.

Also provided herein, are methods of determining whether a subject who is not exposed to chronic stress is likely to develop stress-sensitive psychiatric diseases following a traumatic exposure. The methods include conducting an assay to measure the basal ghrelin levels in the subject, wherein the basal ghrelin level in the subject prior to the traumatic exposure is inversely related to the risk of the subject developing a stress-sensitive psychiatric disease.

In some embodiments, the assay is performed on a blood sample from the subject.

In some embodiments, the stress-sensitive psychiatric disease is selected from the group consisting of: Post-traumatic Stress Disorder (PTSD), Depressive Disorder, Major Depressive Disorders, Bipolar Disorder, Acute Stress Disorder, Generalized Anxiety Disorder, Obsessive-Compulsive Disorder, Panic Disorders, Schizophrenia, and Trichotillomania.

These and other aspects of the present disclosure, as well as various embodiments thereof, will become more apparent in reference to the drawings and detailed description of the present disclosure.

Each of the limitations of the present disclosure can encompass various embodiments of the present disclosure. It is, therefore, anticipated that each of the limitations of the present disclosure involving any one element or combinations of elements can be included in each aspect of the present disclosure

BRIEF DESCRIPTION OF DRAWINGS

FIG. 1A shows the experimental design. FIG. 1B shows acyl-ghrelin levels were not altered by fear conditioning [time: $F(5,30)=1.16$, $p=0.35$]. In contrast, corticosterone levels were rapidly and transiently elevated following fear conditioning [time: $F(5,30)=9.15$, $p<0.0001$]. FIG. 1C shows the best fit plane from a regularized linear regression, using the Lasso method, of freezing (%) predicted by ghrelin levels after fear conditioning. The best fit plane is shown in gray; each point represents one rat. The linear model coefficients retained by the Lasso method were [0 0 0 0 −0.053 −0.029] for ghrelin levels at minutes after fear conditioning=[0 10 30 60 120 180] respectively, with an intercept of 89.5 pg/ml. When the Lasso method was used as a model selection technique, ghrelin levels at time points 120 minutes and 180 minutes were retained for a subsequent multivariate linear regression. That regression produced coefficients of [−0.075 −0.047] for ghrelin levels at minutes after fear conditioning=[120 180] respectively, an intercept of 105.67 pg/ml, r-squared=0.96, p-value for the model=0.007, root mean squared error (RMSE)=4.59, and predicted residual sum of squares statistic (PRESS)=248. FIG. 1D shows a median split used to separate the rats into "high ghrelin" (light gray) and "low ghrelin" (dark gray) groups based on the average ghrelin levels across the 120 and 180 minute time points, which were most predictive of long-term auditory fear memory. The significant difference in auditory memory strength persisted across the extinction session [group: $F(1,28)=9.14$, $p<0.05$; group X time interaction: $F(7,28)=5.13$, $p<0.001$]. FIG. 1E shows a cumulative percentage plot for risk assessment behavior in individual rats during the long-term auditory fear recall test. Error bars represent ±SEM; *$p<0.05$, * $p<0.001$, **$p<0.0001$.

FIG. 2A shows the experimental design. To examine correlations between long-term fear memory and acyl-ghrelin levels measured in blood samples collected at least one week prior to fear conditioning, lateral tail vein sampling was used on unoperated rats. To avoid the influence of stress from this procedure on behavior, additional baseline blood samples were not collected. FIG. 2B shows the baseline acyl-ghrelin levels strongly and negatively predicted subsequent long-term auditory fear memory (8-minute tone extinction test) ($R^2=0.838$ for a power model; $R^2=0.685$ for a linear model).

FIG. 3A (upper panel) shows the experimental design. FIG. 3A (lower panel) shows the systemic administration of a ghrelin receptor agonist (IBU) prior to fear conditioning significantly impaired long-term auditory fear memory [group: $F(1,25)=6.96$, $p<0.05$] without affecting fear acquisition [group: $F(1,25)=0.10$, $p=0.76$] or long-term contextual memory [group: $F(1,25)=1.88$, $p=0.18$]. (n=12-15/group) FIG. 3B (upper panel) shows the experimental design. FIG. 3B (lower panel) shows intra-BLA infusion of a ghrelin receptor agonist (IBU) prior to fear conditioning significantly impaired both long-term contextual memory [group X time interaction: $F(9,117)=2.71$, $p<0.05$] and long-term auditory fear memory [group X time interaction: $F(7,91)=3.18$, $p<0.01$] without affecting fear acquisition [group X time interaction: $F(2,26)=0.55$, $p=0.58$]. (n=7-8/group) FIG. 3C shows the systemic administration of IBU at the dose used in experiment described in FIG. 3A (0.5 mg/mL) does not impact food consumption either shortly following injection (left panel; injection: $F(1,12)=1.27$, p=n.s.; injection X time interaction: $F(2,24)=1.23$, p=n.s.) or cumulatively, over the 24 hours following injection (middle panel; injection: $F(1,12)=1.23$, p=n.s.). All food consumption was expressed relative to body weight, which did not differ between the two groups (right panel; injection: $F(1,12)=0.39$, p=n.s.). (n=6-8/group) FIG. 3D shows intra-BLA infusion of IBU does not change body weight measured 24 hours after injection (injection: $F(1,23)=0.70$, p=n.s.). (n=10-15/group) Error bars represent ±SEM; *$p<0.05$, **$p<0.01$.

FIG. 4A shows the experimental design of FIG. 4B. FIG. 4B shows the representative confocal images (20×) of biotinylated ghrelin binding (gray puncta) in the BLA of an unstressed (NS) or chronically stressed (STR) rat. Gray signal represents nuclear DAPI staining. White arrowheads indicate representative ghrelin binding in cell bodies. Gray arrowheads point to staining present in the inter-neuronal cell body spaces. FIG. 4C shows chronic stress significantly decreases the binding of biotinylated ghrelin in the nuclei (upper panel; group: $F(1,10)=9.42$, $p<0.05$) and processes (middle panel; group: $F(1,10)=4.98$, $p<0.05$) of the BLA. (n=5-6/group) FIG. 4D shows that in unstressed animals, there is a strong relationship between baseline acyl-ghrelin levels and biotinylated ghrelin binding in the BLA: higher levels of circulating acyl-ghrelin are correlated with lower levels of binding. This relationship is lost in animals that experience chronic stress. FIG. 4E shows the experimental design of FIG. 4F. FIG. 4F shows systemic administration of a ghrelin receptor agonist (IBU) prior to fear conditioning significantly impaired long-term auditory fear memory in unstressed animals but not those exposed to chronic stress (group X time interaction: $F(9,93)=1.99$, $p<0.05$). No group differences were observed during fear conditioning (group X time interaction: $F(6,62)=657$ $0.82$, $p=0.56$). (n=8-9/group) Error bars represent ±SEM; *$p<0.05$.

FIG. 5C shows no differences in fear conditioning [time: $F(2,8)=2.12$, $p=0.18$] were observed between rats with high (dark gray) or low (light gray) acyl-ghrelin levels measured 2-3 hours post-conditioning. FIG. 5D shows that average acyl-ghrelin levels (2-3 hours post-conditioning) were only weakly predictive ($R^2=0.26$; linear model) of long-term context fear memory strength (10 minute context test). FIG. 5E shows that motor activity, averaged across the first three minutes in the conditioning context, prior to the first tone presentation, does not correlate with acyl-ghrelin levels. FIG. 5F shows that fear conditioning did not alter food consumption during the first 3 hours of the fear memory consolidation window [period X time interaction: $F(3,18)=0.43$, $p=0.74$]. Error bars represent ±SEM.

In FIG. 6B, the dotted lines are superimposed. For ghrelin levels, the linear model coefficients at the optimal lasso stopping point were [0 0 0 0 −0.053 -0.029] at minutes after fear conditioning=[0 10 30 60 120 180] respectively, with an intercept of 89.5 pg/ml. When the lasso method was used as a model selection technique, ghrelin levels at time points 120 minutes and 180 minutes were retained for a subsequent multivariate linear regression. That regression had coefficients [−0.075 −0.047] for ghrelin levels at minutes after fear conditioning=[120 180] respectively, and an intercept of 105.67 pg/ml, r-squared=0.964, p=0.007 for the model, RMSE=4.59, and PRESS=248.4. For corticosterone levels, the linear model coefficients at the optimal lasso stopping point were [0 0 0 0 0 0] at all time points, with an intercept of 366 pg/ml. Error bars represent ±SEM.

FIG. 7A (upper panel) shows the experimental design. FIG. 7A (lower panel) shows the systemic administration of a ghrelin receptor agonist (IBU; 0.5 mg/mL) following fear conditioning also significantly impaired both long-term contextual fear memory [group X time interaction: $F(9,72)=4.28$, $p<0.01$] and long-term auditory fear memory [group: $F(7, 56)=2.48$, $p<0.05$] without affecting fear acquisition [group: $F(1,8)=0.29$, $p=0.61$]. (n=5/group) FIG. 7B shows the systemic administration of IBU at twenty times the dose used in the experiment described in FIG. 7A (10 mg/mL) does not impact food consumption either shortly following injection (left panel; injection: $F(1,4)=1.03$, p=n.s.; injection X time interaction: $F(2,8)=0.63$, p=n.s.) or cumulatively, over the 24 h following injection (middle panel; injection: $F(1,4)=2.79$, p=n.s.). All food consumption was expressed relative to body weight. (n=5/group) Error bars represent ±SEM; $*p<0.05$, $**p<0.01$.

FIG. 9 (left panel) shows double in situ hybridization against the ghrelin receptor GHSR1a (light gray) and GAD67 (white), a marker of inhibitory interneurons, was conducted. A representative double-positive cell from the lateral nucleus of amygdala (LA) is shown; blue signal reflects nuclear DAPI staining. FIG. 9 (right panel) shows a significant portion of GHSR1a-expressing cells in two nuclei of the amygdala known to regulate fear memory (LA and the basolateral nucleus, BL) also express GAD67. Gray lines indicate the overall percentage of cells in each amygdala nucleus that express GAD67. There were significantly greater levels of GHSR1a+ cells that also expressed GAD67+ cells in the LA [02.29], $p<0.05$] than expected by chance; this was not observed for the BL [00.89], $p=0.19$]. Error bars represent ±SEM. $*p<0.05$.

DETAILED DESCRIPTION OF INVENTION

Figure 1A:
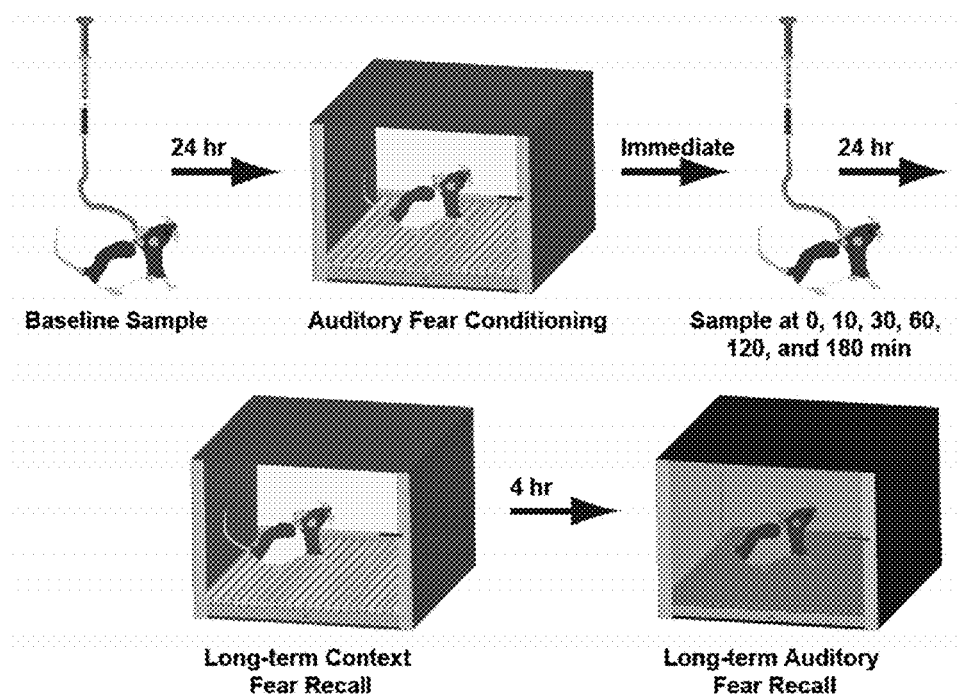
FIGS. 1A-E show post-conditioning acyl-ghrelin levels are a negative predictor of long-term fear memory strength.

The present disclosure is based, at least in part, on the surprising discovery that in unstressed subjects, endogenous peripheral acyl-ghrelin robustly inhibits the consolidation of emotional memories during trauma or stress exposure through actions in the amygdala. In particular, the data provided in the Examples section show that in unstressed subject, higher basal levels of endogenous ghrelin at the time of a traumatic exposure, as well as pharmacological agonism of the ghrelin receptor during the memory consolidation period following the traumatic exposure, decrease long-term fear memory strength. Further, the data provided herein shows that in unstressed subjects, elevated baseline levels of the endogenous peripheral acyl-ghrelin accounts for virtually all inter-individual variability in long-term fear memory strength. Accordingly, disclosed herein are methods of therapeutic and prophylactic approaches based on agonism of ghrelin or ghrelin receptor. Such methods can be used to prevent or reduce the incidence of stress-sensitive psychiatric disease, and can also be used to treat stress-sensitive psychiatric disease. Also provided herein, are methods of predicting the risk of an unstressed subject developing a stress-sensitive psychiatric disease following a traumatic exposure by measuring the basal level of ghrelin in the subject.

Further provided herein, are effects of chronic stress on the over-consolidation of emotional memories during trauma via a mechanism defined herein as "ghrelin resistance". It is disclosed herein that chronic stress, which is a risk factor for developing mental illness, increases the vulnerability of a subject in developing stress-sensitive diseases following trauma, in part, by producing ghrelin resistance. Individuals who have been exposed to chronic stress may require higher doses of compounds to achieve therapeutic effects. In past studies it was believed that antagonists of ghrelin were useful for treating stress sensitive disorders. In contrast to this teaching it was discovered according to the invention that ghrelin and ghrelin agonists are useful for treating this class of disorders. It is believed that ghrelin antagonism is actually useful in reversing ghrelin resistance, so that ghrelin and agonists thereof can be effectively delivered to treat the disorders.

"Amygdala": The amygdalae are two almond-shaped groups of nuclei located deep and medially within the temporal lobes of the brain in complex vertebrates, including humans. It is known to perform a primary role in the processing of memory, decision-making, and emotional reactions. The amygdalae are considered part of the limbic system.

"The basolateral complex of the amygdala (BLA)": The basolateral complex consists of the lateral, basal and accessory-basal nuclei of the amygdala. The primary function of the basolateral complex is stimulating fear response. The BLA is also involved in the encoding and consolidation of significant experiences and has been directly linked to memorable events. Extensive evidence suggests that stress hormones in the BLA play a critical role in consolidating new memories and this is why stressful memories are recalled vividly.

"Blood-brain barrier": The blood-brain barrier is a highly selective permeability barrier that separates the circulating blood from the brain extracellular fluid (BECF) in the central nervous system (CNS). The blood-brain barrier is formed by brain endothelial cells, which are connected by tight junctions with an extremely high electrical resistivity of at least 0.1 Ω·m. The blood-brain barrier allows the passage of water, some gases, and lipid-soluble molecules by passive diffusion, as well as the selective transport of molecules such as glucose and amino acids that are crucial to neural function. On the other hand, the blood-brain barrier may prevent the entry of lipophilic, potential neurotoxins by way of an active transport mechanism mediated by P-glycoprotein.

Memory has the ability to encode, store and recall information. Memories give an organism the capability to learn and adapt from previous experiences as well as build relationships. Encoding allows the perceived item of use or interest to be converted into a construct that can be stored within the brain and recalled later from short term or long term memory. Working memory stores information for immediate use or manipulation which is aided through hooking onto previously archived items already present in the long-term memory of an individual.

Memory encoding is a biological event that begins with perception. All perceived and striking sensations, e.g., during a traumatic exposure, travel to the brain's thalamus where all these sensations are combined into one single experience. The hippocampus is responsible for analyzing these inputs and ultimately deciding if they will be committed to long-term memory; these various threads of information are stored in various parts of the brain. Encoding is achieved using a combination of chemicals and electricity. Neurotransmitters are released when an electrical pulse crosses the synapse, which serves as a connection from nerve cells to other cells. The strength of memory encoding can be regulated. A phenomenon called long-term potentiation (LTP) allows a synapse to increase strength with increasing numbers of transmitted signals between the two neurons. LTP can be thought of as the prolonged strengthening of synaptic transmission[59] and is known to produce increases in the neurotransmitter production and receptor sensitivity, lasting minutes to even days. The process of LTP is regarded as a contributing factor to synaptic plasticity and in the growth of synaptic strength, which are suggested to underlie memory formation. LTP is also considered to be an important mechanism in terms of maintaining memories within brain regions, and therefore is thought to be involved in learning. There is compelling evidence that LTP is critical for Pavlovian fear conditioning in rats suggesting that it mediates learning and memory in mammals.

Memory consolidation is a category of processes that stabilize a memory trace after its initial acquisition. Consolidation is distinguished into two specific processes, synaptic consolidation, which is synonymous with late-phase LTP, and systems consolidation, where hippocampus-dependent memories become independent of the hippocampus over a period of weeks to years. Synaptic consolidation, or late-phase LTP[60], is one form of memory consolidation seen across all species and long-term memory tasks. Synaptic consolidation, when compared to systems consolidation, is considerably faster. There is evidence to suggest that synaptic consolidation takes place within minutes to hours of memory encoding or learning, and as such is considered the 'fast' type of consolidation. As soon as six hours after training, memories become impervious to interferences that disrupt synaptic consolidation and the formation of long-term memory. In some instances, synaptic consolidation takes as long as 24 hours. It is to be understood that when "memory consolidation" is referred to in the present disclosure, it is directed to synaptic consolidation but not system consolidation.

Memory encoding and consolidation contributes to the formation of traumatic memories in humans following an experience that causes high levels of emotional arousal and the activation of stress hormones. The strength of the traumatic memories experienced by an individual has severe biological and psycho-social impact and may trigger stress-sensitive psychiatric diseases. Because enhanced consolidation, or "over-consolidation", of fearful memories is thought to underlie the development of some trauma and stress-related disorders such as post-traumatic stress disorder (PTSD), interventions that reduce the consolidation of fear memories represent a promising strategy to prevent the development of these disorders.

Memory re-consolidation is the process of previously consolidated memories being recalled and actively reconsolidated. It is a distinct process that serves to maintain, strengthen and modify memories that are already stored in the long-term memory. Once memories undergo the process of consolidation and become part of long-term memory, they are thought of as stable. However, the retrieval of a memory trace can cause another labile phase that then requires an active process to make the memory stable after retrieval is complete. When a memory is retrieved, it goes into a labile state, which allows the memory to be altered, making it possible to treat patients with post-traumatic stress disorder or other similar anxiety based disorders. The retrieval, or the reactivation of an old, long-term memory, refers to a process during which old information is called to mind. The reactivated memory can then be modified with the help of drugs or behavioral interventions, and then re-stored with new information incorporated, i.e., reconsolidated. In accordance of the present disclosure, reducing the strength of a traumatic memory during memory reconsolidation after its reactivation, maybe key to treating stress-sensitive psychiatric diseases, e.g., PTSD caused by a traumatic exposure previously experienced by the subject, and when the traumatic memory is already a long-term memory. It is to be understood that in the present disclosure, when a "retrieval" or "reactivation" of a memory is referred to, the said memory is a long-term memory. "Retrieval" and "reactivation" maybe used interchangeably in the present disclosure when they related accessing the information stored in a long-term memory. Any means to retrieve or reactive a long-term memory that is well-known by those skilled in the art, e.g., hypnosis, maybe used in accordance with the present disclosure.

Some aspects of the present disclosure relate to the effects of stress and, in particular, chronic stress. As used herein, "stress" refers to a physical, chemical or emotional factor or combination of factors that causes bodily or mental tension and that may be a factor in disease causation. It should be appreciated that any form of stress can be compatible with aspects of the invention. Exposure to stress can be chronic or acute. As used here, "chronic stress" refers to a state of prolonged tension from internal or external stressors, which may cause various physical manifestations. Several non-limiting examples of situations where a subject could be exposed to chronic stress include military service such as a combat mission, and natural disasters, such as participation in a search-and-rescue operation or rebuilding following a natural disaster. The present disclosure provides particular insights on how chronic stress results in the over-consolidation of fearful memories following a traumatic exposure, which in turn increases risk of developing or exacerbates existing stress-sensitive psychiatric diseases arising from trauma.

Subjects at risk of, or having a stress-sensitive psychiatric disease may be treated using the methods in the present disclosure. Such subjects may have not been exposed to chronic stress (hereafter "unstressed subjects"). Such Subjects may also have been exposed to chronic stress (hereafter "stressed subjects"). It is to be understood that the "stressed subjects" and "unstressed subjects" possess all physiological or clinical traits associated with chronic stress (or lack thereof) understood by those skilled in the art.

A trauma, or traumatic exposure, or traumatic experience, as used herein, are naturally stressful in nature and emotionally overwhelm people's existing coping mechanisms. Non-limiting examples of traumatic exposures include wars, natural disasters such as earthquakes and tsunamis, violent events such as kidnapping, terrorist attacks, war, domestic abuse and sexual abuse. The terms "trauma" or "traumatic exposure", "traumatic experience", may be used interchangeably herein. It is appreciated that as used in the present disclosure, a trauma is distinct from chronic stress.

Subjects with traumatic exposures can develop stress-sensitive diseases. As used herein, a "stress-sensitive psychiatric disease" refers any condition, disease or disorder that results, at least in part, from exposure to trauma or is exacerbated, at least in part, from exposure to trauma. Non-limiting examples of stress-sensitive psychiatric diseases include Post-traumatic Stress Disorder (PTSD), Depressive Disorder, Major Depressive Disorders, Bipolar Disorder, Acute Stress Disorder, anxiety disorders such as Generalized Anxiety Disorder, Obsessive-Compulsive Disorder, social anxiety disorders, Panic Disorders, phobias, obsessive compulsive disorders, and Trichotillomania. It should be appreciated that any stress-sensitive psychiatric disease can be compatible with aspects of the present disclosure.

Post-Traumatic Stress Disorder (PTSD) is an anxiety neurosis caused by exposure to psychological damage by experience beyond a usual corrective ability such as traumas of wars, natural disasters, domestic violence or sexual abuse, etc. It is believed that in addition to psychological manifestations, shrinkage of the hippocampus and dysfunction of prefrontal cortex often occurs. The principal characteristic symptoms involve re-experiencing a traumatic (i.e., psychologically distressing) event, the avoidance of stimuli associated with that event, the numbing of general responsiveness, and increased arousal. The "events" concerned are outside the range of common experiences such as simple bereavement, chronic illness and marital conflict.

Phobias include specific phobias and social phobias. Specific phobia is an anxiety disorder of which the essential feature is a persistent fear of a circumscribed stimulus, which may be an object or situation, other than fear of having a panic attack or of humiliation or embarrassment in social situations (which falls under social phobia). Examples include phobias of flying, heights, animals, injections, and blood. Simple phobias may be referred to as "specific" phobias and, in the population at large. Exposure to the phobic stimulus will almost invariably lead to an immediate anxiety response. Social phobia is characterized by the persistent fear of social or performance situations in which embarrassment may occur.

Ghrelin is a peptide hormone produced primarily by gastrointestinal cells. In its acylated form (acyl-ghrelin), it can cross the blood-brain barrier and bind to central ghrelin receptors (growth hormone secretagogue receptor 1a, or GHSR). GHSRs are highly expressed in regions of the hypothalamus that control feeding. Accordingly, ghrelin has been extensively studied for its ability to induce feeding behavior. Ghrelin signaling is linked to obesity, diabetes and cardiovascular function. It has also been reported that increasing the levels of ghrelin leads to anti-depressant effects and that mice carrying a null mutation in the ghrelin receptor have increased depressive symptoms, suggesting that active ghrelin signaling has anti-depressant activity. Further, subjects that are subjected to chronic stress exhibit prolonged elevation of circulating endogenous ghrelin level.

GHSRs are also expressed in other brain regions not traditionally associated with feeding behavior, such as the basolateral complex of the amygdala (BLA), a brain region important for regulating fear. The abundance of GHSR in the BLA suggests that ghrelin signaling modulates fear, but the role of acyl-ghrelin in BLA-dependent fear memory has remained controversial. While some groups report that transient elevation of ghrelin signaling promotes the excitability of BLA neurons[8], others find that ghrelin decreases BLA excitability[6]. Disclosed herein is the role of endogenous acyl-ghrelin in BLA-dependent fear memory formation. Surprisingly, in unstressed subjects, acyl-ghrelin acts in the BLA as an endogenous inhibitor of fear memory consolidation and that inter-individual variation in basal circulating levels of acyl-ghrelin fully predicts inter-individual variability in long-term fear memory strength. This fear-inhibitory effect of acyl-ghrelin can be pharmacologically enhanced by either systemic or intra-BLA GHSR agonism. Importantly, these changes in fear memory strength occur without concurrent changes in either food consumption or motor activity.

In some aspects, the present disclosure pertains to the key surprising discovery showing that, in subjects not exposed to chronic stress, endogenous ghrelin levels several hours following fear learning predicts the strength of long-term emotional memories measured days later, suggesting that endogenous acyl-ghrelin negatively regulates fear memory consolidation. Thus, disclosed herein are methods of treating stress-sensitive psychiatric diseases arising from trauma exposure by administering to a subject a therapeutically effective amount of ghrelin or an agent that enhances ghrelin signaling in the BLA within a memory consolidation period following the traumatic exposure, or within a memory reconsolidation period following the reactivation of the traumatic exposure if the traumatic memory is already long-term memory of the subject. In an embodiment, the subject is an unstressed subject.

In some embodiments, a therapeutically effective amount of ghrelin is administered. Ghrelin that may be used in accordance with the present disclosure is in the form of acyl-ghrelin and is readily crossing the blood-brain barrier to reach the BLA. In some embodiments, the ghrelin administered to the subject is in its free form and is acylated by the ghrelin O-acyltransferase (GOAT) to form acyl-ghrelin, before it can cross the blood-brain barrier and reach the BLA.

In some embodiments, a therapeutically effective amount of an agent that enhances ghrelin signaling is administered. In some embodiments, the agent targets ghrelin receptor (GHSR). For example, the agent may be a functional GHSR agonist. A functional ghrelin receptor agonist, as used herein, refers to a substance or a compound that binds to and activates GHSRs to produce a biological response that mimics ghrelin signaling. The functional ghrelin agonist can be an agent that has been developed to activate ghrelin signaling in other contexts, such as to combat cachexia (loss of appetite, often observed in humans with other illnesses like cancer) or muscle loss (observed in aging humans). Non-limiting examples of commercially available agents that activate ghrelin signaling include: Adenosine, alexamorelin, Anamorelin from Helsinn Therapeutics, Capromorelin from Pfizer inc., CP-464709 from Pfizer Inc., Cortistatin-14, Examorelin (hexarelin) from Mediolanum Farmaceutici, Growth Hormone Releasing Peptide-1 (GHRP-1), Growth Hormone Releasing Peptide-3 (GHRP-3), Growth Hormone Releasing Peptide-4 (GHRP-4), Growth Hormone Releasing Peptide-5 (GHRP-5), Growth Hormone Releasing Peptide-6 (GHRP-6), Ibutamoren (MK-677) from Reverse Pharmacology, Ibutamoren mesylate (IBU), Ipamorelin from Helsinn Therapeutics, L-692,585, LY-426410 from Eli Lily, LY-444711 from Eli Lily, Macimorelin from Æterna Zentaris Inc., Pralmorelin from Kaken Pharmaceutical, Relamorelin from Rhythm Pharmaceuticals, SM-130,686, Tabimorelin from Novo Nordisk A/S, and Ulimorelin from Tranzyme Pharma And Norgine. In some embodiments, a therapeutically effective amount of Ibutamoren mesylate (IBU) is used. In other embodiments, a therapeutically effective amount of agents that enhance or facilitate the synthesis or release of ghrelin from the stomach is administered.

Non-limiting examples of agents for activating or enhancing ghrelin signaling are found in, and expressly incorporated by reference from, US Patent publication numbers: US20050148515, US20050187237, US20050257279, US20060025344, US20060025566, US20070021331, US20060293370, US20070037857, US20070191283, US20080242619, US20080261873, US20080262042, US20080300194, US20090069245, US20090131478, US20090143310, US20090156483, US20090156642, US20090163416, US20090275511, US20100227806, US20100272734, US20120095070, US20120129767, US20120232113, US20120237521, US20130123170, US20130289068, US20150031615, US20140328848, US20140088139, US20140031393, and US20130344091.

In some embodiments, both ghrelin and the agent that enhances ghrelin signaling may be administered concurrently. It is also to be understood that the agents disclosed herein for enhancing ghrelin signaling maybe administered individually or in any combination thereof, so as to achieve the desired potency of ghrelin signaling activation.

The agents described herein, "enhances" ghrelin signaling. "Enhance", as used herein, means the magnitude of ghrelin signaling in the subject increases after the subject is administered a therapeutically effective amount of the agent, e.g., a ghrelin agonist, compared to before the administration of the agent. In some instances, ghrelin signaling maybe completely lacking before the agent is administered and administering a therapeutically effective amount of the agent activates results in the presence of ghrelin signaling. In such instances, it is also considered that the agent has "enhanced" ghrelin signaling. In some embodiments, an elevated amount of ghrelin or acyl-ghrelin synthesized and released by the stomach, and/or crossing the blood-brain barrier in the subject leads to the increase in the magnitude of ghrelin signaling, especially in the BLA of the unstressed subject. In some embodiments, the increase in the magnitude of ghrelin signaling is achieved by increased occupancy of ghrelin receptors in the BLA of the unstressed subject, either by ghrelin itself or by a ghrelin agonist as described herein.

The ghrelin or the agent can be administered to the subject before, during and/or after the traumatic exposure. For example, ghrelin or the agent can be administered to a subject in anticipation of exposure to trauma, such as prior to participation in a military operation. As such, ghrelin or the agent can protect against the consequences of exposure to trauma. Ghrelin or the agent can also be administered to a subject during exposure to trauma to protect against the consequences of exposure to trauma and treat symptoms associated with the effects of trauma. Ghrelin or the agent can also be administered after exposure to trauma to protect against the consequences of exposure to trauma and treat symptoms associated with the effects of trauma. Similarly, in the embodiments wherein the subject has long-term memory of a previous traumatic exposure, ghrelin or the agent maybe administered before, during, and/or after the reactivation of a previous traumatic memory.

When ghrelin or the agent is administered before the exposure to trauma or the reactivation of a previous traumatic memory, they need to be administered at a time close enough to the onset of the traumatic exposure, e.g., a military operation, so that when the traumatic exposure occurs, the subject is protected from over-consolidation of the traumatic memory by the elevated ghrelin signaling.

When ghrelin or the agent is administered after the exposure to trauma or the reactivation of a previous traumatic memory, they need to be administered during the memory consolidation period or the memory reconsolidation period, respectively. The memory consolidation or reconsolidation period is known to be within 24 hours following the traumatic exposure or the reactivation of a previous traumatic exposure, respectively. Thus, in some embodiments, ghrelin or the agent is administered 0 hours-1 week, 0 hours-5 days, 0 hours-48 hours, or 0-24 hours following the traumatic exposure or the reactivation of a previous traumatic exposure. For example, ghrelin or the agent may be administered within 0, 1, 2, 3, 4, 5, 6, 7, 8, 9, 10, 11, 12, 13, 14, 15, 16, 17, 18, 19, 20, 21, 22, 23, or 24 hours following the traumatic exposure or the reactivation of a previous traumatic exposure. In some embodiments, ghrelin or the agent may be administered 0-23, 0-22, 0-21, 0-20, 0-19, 0-18, 0-17, 0-16, 0-15, 0-14, 0-13, 0-12, 0-11, 0-10, 0-9, 0-8, 0-7, 0-6, 0-5, 0-4, 0-3, 0-2, 0-1, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-24, 4-23, 4-22, 4-21, 4-20, 4-19, 4-18, 4-17, 4-16, 4-15, 4-14, 4-13, 4-12, 4-11, 4-10, 4-9, 4-8, 4-7, 4-6, 4-5, 5-24, 5-23, 5-22, 5-21, 5-20, 5-19, 5-18, 5-17, 5-16, 5-15, 5-14, 5-13, 5-12, 5-11, 5-10, 5-9, 5-8, 5-7, 5-6, 6-24, 6-23, 6-22, 6-21, 6-20, 6-19, 6-18, 6-17, 6-16, 6-15, 6-14, 6-13, 6-12, 6-11, 6-10, 6-9, 6-8, 6-7, 7-24, 7-23, 7-22, 7-21, 7-20, 7-19, 7-18, 7-17, 7-16, 7-15, 7-14, 7-13, 7-12, 7-11, 7-10, 7-9, 7-8, 8-24, 8-23, 8-22, 8-21, 8-20, 8-19, 8-18, 8-17, 8-16, 8-15, 8-14, 8-13, 8-12, 8-11, 8-10, 8-9, 9-24, 9-23, 9-22, 9-21, 9-20, 9-19, 9-18, 9-17, 9-16, 9-15, 9-14, 9-13, 9-12, 9-11, 9-10, 10-24, 10-23, 10-22, 10-21, 10-20, 10-19, 10-18, 10-17, 10-16, 10-15, 10-14, 10-13, 10-12, 10-11, 11-24, 11-23, 11-22, 11-21, 11-20, 11-19, 11-18, 11-17, 11-16, 11-15, 11-14, 11-13, 11-12, 12-24, 12-23, 12-22, 12-21, 12-20, 12-19, 12-18, 12-17, 12-16, 12-15, 12-14, 12-13, 13-24, 13-23, 13-22, 13-21, 13-20, 13-19, 13-18, 13-17, 13-16, 13-15, 13-14, 14-24, 14-23, 14-22, 14-21, 14-20, 14-19, 14-18, 14-17, 14-16, 14-15, 15-24, 15-23, 15-22, 15-21, 15-20, 15-19, 15-18, 15-17, 15-16, 16-24, 16-23, 16-22, 16-21, 16-20, 16-19, 16-18, 16-17, 17-24, 17-23, 17-22, 17-21, 17-20, 17-19, 17-18, 18-24, 18-23, 18-22, 18-21, 18-20, 18-19, 19-24, 19-23, 19-22, 19-21, 19-20, 20-24, 20-23, 20-22, 20-21, 21-24, 21-23, 21-22, 22-24, 22-23, or 23-24 hours following the traumatic exposure or the reactivation of a previous traumatic exposure. In some embodiments, ghrelin or the agent is administered 0-6 hours following the traumatic exposure or the reactivation of a previous traumatic exposure. In some embodiments, ghrelin or the agent is administered 0-1 hour following the traumatic exposure or the reactivation of a previous traumatic exposure.

Figure 2A:
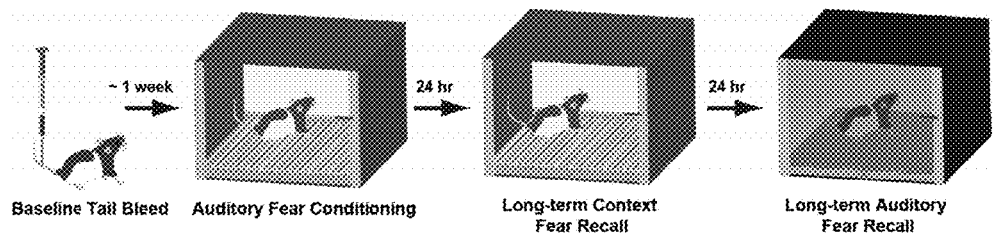
FIGS. 2A-B show pre-conditioning baseline acyl-ghrelin levels are a negative predictor of long-term fear memory strength.
Figure 2B:
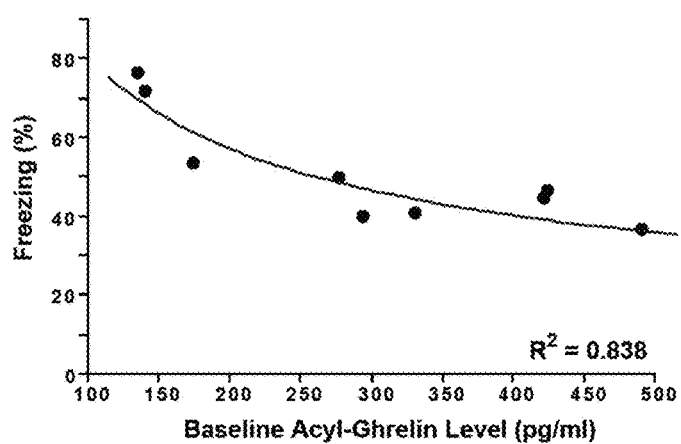

Further aspects of the present disclosure are based, in part, on the surprising finding that, basal acyl-ghrelin levels in unstressed subjects are strongly and negatively associated with long-term fear memory formation (as illustrated in FIG. 2B). Thus, some aspects of the present disclosure relate to determining whether a subject has an increased/reduced risk of developing a stress-sensitive psychiatric disease following a traumatic exposure. For example, if elevated basal levels of ghrelin are detected in the subject, the subject may be considered to be at lower risk of developing a stress-sensitive psychiatric disease following exposure to trauma. Levels of ghrelin can be measured according to any assay familiar to one of ordinary skill in the art. For example, levels of ghrelin could be measured by a Western blot or an ELISA. In some embodiments, an assay to measure ghrelin levels is conducted on a blood sample.

The level of ghrelin in a subject is compared to a control level. It should be appreciated that the appropriate control will vary depending on the circumstances. In some embodiments, the control level can be the basal level of ghrelin in a unstressed subject who has developed a stress-sensitive psychiatric disease after a traumatic exposure. Levels of ghrelin may be measured at multiple time points and may be measured before, during and after exposure to the traumatic experience. In some embodiments, a subject who has relatively low basal levels of ghrelin following exposure to trauma may be considered a subject who has an increased risk of developing a stress-sensitive psychiatric disease. A subject who is found to have low basal ghrelin levels can be administered ghrelin or an agent that enhances ghrelin signaling to reduce the risk of such subject of developing a stress-sensitive psychiatric disease following a traumatic exposure.

Other aspects of the present disclosure are based, in part, on the effect of chronic stress and the paradoxical role of ghrelin in fear memory formation. As disclosed herein, in unstressed rats, higher levels of acyl-ghrelin are associated with weaker fear memories. However, it has previously been shown that in rats exposed to chronic stress, acyl-ghrelin level is elevated and the elevated acyl-ghrelin causes enhanced fear memory formation. Similar opposing effects of ghrelin have been noted for anxiety.

It is further disclosed herein, that chronic stress, which dramatically increases fear memory by increasing endogenous acyl-ghrelin, drives a profound loss of ghrelin binding sites in the BLA. It is the cells' compensation mechanism for stress-induced upregulation of ghrelin signaling by long-term downregulating the expression of the ghrelin receptors (GHSRs). The loss of GHSRs renders a subject insensitive to the fear-inhibitory effects of GHSR agonism (a phenomenon defined herein as "ghrelin resistance", or "metabolic resistance to ghrelin"). For the first time, it is revealed that high levels of GHSR signaling can either inhibit or promote fear memory, depending on the stress history of the subject. The present disclosure provides an unexpected and intriguing new link between stress, a novel type of metabolic resistance to ghrelin, and vulnerability to excessive fear memory formation.

The loss of ghrelin receptors in the BLA and the subsequent functional ghrelin resistance induced by chronic stress make such subjects especially vulnerable to stress-sensitive psychiatric diseases (as shown in FIG. 4) when they encounter a traumatic exposure. Some aspects of the present disclosure relate to methods by which the effects of trauma in a stressed subject can be weakened to reduce the potentiating effects of the trauma on stress-sensitive psychiatric diseases. Methods associated with the present disclosure comprise upregulating the expression level of ghrelin receptors (GHSRs) in the BLA in stressed subjects and then administering to such subjects a therapeutically effective amount of ghrelin or a second agent that enhances ghrelin signaling. In some embodiments, the methods associated with the present disclosure further comprises measuring the ghrelin levels in the subject. Levels of ghrelin can be measured according to any assay familiar to one of ordinary skill in the art. For example, levels of ghrelin could be measured by a Western blot or an ELISA. In some embodiments, an assay to measure ghrelin levels is conducted on a blood sample. It is to be understood that ghrelin levels may be measured at multiple time points. For example, it may be measured before, during, or after the step of upregulating the level of GHSRs in the BLA of the subject.

The level of ghrelin in a subject is compared to a control level. It should be appreciated that the appropriate control will vary depending on the circumstances. In some embodiments, the control level can be the level of ghrelin in a subject who has not been exposed to chronic stress. In some embodiments, a stressed subject has prolonged elevated levels of ghrelin. It is to be understood, based on the ghrelin resistance mechanism described in the present disclosure, a subject who has been exposed to chronic stress and who shows an elevated endogenous level of ghrelin, also has reduced GHSR expression level in the BLA and is insensitive to the inhibitory effect of ghrelin in reducing fear memory consolidation. In some embodiments, such subject may be considered a subject who has an increased risk of developing a stress-sensitive disorder following a traumatic exposure.

To upregulate the GHSR level in the stressed subject, a therapeutically effective amount of a first agent maybe administered to the subject to antagonize ghrelin signaling. The first agent associated with the present disclosure inhibits the level or activity of a component of the ghrelin signaling pathway. Such an agent is also referred to as a ghrelin antagonist. For example, the first agent can target ghrelin itself, or the ghrelin receptor or can target one or more other factors which influence the level or activity of ghrelin, such as ghrelin O-acyltransferase (GOAT). For example, the first agent can be a vaccine, such as a vaccine against ghrelin, ghrelin receptor or GOAT. In certain embodiments, the first agent is an antagonist of the GHSR, such as a GHSR antagonist. The first agent can also be an compound that inhibits the synthesis or release of ghrelin in the stomach. The first agent may also be a compound that reduces or prevents ghrelin from crossing the blood-brain barrier. The first agent can also be a nucleic acid, such as an siRNA or an antisense molecule that inhibits expression of a ghrelin signaling component. In a preferred embodiment, the first agent is an agent that reduces the endogenous ghrelin level in the subject. It is to be understood that once the endogenous ghrelin level in the subject is reduced, the cells would compensate again by upregulating the expression of GHSRs.

The first agent that antagonizes ghrelin signaling can be an agent that has been developed to antagonize ghrelin in other contexts, such as to combat obesity or diabetes. Several non-limiting examples of commercially available agents that antagonize ghrelin signaling include: small molecule ghrelin receptor antagonists from Elixir Pharmaceuticals, ghrelin antagonist AEZS-123 from AEterna Zentaris Inc., anti-ghrelin vaccine from Cytos Biotechnology, ghrelin receptor antagonists from Merck, ghrelin antagonists from Tranzyme Pharma, small molecule ghrelin receptor antagonists from Bayer, ghrelin receptor antagonist DLys3 GHRP-6 from Phoenix Pharmaceuticals, humanized anti-ghrelin antibodies from Eli Lilly and Company and ghrelin binding nucleic acids that antagonize ghrelin activity from Noxxon Pharma AG.

Non-limiting examples of agents for inhibiting ghrelin signaling are found in, and expressly incorporated by reference from, US Patent publication numbers: US20110318807, US20110257086, US20110245161, US20110245160, US20110021420, US20100286152, US20100254994, US20100196396, US20100196330, US20100086955, US20100021487, US20090275648, US20090253673, US20090149512, US20070275877, US20070237775, US20070025991, US20050201938, US20050191317, US20050070712 and US20020187938, and from U.S. Pat. Nos. 8,013,015, 7,901,679, 7,666,833 and 7,479,271.

To upregulate the GHSR expression level in the BLA of the subject, the first agent may be administered to the subject for a period of time long enough to achieve the upregulation. For example, the first agent may be administered for 1 week to 24 months, or longer. In some embodiments, the first agent is administered for at least 1 week, 2 weeks, 3 weeks, 4 weeks, 5 weeks, 6 weeks, 7 weeks, 8 weeks, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, or 24 months. Endogenous ghrelin levels may be measured at multiple time points during the time period when the first agent is administered. A reduction in endogenous ghrelin levels is interpreted herein that the GHSR levels would increase correspondingly. It is to be understood that it may take time for GHSR levels to rise after a reduction endogenous ghrelin level is observed and that the first agent should continue to be administered following the first observation of reduction in the endogenous ghrelin level in the stressed subject.

Other aspects of the methods relate to treating stress-sensitive psychiatric diseases following a traumatic exposure in the stressed subject, wherein the subject has been administered the first agent to upregulate the GHSR level in the BLA. It may also be considered herein that, in such subjects, the ghrelin resistance induced by chronic stress is alleviate or eliminated, and that the subject is now sensitive to the inhibitory effect of ghrelin in reducing fear memory consolidation.

The method further comprises administering to the stressed subject a therapeutically effective amount of ghrelin or a second agent that enhances ghrelin signaling, following the alleviation or elimination of the ghrelin resistance induced by chronic stress. In some embodiments, a therapeutically effective amount of ghrelin is administered. Ghrelin that may be used in accordance with the present disclosure includes ghrelin that is in the form of acyl-ghrelin and readily crosses the blood-brain barrier to reach the BLA. In some embodiments, the ghrelin administered to the subject is in its free form and is acylated by the ghrelin O-acyl-transferase (GOAT) to form acyl-ghrelin.

In some embodiments, a therapeutically effective amount of a second agent that enhances ghrelin signaling is administered. In some embodiments, the second agent targets ghrelin receptor (GHSR). For example, the agent may be a functional GHSR agonist. A functional ghrelin receptor agonist, as used herein, refers to a substance or a compound that binds to and activates GHSRs to produce a biological response that mimics ghrelin signaling. The functional ghrelin agonist can be an agent that has been developed to activate ghrelin signaling in other contexts, such as to combat cachexia (loss of appetite, often observed in humans with other illnesses like cancer) or muscle loss (observed in aging humans). Several non-limiting examples of commercially available agents that activate ghrelin signaling include: Adenosine, alexamorelin, Anamorelin from Helsinn Therapeutics, Capromorelin from Pfizer inc., CP-464709 from Pfizer Inc., Cortistatin-14, Examorelin (hexarelin) from Mediolanum Farmaceutici, Growth Hormone Releasing Peptide-1 (GHRP-1), Growth Hormone Releasing Peptide-3 (GHRP-3), Growth Hormone Releasing Peptide-4 (GHRP-4), Growth Hormone Releasing Peptide-5 (GHRP-5), Growth Hormone Releasing Peptide-6 (GHRP-6), Ibutamoren (MK-677) from Reverse Pharmacology, Ibutamoren mesylate (IBU), Ipamorelin from Helsinn Therapeutics, L-692,585, LY-426410 from Eli Lily, LY-444711 from Eli Lily, Macimorelin from IEterna Zentaris Inc., Pralmorelin from Kaken Pharmaceutical, Relamorelin from Rhythm Pharmaceuticals, SM-130,686, Tabimorelin from Novo Nordisk A/S, and Ulimorelin from Tranzyme Pharma And Norgine. In other embodiments, a therapeutically effective amount of a compound that enhances or facilitates the synthesis or release of ghrelin from the stomach is administered.

Non-limiting examples of agents for activating or enhancing ghrelin signaling are found in, and expressly incorporated by reference from, US Patent publication numbers: US20050148515, US20050187237, US20050257279, US20060025344, US20060025566, US20070021331, US20060293370, US20070037857, US20070191283, US20080242619, US20080261873, US20080262042, US20080300194, US20090069245, US20090131478, US20090143310, US20090156483, US20090156642, US20090163416, US20090275511, US20100227806, US20100272734, US20120095070, US20120129767, US20120232113, US20120237521, US20130123170, US20130289068, US20150031615, US20140328848, US20140088139, US20140031393, and US20130344091.

In some embodiments, both ghrelin and the second agent that enhances ghrelin signaling may be administered concurrently. It is also to be understood that the agents disclosed herein for enhancing ghrelin signaling maybe administered individually or in any combination thereof, so as to achieve the desired potency of ghrelin signaling activation.

The second agents described herein, "enhances" ghrelin signaling. "Enhance", as used herein, means the magnitude of ghrelin signaling in the subject increases after the subject is administered a therapeutically effective amount of the agent, e.g., a ghrelin agonist, compared to before the administration of the agent. In some instances, ghrelin signaling maybe completely lacking before the agent is administered and administering a therapeutically effective amount of the agent activates results in the presence of ghrelin signaling. In such instances, it is also considered that the agent has "enhanced" ghrelin signaling. In some embodiments, an elevated amount of ghrelin or acyl-ghrelin synthesized and released by the stomach, and/or crossing the blood-brain barrier in the subject leads to the increase in the magnitude of ghrelin signaling. In some embodiments, ghrelin signaling is enhanced in the BLA of the subject. In some embodiments, the increase in the magnitude of ghrelin signaling is achieved by increased occupancy of ghrelin receptors in the BLA of the subject, either by ghrelin itself or by a ghrelin agonist as described herein.

The ghrelin or the second agent can be administered to a subject before, during and/or after the traumatic exposure. For example, ghrelin or the second agent can be administered to a subject in anticipation of exposure to trauma, such as prior to participation in a military operation. As such, ghrelin or the agent can protect against the consequences of exposure to trauma. Ghrelin or the agent can also be administered to a subject during exposure to trauma to protect against the consequences of exposure to trauma and treat symptoms associated with the effects of trauma. Ghrelin or the agent can also be administered after exposure to trauma to protect against the consequences of exposure to trauma and treat symptoms associated with the effects of trauma.

When ghrelin or the agent is administered before the exposure to trauma or the reactivation of a previous traumatic memory, they need to be administered at a time close enough to the onset of the traumatic exposure, e.g., a military operation, so that when the traumatic exposure occurs, the subject is protected from over-consolidation of the traumatic memory by the elevated ghrelin signaling.

When ghrelin or the second agent is administered after the exposure to trauma, they need to be administered during the memory consolidation period. The memory consolidation or period is known to be within 24 hours following the traumatic exposure. Thus, in some embodiments, ghrelin or the second agent is administered 0 hours-0 week, 0 hours-5 days, 0 hours-47 hours, or 0-24 hours following the traumatic exposure. For example, ghrelin or the agent may be administered within 0, 1, 2, 3, 4, 5, 6, 7, 8, 9, 10, 11, 12, 13, 14, 15, 16, 17, 18, 19, 20, 21, 22, 23, or 24 hours following the traumatic exposure. In some embodiments, ghrelin or the second agent may be administered 0-23, 0-22, 0-21, 0-20, 0-19, 0-18, 0-17, 0-16, 0-15, 0-14, 0-13, 0-12, 0-11, 0-10, 0-9, 0-8, 0-7, 0-6, 0-5, 0-4, 0-3, 0-2, 0-1, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-24, 4-23, 4-22, 4-21, 4-20, 4-19, 4-18, 4-17, 4-16, 4-15, 4-14, 4-13, 4-12, 4-11, 4-10, 4-9, 4-8, 4-7, 4-6, 4-5, 5-24, 5-23, 5-22, 5-21, 5-20, 5-19, 5-18, 5-17, 5-16, 5-15, 5-14, 5-13, 5-12, 5-11, 5-10, 5-9, 5-8, 5-7, 5-6, 6-24, 6-23, 6-22, 6-21, 6-20, 6-19, 6-18, 6-17, 6-16, 6-15, 6-14, 6-13, 6-12, 6-11, 6-10, 6-9, 6-8, 6-7, 7-24, 7-23, 7-22, 7-21, 7-20, 7-19, 7-18, 7-17, 7-16, 7-15, 7-14, 7-13, 7-12, 7-11, 7-10, 7-9, 7-8, 8-24, 8-23, 8-22, 8-21, 8-20, 8-19, 8-18, 8-17, 8-16, 8-15, 8-14, 8-13, 8-12, 8-11, 8-10, 8-9, 9-24, 9-23, 9-22, 9-21, 9-20, 9-19, 9-18, 9-17, 9-16, 9-15, 9-14, 9-13, 9-12, 9-11, 9-10, 10-24, 10-23, 10-22, 10-21, 10-20, 10-19, 10-18, 10-17, 10-16, 10-15, 10-14, 10-13, 10-12, 10-11, 11-24, 11-23, 11-22, 11-21, 11-20, 11-19, 11-18, 11-17, 11-16, 11-15, 11-14, 11-13, 11-12, 12-24, 12-23, 12-22, 12-21, 12-20, 12-19, 12-18, 12-17, 12-16, 12-15, 12-14, 12-13, 13-24, 13-23, 13-22, 13-21, 13-20, 13-19, 13-18, 13-17, 13-16, 13-15, 13-14, 14-24, 14-23, 14-22, 14-21, 14-20, 14-19, 14-18, 14-17, 14-16, 14-15, 15-24, 15-23, 15-22, 15-21, 15-20, 15-19, 15-18, 15-17, 15-16, 16-24, 16-23, 16-22, 16-21, 16-20, 16-19, 16-18, 16-17, 17-24, 17-23, 17-22, 17-21, 17-20, 17-19, 17-18, 18-24, 18-23, 18-22, 18-21, 18-20, 18-19, 19-24, 19-23, 19-22, 19-21, 19-20, 20-24, 20-23, 20-22, 20-21, 21-24, 21-23, 21-22, 22-24, 22-23, or 23-24 hours following the traumatic exposure. In some embodiments, ghrelin or the second agent is administered 0-6 hours following the traumatic exposure. In some embodiments, ghrelin or the second agent is administered 0-1 hour following the traumatic exposure.

Enhancing endogenous mechanisms for inhibiting fear memory consolidation represents an especially attractive target for preventing PTSD following trauma in humans. Two other endogenous substances are known to inhibit fear memory formation: the inhibitory neurotransmitter GABA and the endogenous opioid β-endorphin. In the BLA, GABA plays a role in the consolidation of some but not all types of aversive memory. In humans, individuals with low plasma levels of GABA at the time of trauma have higher rates of PTSD than those with higher plasma levels of GABA. By contrast, enhancement of β-endorphin signaling by administration of exogenous β-endorphin or opioid receptor agonists can interfere with aversive memory consolidation. Additionally, morphine, an opioid drug that binds to the same receptor as β-endorphin, given immediately following trauma reduces the subsequent development of PTSD in humans. Thus, enhancing ghrelin, GABAergic, or β-endorphin signaling can reduce fear memory consolidation and represent attractive targets for preventing the development of PTSD in humans. Unlike opioid or GABA receptor agonists, ghrelin agonists are not addictive and therefore potentially represent a less risky and more promising intervention in trauma-exposed humans at risk for PTSD. For example, it is also highlighted in the present disclosure that a history of stress exposure promotes ghrelin resistance in the amygdala. In this case, higher doses of GABA receptor agonists or ghrelin may be required to achieve therapeutic efficacy in fear memory reduction. And for the reason stated above, the non-addictive ghrelin or ghrelin agonists are much more suitable than GABA receptor agonists.

In its broadest sense, the terms "treatment" or "to treat" refer to both therapeutic and prophylactic treatments. If the subject in need of treatment is experiencing a condition (i.e., has or is having a particular condition), then "treating the condition" refers to ameliorating, reducing or eliminating one or more symptoms associated with the disorder or the severity of the disease or preventing any further progression of the disease. If the subject in need of treatment is one who is at risk of having a condition, then treating the subject refers to reducing the risk of the subject having the condition or preventing the subject from developing the condition.

A subject shall mean a human or vertebrate animal or mammal including but not limited to a dog, cat, horse, cow, pig, sheep, goat, turkey, chicken, and primate, e.g., monkey. The methods of the present disclosure are useful for treating a subject in need thereof. A subject in need thereof can be a subject who will be exposed to trauma, is currently exposed to trauma or has been exposed to trauma. For example, a subject in need thereof may be a subject involved, or who will be involved, in a military operation or combat mission. A subject in need thereof can be a subject having or at risk of a stress-sensitive psychiatric disease. For example, a subject can be a patient who is diagnosed with a stress-sensitive psychiatric disease, or a subject with a strong familial history of such disorders.

Therapeutic compounds or agents, e.g., ghrelin or functional ghrelin agonists and other compounds that enhance ghrelin signaling, or reversal of ghrelin resistance associated with the present disclosure may be directly administered to the subject or may be administered in conjunction with a delivery device or vehicle. Delivery vehicles or delivery devices for delivering therapeutic compounds to surfaces have been described. The therapeutic compounds of the present disclosure may be administered alone (e.g., in saline or buffer) or using any delivery vehicles known in the art.

The term "therapeutically effective amount" of the present disclosure refers to the amount necessary or sufficient to realize a desired biologic effect. For example, a therapeutically effective amount of a ghrelin agonist associated with the present disclosure may be that amount sufficient to ameliorate one or more symptoms of a stress-sensitive psychiatric disease in a subject who has had a traumatic exposure. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic compounds being administered the size of the subject, or the severity of the disease or condition. One of ordinary skill in the art can empirically determine the effective amount of a particular therapeutic compound associated with the present disclosure without necessitating undue experimentation.

Subject doses of the compounds described herein for delivery typically range from about 0.1 µg to 10 mg per administration, which depending on the application could be given daily, weekly, or monthly and any other amount of time there between. In some embodiments a single dose is administered during the critical consolidation or reconsolidation period. The doses for these purposes may range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

In some embodiments a compound of the present disclosure is administered at a dosage of between about 1 and 10 mg/kg of body weight of the mammal. In other embodiments a compound of the present disclosure is administered at a dosage of between about 0.001 and 1 mg/kg of body weight of the mammal. In yet other embodiments a compound of the present disclosure is administered at a dosage of between about 10-100 ng/kg, 100-500 ng/kg, 500 ng/kg-1 mg/kg, or 1-5 mg/kg of body weight of the mammal, or any individual dosage therein.

The formulations of the present disclosure are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of the therapeutic compound associated with the present disclosure can be administered to a subject by any mode that delivers the therapeutic agent or compound to the desired surface, e.g., mucosal, systemic. Administering the pharmaceutical composition of the present disclosure may be accomplished by any means known to the skilled artisan. Preferred routes of administration include but are not limited to oral, parenteral, intramuscular, intranasal, sublingual, intratracheal, inhalation, ocular, vaginal, rectal and intracerebroventricular. In some embodiments, a therapeutically effective amount of ghrelin or an agent that enhances ghrelin signaling maybe infused directly to the basolateral complex of the amygdala (BLA) of the subject.

For oral administration, the therapeutic compounds of the present disclosure can be formulated readily by combining the active compound(s) with pharmaceutically acceptable carriers well known in the art. Such carriers enable the compounds of the present disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189). Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is preferred. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the therapeutic agent may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the therapeutic agent either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the therapeutic compounds of the present disclosure. The therapeutic agent is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this present disclosure are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this present disclosure are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of therapeutic agent. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified therapeutic agent may also be prepared in different formulations depending on the type of chemical modification or the type of device employed.

Formulations suitable for use with a nebulizer, either jet or ultrasonic, will typically comprise therapeutic agent dissolved in water at a concentration of about 0.1 to 25 mg of biologically active compound per mL of solution. The formulation may also include a buffer and a simple sugar (e.g., for stabilization and regulation of osmotic pressure).

The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing therapeutic agent and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Intra-nasal delivery of a pharmaceutical composition of the present disclosure is also contemplated. Intra-nasal delivery allows the passage of a pharmaceutical composition of the present disclosure to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present disclosure solution into a chamber of defined volume, which chamber has an aperture dimensioned to aerosolize and aerosol formulation by forming a spray when a liquid in the chamber is compressed. The chamber is compressed to administer the pharmaceutical composition of the present disclosure. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The agents, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The therapeutic compounds of the present disclosure and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the present disclosure contain an effective amount of a therapeutic compound of the present disclosure optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

The therapeutic agents may be delivered to the brain using a formulation capable of delivering a therapeutic agent across the blood brain barrier. One obstacle to delivering therapeutics to the brain is the physiology and structure of the brain. The blood-brain barrier is made up of specialized capillaries lined with a single layer of endothelial cells. The region between cells are sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipophilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. Others are known to those of skill in the art.

The therapeutic agents of the present disclosure may be delivered with other therapeutics for treating stress-sensitive psychiatric diseases.

The following examples are provided to illustrate specific instances of the practice of the present disclosure and are not intended to limit the scope of the present disclosure. As will be apparent to one of ordinary skill in the art, the present disclosure will find application in a variety of compositions and methods.

EXAMPLES

Example 1

Described here are findings that agents resulting in functional agonism of the hormone ghrelin can be used to protect humans from stress-sensitive diseases involving excessive negative affect, and also to treat such diseases. These diseases include, but are not limited to, Post-traumatic Stress Disorder (PTSD), Depressive Disorder, Major Depressive Disorders, Bipolar Disorder, Acute Stress Disorder, Generalized Anxiety Disorder, Obsessive-Compulsive Disorder, Panic Disorders, Schizophrenia and Trichotillomania.

The invention provides a method to reduce the consolidation of emotional memories during trauma or stress exposure to reduce the development of stress-sensitive mental illnesses. The method comprises administration of a therapeutically effective amount of either ghrelin or a functional ghrelin receptor agonist to humans shortly (immediately to one day) following trauma exposure in order to prevent the development of stress-sensitive mental disorders.

Additionally for humans who have been exposed to trauma in the past, that ghrelin or a functional ghrelin receptor agonist may be administered shortly following re-activation of the memory of a traumatic experience to reduce reconsolidation of the memory, and reduce the impact of the trauma on stress-sensitive mental disorders.

Additionally, chronic stress, which is a risk factor for developing mental illness, produces this vulnerability, in part, by producing ghrelin resistance. Individuals who have a high stress "load" may benefit from higher doses of compounds to achieve therapeutic effects and/or treatment with an agent that reduces ghrelin resistance.

Example 2: Central Ghrelin Resistance Promotes the Over-Consolidation of Fear Memory It is reported here that in unstressed rodents, endogenous peripheral acyl-ghrelin robustly inhibits fear memory consolidation through actions in the amygdala and accounts for virtually all inter-individual variability in long-term fear memory strength. Higher levels of endogenous ghrelin after fear learning, as well as pharmacological agonism of the ghrelin receptor during the memory consolidation period, decrease long-term fear memory strength. These fear-inhibitory effects cannot be explained by changes in appetitive behavior. In contrast, it is shown that chronic stress, which increases both circulating endogenous acyl-ghrelin and fear memory formation, promotes both a profound loss of ghrelin binding sites in the amygdala and behavioral resistance to inhibitory ghrelin signaling. This work provides new insights into the process by which chronic stress serves as a risk factor for the over-encoding of traumatic memories and reveals that ghrelin can regulate negative emotionality independent of its role in hunger.

Materials and Methods

Subjects

All experiments used adult, male Long Evans rats (300-350 g, Charles River, Raleigh, N.C. or 250-275 g, Taconic, Germantown, N.Y.), individually housed (68-72° F.; 12-h light/dark cycle, 0700 h lights on). Control animals were housed in separate cubicles from stressed animals. Water and food was given ad libitum. All procedures were approved by the Institutional Animal Care and Use Committee of the Massachusetts Institute of Technology and the Animal Care and Use Review Office of the US Army Medical Research and Materiel Command and in accordance with the US National Institutes of Health (NIH) Guide for the Care and Use of Laboratory Animals.

Drug Preparation

Some rats received systemic or intra-BLA delivery of ibutamoren mesylate (IBU). For systemic drug delivery, rats were injected with 1 ml kg$^{-1}$ intraperitoneal injection (i.p.) of either vehicle or drug. Ibutamoren mesylate (Axon Medchem, Groningen, The Netherlands) is a specific GHSR1a agonist with a half-life of >6 h and readily crosses the blood-brain barrier[46]. A concentration of 0.5 mg ml$^{-1}$, diluted in saline, was used. For experiments using intra-BLA drug delivery, ibutamoren mesylate was solubilized in artificial cerebrospinal fluid (pH=7.4) to a concentration of 0.5 µg µl$^{-1}$.

Surgical Procedures

Some rats received externalized jugular vein catheters or bilateral intra-BLA cannulae. Some rats were purchased from a commercial supplier with externalized jugular vein catheter implants. Catheters were flushed with sterile saline (0.1 cc) every other day until fear conditioning commenced. Sterile heparin lock solution was infused after the saline flush to maintain the patency of the catheter.

Some rats received bilateral implants of stainless steel cannulae aimed at the BLA. Rats were anesthetized with a cocktail of 10 mg kg$^{-1}$ acepromazine, 100 mg kg$^{-1}$ xylazine, and 100 mg kg$^{-1}$ ketamine (1 ml kg$^{-1}$; i.p.) and placed in a dual arm stereotaxic frame (Kopf Instruments; Tujunga, Calif.). The rats were then implanted with 23 gauge guide cannulae 1 mm above LA using the following coordinates, relative to bregma and brain surface: A/P −2.0, M/L+/−5.3, D/V −5.4. Three jeweler screws were also implanted in the skull, and dental acrylic was used to secure the implant. Dummy cannulae extending 1 mm past the tip of the guide cannulae were placed into the guide cannula after surgery and changed every other day. Rats received 0.03 mg kg$^{-1}$ of Buprenex (1 ml kg$^{-1}$; subcutaneous injection (s.c.)) for post-operative pain management. All rats recovered for a minimum of 5 days.

Blood Collection

Some rats had blood samples collected Samples were placed in tubes on ice until they were spun (2100 g, 4° C., 10 minutes). The supernatant (plasma) was placed in new tubes. For analysis of acylated ghrelin, 60 µl was placed in a tube containing 3 µl of 0.5M HCl. For analysis of corticosterone, 15 µl was placed in another tube. The remainder was placed in a third tube. All tubes were stored at −80° C. until analysis.

Rats with jugular catheters were gently restrained while the catheter plug was removed. A sterile syringe and needle were used to remove the heparin lock solution (SAGENT Pharmaceuticals; Schaumburg, Ill.). A new sterile syringe and needle were used to withdraw approximately 500 µl of blood, which was placed into a small tube containing 10 µl of 0.1M EDTA and 4 µl of HALT cocktail (Thermo Scientific/Rockford, Ill.). Each catheter was flushed with sterile saline (~0.15 cc) and 0.05 cc of sterile heparin lock solution was injected into the catheter. Sterile catheter plugs were reinserted.

For tail bleeding, rats were gently restrained in a clean lab coat and the tail was warmed in water. A heparinized butterfly catheter (26 g) was used to remove approximately 500 µl of blood from the lateral tail vein, as previously described[47].

Behavioral Testing

Some rats were subjected to auditory Pavlovian fear conditioning and extinction testing, a food consumption assay, or chronic immobilization stress.

A subset of rats were subjected to auditory Pavlovian fear conditioning and extinction testing. All rats were transported in their home cages from the vivarium to a holding room in which no behavioral testing was conducted. This transport occurred at least one hour prior to the onset of any behavioral testing.

For catheterized rats, each rat was placed in a fear conditioning box (MedAssociates; St. Albans, Vt.) scented with Pine-Sol (1%) for 250 sec total. The rats had 3 minutes to explore the novel environment before tone (10 seconds, 85 dB)-shock (2 seconds, 0.35 mA; coterminating with the tone) pairings [20 second intertrial intervals (ITIs)] were administered. Long-term context and tone fear memory was assessed the following day. For context extinction, the rats were returned to the fear conditioning context for a total of 10 minutes. Four hours later, tone extinction was administered by placing the rats in the fear conditioning boxes with an altered context. White Plexiglas inserts were used to obscure the back and side walls and cover the grid floor. Room and box lights were turned off, a red light provided illumination (15 W), and acetic acid (1%) was used to scent the boxes. Two minutes were allowed for exploration before a continuous tone (8 minutes, 87 dB) was presented. For rats with BLA cannula implants, all conditioning and testing was as described, except context and tone extinction were separated by 24 hours.

For rats that did not have any surgical procedures, each rat was tested as above, but with the following changes. On the fear conditioning day, rats were exposed to four tone-shock pairings with a 60 second ITI (460 seconds total time). For context extinction, rats were returned to the conditioning context for 12 minutes total. For tone extinction, rats were exposed to twelve tones (10 seconds, 85 dB) for 960 seconds total. Conditioning, context and tone extinction sessions were separated by 24 hours.

Infrared cameras (frame rate: 30 Hz) and VideoFreeze software (MedAssociates; St Albans, Vt.) were used to record behavior during all training and testing sessions. Motor activity was measured using the "motion index", a number generated by the VideoFreeze software, which corresponds roughly to the change in grayscale values across the image pixels; a higher motion index indicates greater movement. Freezing was measured by computing the number of observations below a threshold motion index and converting this number to a percentage of all observations for the period of interest. The threshold defined the value of the motion index below which only motor activity related to breathing was observed.

Risk assessment behavior was defined as periods (>1 second duration) when a rat's body was immobile, but the head was moving. This behavior was quantified by an experienced observer, who watched the videos, blinded to the ghrelin level of the rat, and scored risk assessment on a second-by-second basis for the ten minute long-term auditory fear recall test. Risk assessment behavior was scored twice for each rat.

Hormone Assays

Corticosterone and acylated-ghrelin levels were measured with commercial ELISA kits. For acylated ghrelin, undiluted, acidified samples were processed according to the manufacturer's protocol (Millipore; Billerica, Mass.). For corticosterone, non-acidified plasma was diluted 1:40 in Assay Buffer 15 (Enzo Life Sciences; Farmingdale, N.Y.). No samples displayed signs of hemolysis or lipemia. All reported values were dilution-corrected.

Ghrelin Binding

Because the specificity of commercial antibodies for GHSR is unknown, biotinylated ghrelin was used to visualize ghrelin binding sites[11] in brain sections containing the BLA. Anesthetized (Isoflurane; 3%) rats were transcardially perfused with ice-cold saline, followed by an ice-cold fixative containing 4% paraformaldehyde (PBS), pH 7.4. Brains were immediately removed and post-fixed in the same fixative for 2-16 hours. The brains were then transferred to 30% sucrose in 0.1M PBS. After several days, brains were cryosectioned into 30 µm sections. Sections containing the BLA were mounted on gelatinized slides, dried at 4° C. for 1-2 hours, and subsequently stored at −80° C. until staining.

Figure 8:
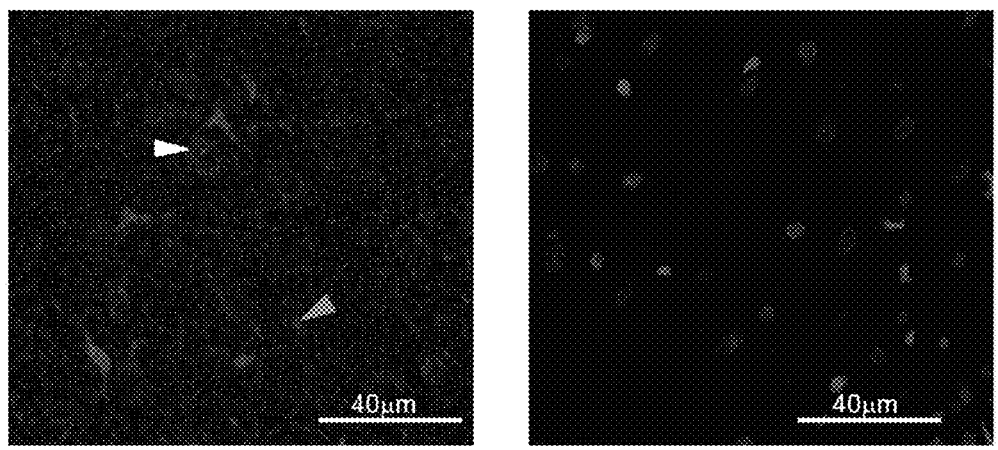
FIG. 8 shows negative control staining reveals low background binding of biotinylated acyl-ghrelin. Sections containing the BLA expressed high levels of signal when incubated with biotinylated ghrelin (left panel, gray puncta). In contrast, this signal was almost absent in BLA sections in which incubation was performed without biotinylated ghrelin (right panel). Gray signal represents DAPI staining.

Sections were defrosted for 5 minutes. A wax boundary was drawn around the slices to minimize loss of liquid during the procedure. Slices were washed twice in 1×PBS in a tub on a shaker (5 minutes/wash). Sections were permeabilized in 0.25% Triton X in 1×PBS for 15 min. Sections were then washed in 1×PBS (3 times, 5 minutes/wash). Two drops of Reagent A (Streptavidin) from the Endogenous Biotin Blocking Kit (Invitrogen Corporation; Grand Island, N.Y.) were added per brain slice and left to incubate for 1 hour at room temperature. Sections were washed in 1×PBS (3 times, 5 minutes/wash). Two drops of Reagent B (biotin) from the Endogenous Biotin Blocking Kit were added per slice and left to incubate for 1 hour at room temperature. Sections were washed in 1×PBS (3 times, 5 minutes/wash). Fresh aliquots of human biotin-acyl-ghrelin (AnaSpec; Fremont, Calif.) were then thawed by hand, gently vortexed, and added into 1×PBS at a 1:250 dilution. The mixture was gently vortexed and quickly added to the brain slices. Sections were incubated overnight (18 hours) at 4° C. in a humidified refrigerator. Some sections containing the BLA were run as a negative control, and were incubated in 1×PBS overnight instead of biotin-ghrelin (FIG. 8).

The following day, sections were washed with 1×PBS (4 times, 5 minutes/wash). The blocking steps of the previous day (using streptavidin Reagent A, biotin Reagent B, and 1×PBS washes between and after) were repeated. Sections were then incubated with the secondary antibody [Alexa 594 fluorescent dye conjugated to streptavidin (1:200 dilution in 1×PBS, slightly vortexed when mixed)] for 60 minute in a dark environment. Slices were washed in 1×PBS 4 times for 5 minutes each and were subsequently coverslipped with VectaShield with DAPI mounting medium for fluorescence (Vector Laboratories; Burlingame, Calif.). Samples were stored at 4° C. in the dark until imaging.

In Situ Hybridization

Fluorescence in situ hybridization staining was carried out to visualize GHSR1a mRNA and GAD67 mRNA in the BLA using the QuantiGene ViewRNA ISH Tissue 2-Plex kit (Affymetrix; Santa Clara, Calif.) and staining procedures were performed according to the manufacturer's protocol.

Four deeply anesthetized (Isoflurane; 3%) rats were transcardially perfused with ice-cold saline containing 0.1% diethylpyrocarbonate (DEPC), followed by an ice-cold fixative containing 4% paraformaldehyde and 0.1% DEPC in 0.1M phosphate buffered saline (PBS), pH 7.3. Brains were immediately removed and post-fixed in the same fixative for 2 hours. The brains were then cryoprotected in 30% sucrose in 0.1M PBS and cryosectioned into sixteen 20-μm-thick sections containing the middle BLA (between −2.8 to −3.14 mm posterior to bregma).

Tissue sections were first dehydrated using increasing concentration of ethanol (50%, 70% and 100%) and then baked at 60° C. for 30 minutes. The sections were then treated with Proteinase solution at 40° C. for 40 minutes and hybridized for 2 hours at 40° C. with custom-designed QuantiGene ViewRNA probes that are complement to GHSR1a and GAD67. Unbound probes were washed out with Wash buffer and the bounded probes were then hybridized with PreAmp solution for 25 minutes at 40° C., followed by Amp solution for 15 minutes at 40° C. Two Label Probes (LP), that are conjugated to alkaline phosphatase (AP), were used to visualize the hybridization, of which the GHSR1a was visualized by LP-AP-type 1 that reacted with Fast Red Substrate to deliver Cy3 fluorescence, whereas GAD67 by LP-AP-type 6 that reacted with Fast Blue Substrate to deliver Cy5 fluorescence. Sections were counterstained with Gill's Hematoxylin (Sigma-Aldrich; St. Louis, Mo.) for the anatomical localization of amygdala nuclei, and with DAPI to label the nuclei. Slides were then mounted in Ultramount mounting medium (DAKO; Carpinteria, Calif.).

Food Consumption Assay

For some rats, food consumption was monitored. After fear conditioning as described above, each rat was returned to its home cage in a holding room. Each rat had 200 g of chow placed in the food hopper. Food was quickly weighed and returned 30 minutes, 1 hour, 2 hours, and 3 hours after fear conditioning ended. Three days after fear recall testing (five days after fear conditioning), food consumption was measured during the same time points within the day, but while the rats were undisturbed in their home cages in the vivarium.

Chronic Immobilization Stress

For 14 consecutive days, stress-exposed rats were transferred from the animal facility to a behavioral testing room used only for stress at 12:00 PM, when immobilization stress began. Animals were placed in Decapicone plastic bags (Braintree Scientific; Braintree, Mass.), which were secured at the tail. Immobilized rats were secured in pairs to the floor of cages lacking bedding. They were returned to their home cages at 4:00 PM.

Unstressed controls were handled daily for one minute. In addition, from 12:00-4:00 PM, these animals remained in their home cages without food and water, so that all animals experienced short-term food and water deprivation. This insured that any differences in ghrelin binding in brain tissue across groups could be attributed to the differences in stress exposure, rather than differences in food availability.

Imaging

Multi-channel florescent images were acquired from brain sections containing the BLA to measure ghrelin binding and mRNA expression of GHSR and GAD67.

Brain slices were imaged using a 20× objective on a Zeiss LSM 700 confocal laser scanning microscope coupled with Zen imaging software. Images of the left and right BLA were obtained based on the structure and coordinates of these regions from standard rat brain atlas[48]. One animal was excluded from all analysis because the BLA could not be identified with confidence.

Images were quantified using the ImageJ software version 1.49 (National Institutes of Health; Bethesda, Md.). For cell body analyses of the regions of interest (ROI), 30 cells in 3 different regions of each BLA were randomly selected and outlined on the DAPI channel (yielding a total of 90 ROIs sampled per image). This method prevented bias that could occur if cells were selected on the 594 biotinylated ghrelin channel. The circular regions were then superimposed onto the 594 channel and the average fluorescence intensity for each cell was determined by the software. These values were averaged for each image to yield the per-animal fluorescence level for each brain region. This number represented the amount of ghrelin binding in statistical analyses.

A similar procedure was followed to compute ghrelin binding on neuronal or glial processes. Circular ROIs were placed in regions lacking cell bodies, as identified on the DAPI channel. Ten ROIs from each of 3 different regions per BLA were analyzed (yielding a total of 30 ROIs).

Fluorescent microscopy images were acquired using Zeiss AxioVision software (Carl Zeiss MicroImaging, Inc., Thornwood, N.Y.) interfaced with a Zeiss Axio Observer A1 fluorescence microscope with an AxioCam MRm camera. Images were all captured using a 63× objective from amygdala nuclei according to a brain atlas[48]. Two or three images (142 μm×106.5 μm) were captured for each region from each section (5-6 sections matched for rostral-caudal position across the amygdala) from 3 rats. Images were exported as 8-bit TIFF files and nuclear expression of target mRNAs was quantified using ImageJ software (NIH, Bethesda, Md.). The total number of all cells (determined by quantifying DAPI+ nuclei) was quantified in each image. The expression of target mRNAs was quantified by examining the expression of fluorescent grains immediately adjacent or overlapping with each nucleus. GHSR1a receptors were identified as red grains (using a CY3/TRITC filter); GAD67-expressing cells were identified by green grains (CY5 filter, green). The number of cells expressing both GHSR1a and GAD67 was also identified. Percentages of cells expressing GAD67 were calculated by dividing the total number of GAD67+ cells per region over the total number of all DAPI+ nuclei per region. Similarly, percentages of cells expressing GHSR1a were calculated by dividing the total numbers of GHSR1 cells by the total numbers of DAPI+ nuclei. The percentage of GHSR1a cells expressing GAD67 was calculated by dividing the total number of GHSR1a+/GAD67+ cells by the total number of GHSR1a+ cells.

Statistics

Statistical tests were used to determine significance of all reported values. For all statistical tests, the significance threshold was $p<0.05$.

To assess fear memory strength, conditional freezing was expressed as the percentage of time spent freezing, a probability estimate amenable to analysis with parametric statistics. These estimates of freezing, as well as hormone levels and data related to food consumption and body weight, were analyzed using ANOVA. Post hoc Fisher's PLSD tests were performed after a significant omnibus F-ratio.

To determine the relationships between hormone levels and fear memory strength, assessed was to what extent a single measurement of ghrelin or corticosterone level could explain percent freezing in a rat. 14 linear regressions were computed with freezing as the dependent variable and ghrelin or corticosterone level at each time point (baseline; t=0 to 180 minutes) as the independent variable, plus an intercept term. For each regression, the predicted residual sum of squares (PRESS) statistic[49] was also computed using the function "press" in MATLAB (The Mathworks, Inc.). The PRESS statistic is a leave-one-out cross-validation method that provides an estimate of how well an equation will generalize (perform on an independent data set that was not itself used to fit the regression). The PRESS statistic can be calculated for a number of candidate regression models, with the lowest values of PRESS indicating the models most likely to have good generalization.

Also assessed was whether linear regressions in multiple variables, which included measurements of ghrelin and/or corticosterone levels at multiple time points, could better explain freezing data than a single measurement. Because the number of experimental animals (n=6) was close to the number of time points (n=7), a model selection technique was applied to select which hormone measurements to include in a linear regression model, to avoid overfitting the data and to identify linear models with good generalization properties which would perform well on independent data sets. The Lasso (least absolute shrinkage and selection operator) method[50] is a technique for estimating linear models that penalizes overfitting, and that tends to set some coefficients equal to zero. The Lasso method can thus be used for model selection by retaining the nonzero coefficients in a subsequent linear regression model. The Lasso procedure is well suited to datasets like this one, in which the number of subjects is similar to the number of independent variables. Two Lasso regressions were performed in MATLAB using the "lasso" function, one with ghrelin levels from all time points as the independent variables, and a second corticosterone levels at all time points. Three-fold cross-validation was used in the lasso function.

For ghrelin binding, a one-way ANOVA was used to determine whether ghrelin binding differed between stress-exposed and control rats. All statistical tests were computed using per-animal averages of each measure.

For the in situ hybridization, a one-tailed one sample t-test was used to determine whether the average percent of GAD67+/GHSR1a+ double-positive cells within each brain region was significantly different from the mean percentage of GHSR1a+ cells within the same brain region. All statistical tests were computed using per-animal averages of each measure.

Results and Discussion

Figure 1B:
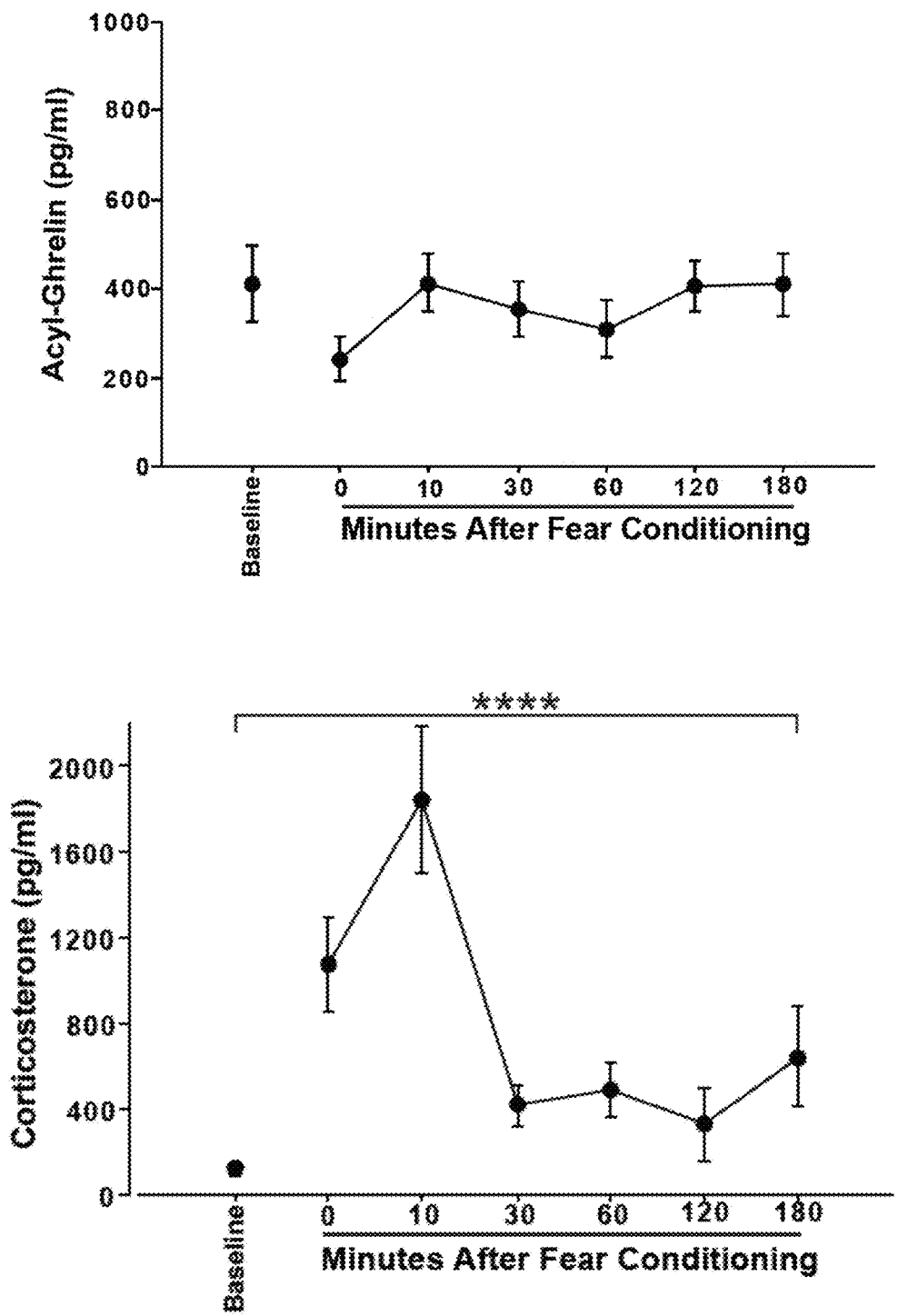

Using healthy, unstressed rats implanted with jugular vein catheters to enable repeated within-subject blood sampling, blood samples were taken prior to and at various time points following auditory Pavlovian fear conditioning (FIG. 1A). It was found that circulating acyl-ghrelin levels were not significantly altered by the brief (less than 3 minutes total duration) fear conditioning paradigm used here (FIG. 1B, upper panel), in contrast to corticosterone levels (FIG. 1B, lower panel). It was sought to determine whether acyl-ghrelin or corticosterone levels at any of the time points surrounding memory encoding determined subsequent long-term fear memory strength in rats. Long-term auditory fear memory strength was assessed two days following fear conditioning, a time point beyond the time in which short-term memory undergoes synaptic consolidation to form long-term memory[12]. Linear regressions were computed to test the hypothesis of a linear relationship between the rats' hormone levels around conditioning and freezing behavior measured more than 24 hours later (see Materials and Methods).

Figure 1C:
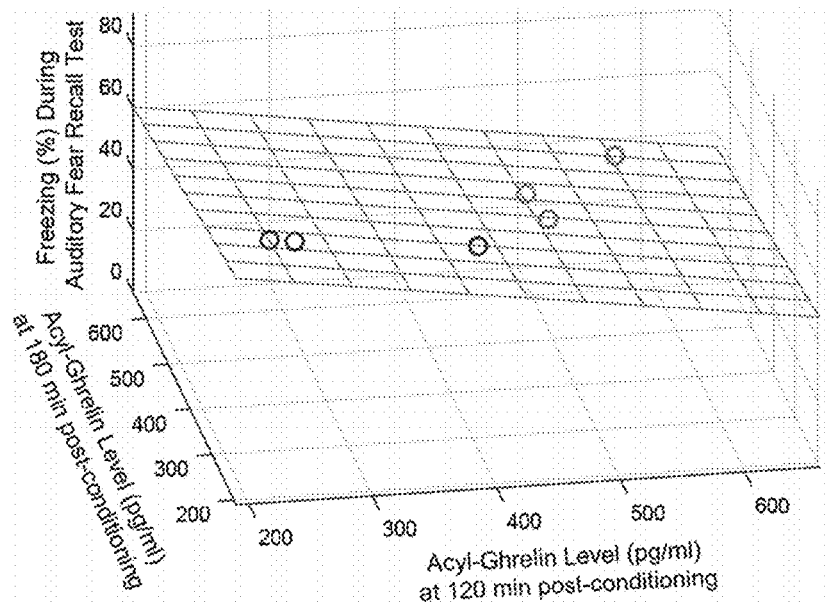
Figure 1D:
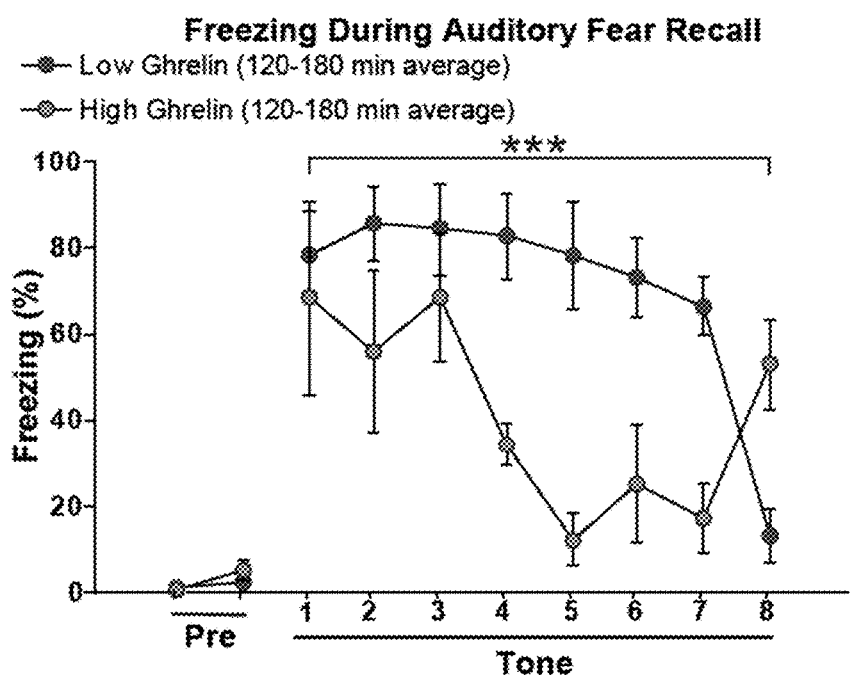
Figure 5A:
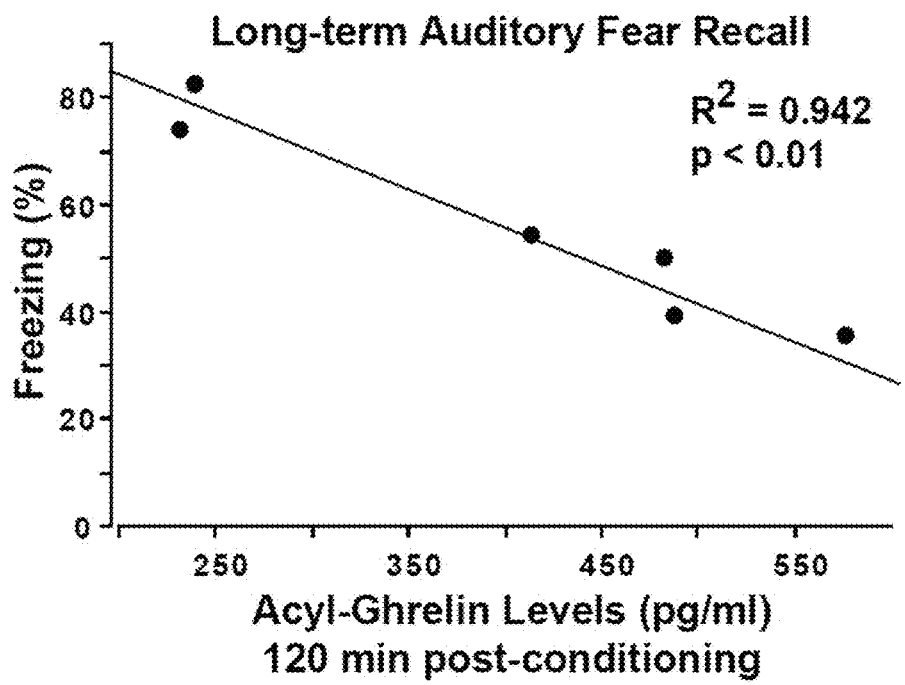
FIGS. 5A-F show acyl-ghrelin levels around the time of fear conditioning do not predict fear levels during conditioning or long-term context fear recall. The best fit lines from a linear regression of freezing (%) predicted by ghrelin levels (pg/ml) at 120 minutes (FIG. 5A) and 180 minutes (FIG. 5B) after fear conditioning. At 120 minutes, the coefficient for ghrelin level was −0.12, p-value for the coefficient was 0.001, the intercept was 108 pg/ml, r-squared was 0.94, root mean squared error (RMSE) was 5.0, and the predicted residual sum of squares (PRESS) statistic was 251. At 180 minutes, the coefficient for ghrelin level was −0.11, p-value for the coefficient was 0.002, the intercept was 99.2 pg/ml, r-squared was 0.93, RMSE was 5.7, and the PRESS statistic was 335. Linear regression results for all time points are presented in Table 1.
Figure 5B:
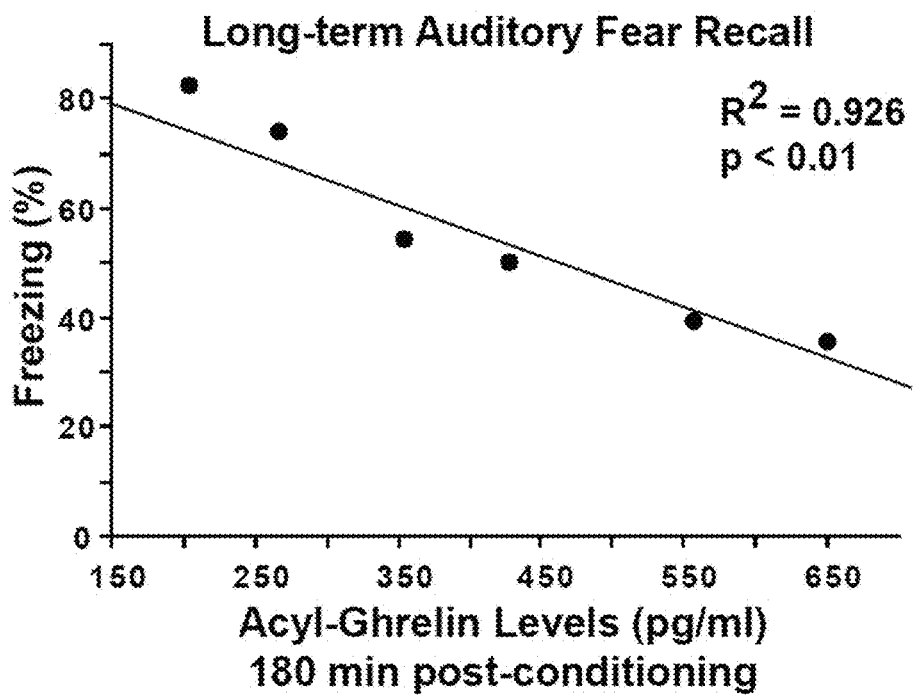
Figure 5C:
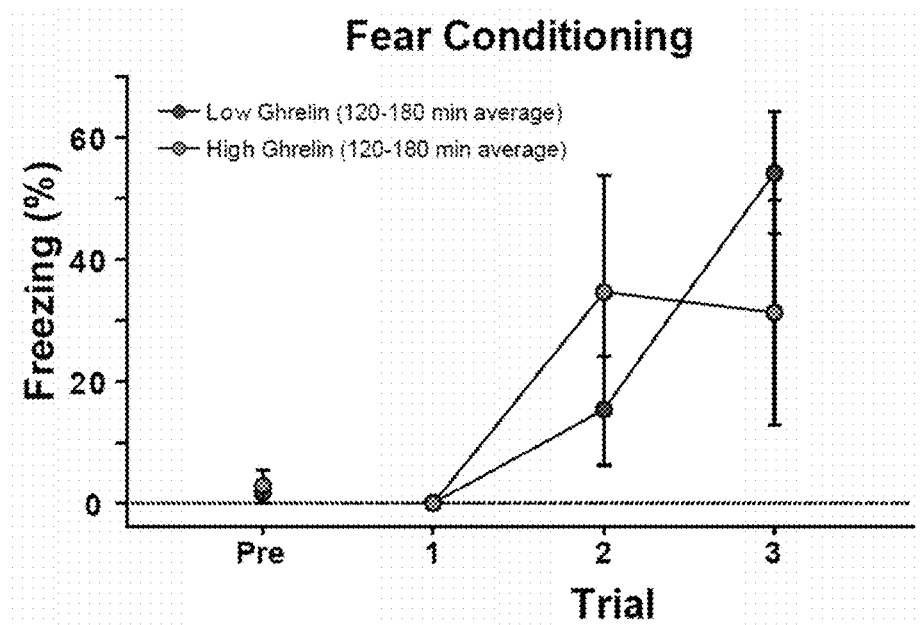
Figure 5D:
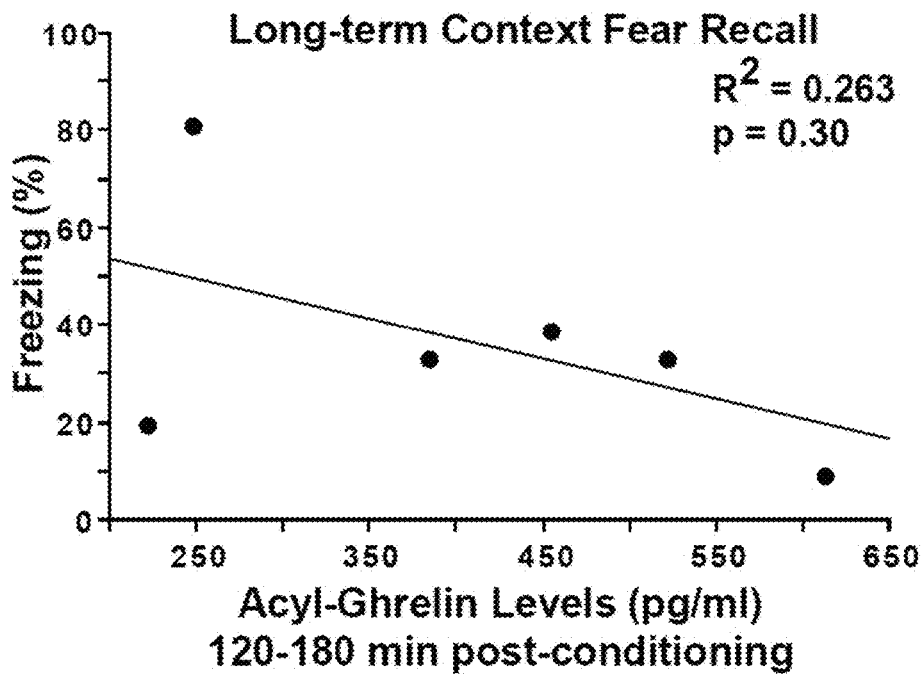
Figure 6A:
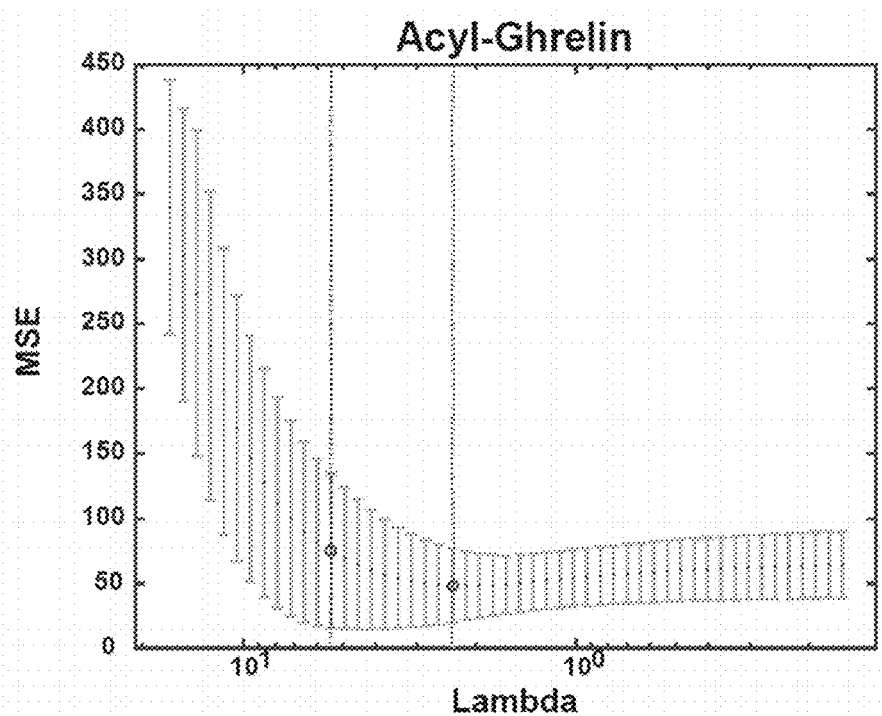
FIGS. 6A-B shows iterations of the Lasso technique. For all iterations of the lasso algorithm for ghrelin levels (FIG. 6A) and corticosterone levels (FIG. 6B), mean squared error (MSE) is plotted against lambda. Lambda is the regularization constant for the algorithm; as lambda increases, the regression is more regularized, such that the algorithm penalizes overfitting more heavily and the resulting model is more likely to generalize to independent data sets. The rightmost dotted line indicates the value of lambda with the minimum MSE for predicting freezing. The leftmost dotted line indicates the most regularized regression having an MSE within one standard deviation of the minimum MSE; this is a heuristic method for choosing the optimal stopping point of the lasso algorithm.
Figure 6B:
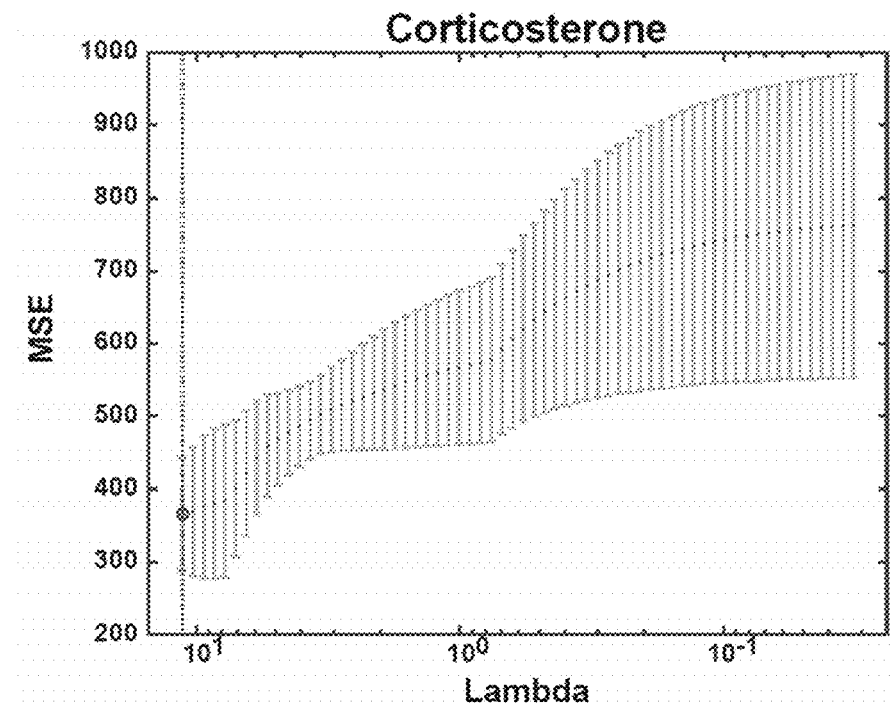

Acyl-ghrelin levels measured at 120 or 180 minutes after fear conditioning each individually accounted for a substantial amount of the variance in freezing behavior (FIGS. 5A-B and Table 1). This was confirmed with Lasso regression (see Materials and Methods, FIG. 6A): the best-fitting linear model included acyl-ghrelin levels at both 120 and 180 minutes after fear conditioning (FIG. 1C). Higher levels of endogenous circulating ghrelin across these time points robustly constrained auditory fear memory strength. Despite a substantial literature implicating glucocorticoids in memory formation[13], none of the selected models retained corticosterone levels as a measurement to explain freezing behavior (FIG. 6B, Table 1). The differences in auditory fear memory recall between rats with relatively high circulating acyl-ghrelin levels (FIG. 1D, light gray) and those with relatively low circulating acyl-ghrelin levels (FIG. 1D, dark gray) persisted across the auditory fear extinction test, and were not observed during fear conditioning itself (FIG. 5C) or during long-term context fear memory recall (FIG. 5D). Because post-conditioning acyl-ghrelin levels specifically predict long-term auditory fear memory but not fear acquisition, this suggests that endogenous acyl-ghrelin negatively regulates fear memory consolidation.

The Lasso results indicate that measurement of corticosterone levels did not predict freezing levels better an intercept term alone, in this data set. The positive and weak correlation between corticosterone levels long-term auditory fear memory strength was not statistically significant at any time point (Table 1). Corticosterone explained a similar proportion of behavioral variability as has been reported in other studies[29-31], but variation in acyl-ghrelin levels alone accounted for the majority of the individual variability in fear memory, even though ghrelin levels were not altered by an aversive, stressful experience.

TABLE 1

Results of twelve univariate linear regressions, of freezing (%) predicted by ghrelin and corticosterone levels at minutes after fear conditioning = [0 30 60 120 180]. RMSE is the root mean squared error of the regression. PRESS is the predicted residual sum of squares statistic. Starred p-values indicate coefficients for hormone levels that are significantly different from zero.

| | Minutes after Fear Conditioning | | | | | |
|---|---|---|---|---|---|---|
| Ghrelin | 0 | 10 | 30 | 60 | 120 | 180 |
| $r^2$ | 0.00 | 0.57 | 0.09 | 0.06 | 0.94 | 0.93 |
| P-value | 0.96 | 0.08 | 0.55 | 0.62 | 0.001* | 0.002* |
| RMSE | 20.9 | 13.7 | 19.9 | 12.9 | 550 | 5.7 |
| PRESS | 3993 | 1661 | 3765 | 1257 | 251 | 335 |

| | Minutes after Fear Conditioning | | | | | |
|---|---|---|---|---|---|---|
| CORT | 0 | 10 | 30 | 60 | 120 | 180 |
| $r^2$ | 0.43 | 0.34 | 0.35 | 0.04 | 0.18 | 0.07 |
| p-value | 0.15 | 0.22 | 0.21 | 0.70 | 0.40 | 0.61 |
| RMSE | 15.7 | 17.0 | 16.9 | 20.5 | 19.0 | 20.2 |
| PRESS | 2264 | 1851 | 2499 | 3439 | 2473 | 6520 |

Figure 1E:
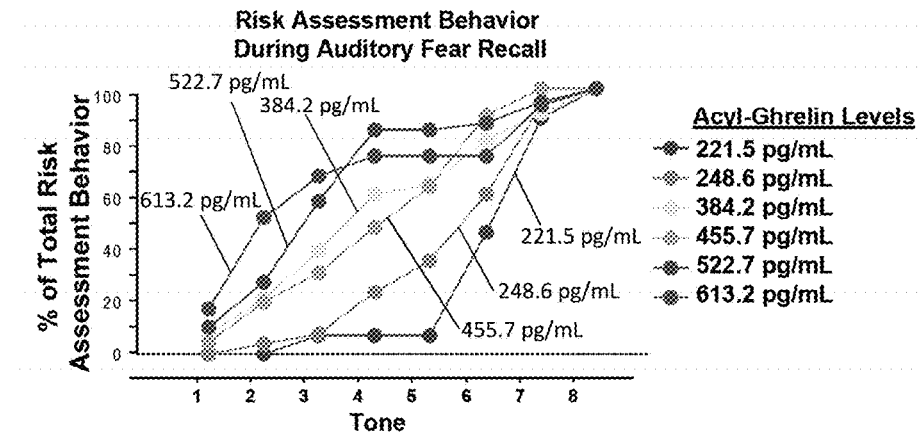
Figure 5E:
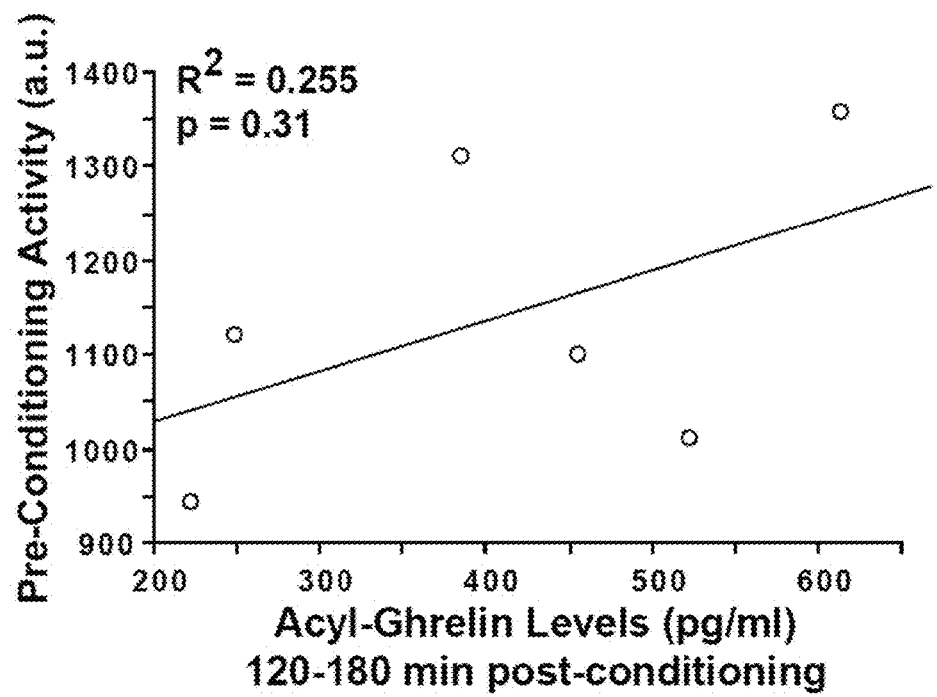

It could be argued that hunger and fear are incompatible states and thus compete with each other within neural circuits. Freezing behavior, in particular, will prevent an organism from locating food. Such a hunger/aversive behavior tradeoff has been described for a specialized subset of hypothalamic neurons[14]. By this logic, high levels of acyl-ghrelin, which under some circumstances can promote hunger[15], may also facilitate exploration to increase the opportunity to find food. For example, increasing levels of acyl-ghrelin might facilitate motor hyperactivity, thereby decreasing freezing behavior. However, no correlations were observed between gross motor activity and acyl-ghrelin levels across individuals (FIG. 5E). Instead, it was found that higher levels of acyl-ghrelin were associated with earlier onset of risk assessment behavior during the long-term auditory fear recall test (FIG. 1E). Risk assessment is a specific behavioral indicator of low, but not high, fear states[16], and no risk assessment behavior was observed in any rat prior to the tone onset of each fear recall test (data not shown), confirming that this behavior is specifically elicited during a fear state. Thus, rats with higher endogenous acyl-ghrelin levels more rapidly transition to a low fear state during the fear recall test. Collectively, these data show that acyl-ghrelin levels are related to the strength of fear memories, rather than motor hyperactivity.

Figure 5F:
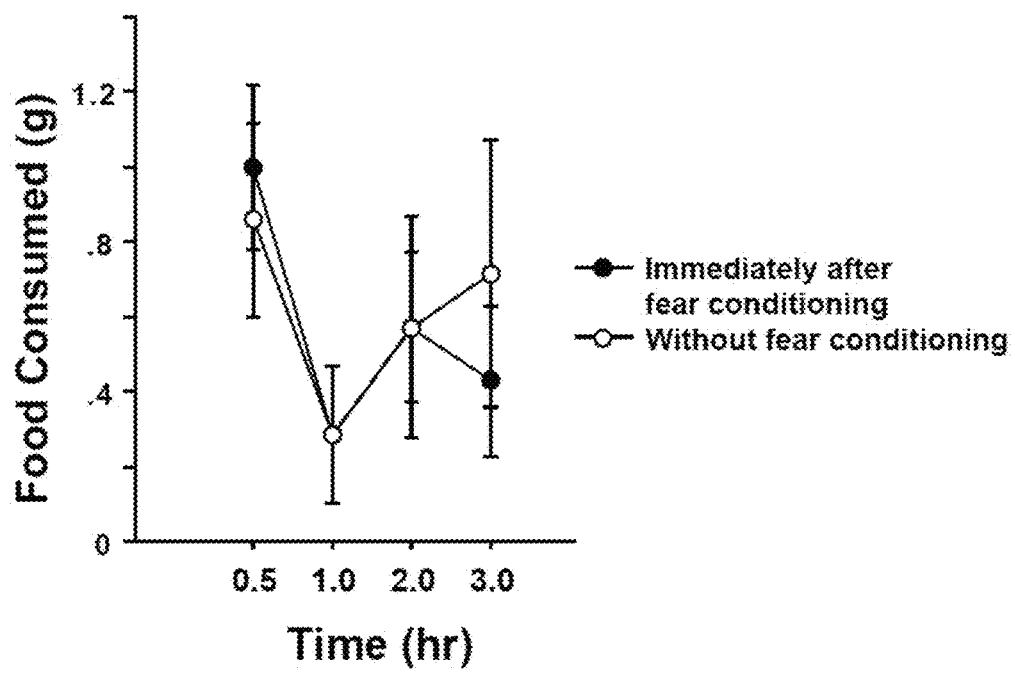

Because ghrelin can be elevated by hunger[17], it might be hypothesized that inter-individual variability in acyl-ghrelin arises when fear conditioning suppresses post-conditioning food consumption to different degrees in individuals in the hours following conditioning. However, in addition to finding that acyl-ghrelin levels remain similar before and after fear conditioning (FIG. 1B), it was found that fear conditioning does not suppress food consumption (FIG. 5F). Thus, it was hypothesized that baseline ghrelin levels are a stable and variable individual trait over time. Because post-conditioning ghrelin levels were negatively correlated with long-term fear memory, and fear conditioning did not substantially alter acyl-ghrelin levels (FIG. 1B), it was further hypothesized that pre-conditioning acyl-ghrelin levels would also correlate with fear memory. To assess this, a second experiment was conducted in which circulating acyl-ghrelin levels in unoperated, unstressed rats were measured at least one week prior to auditory Pavlovian fear conditioning (FIG. 2A). The finding that acyl-ghrelin levels are strongly and negatively associated with long-term auditory fear memory was replicated (FIG. 2B). This suggests that measuring acyl-ghrelin levels prior to an aversive experience might be used as a predictive biomarker for long-term fear memory strength.

Figure 3A:
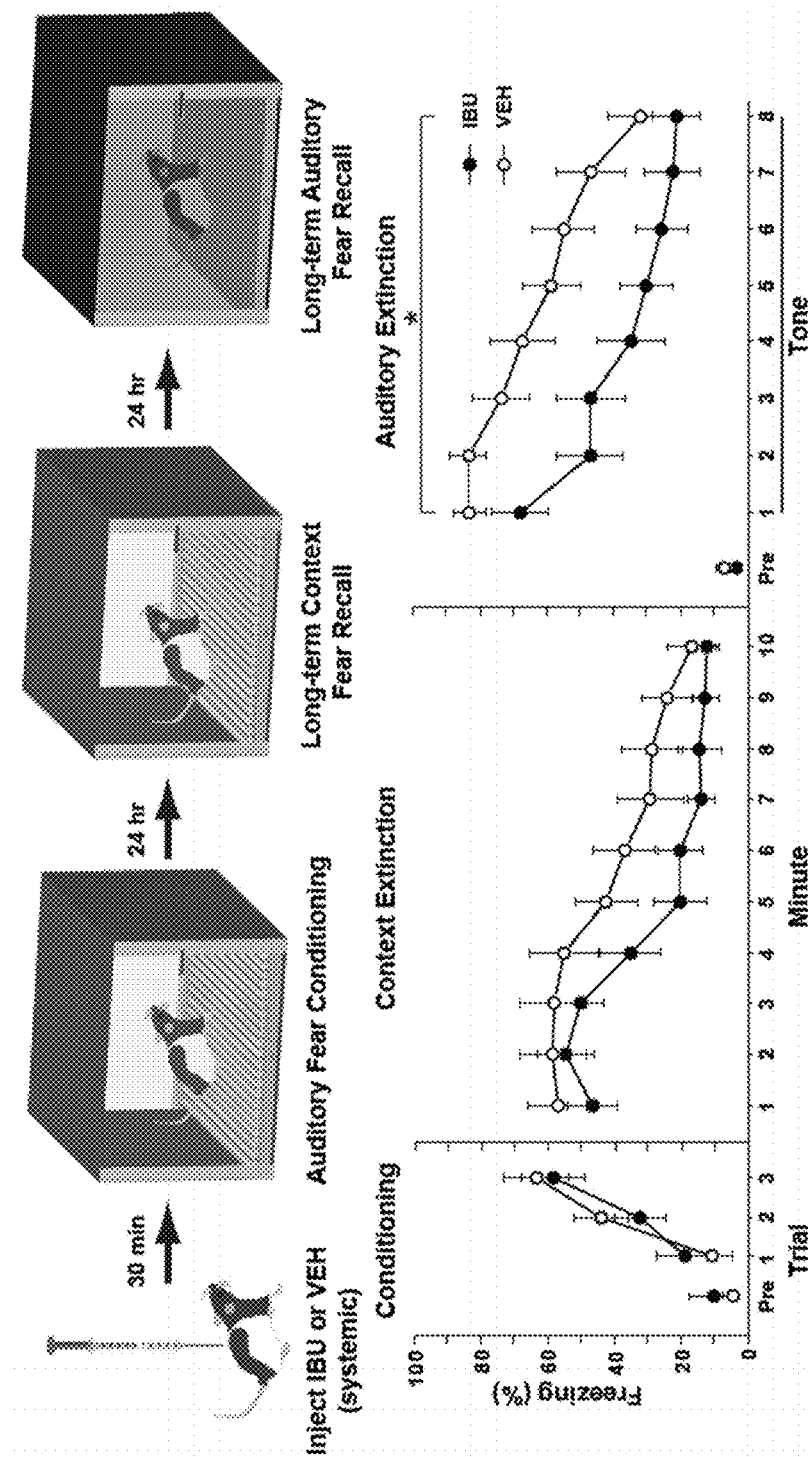
FIGS. 3A-D show the enhanced effects of endogenous ghrelin further constrain fear memory strength.
Figure 3B:
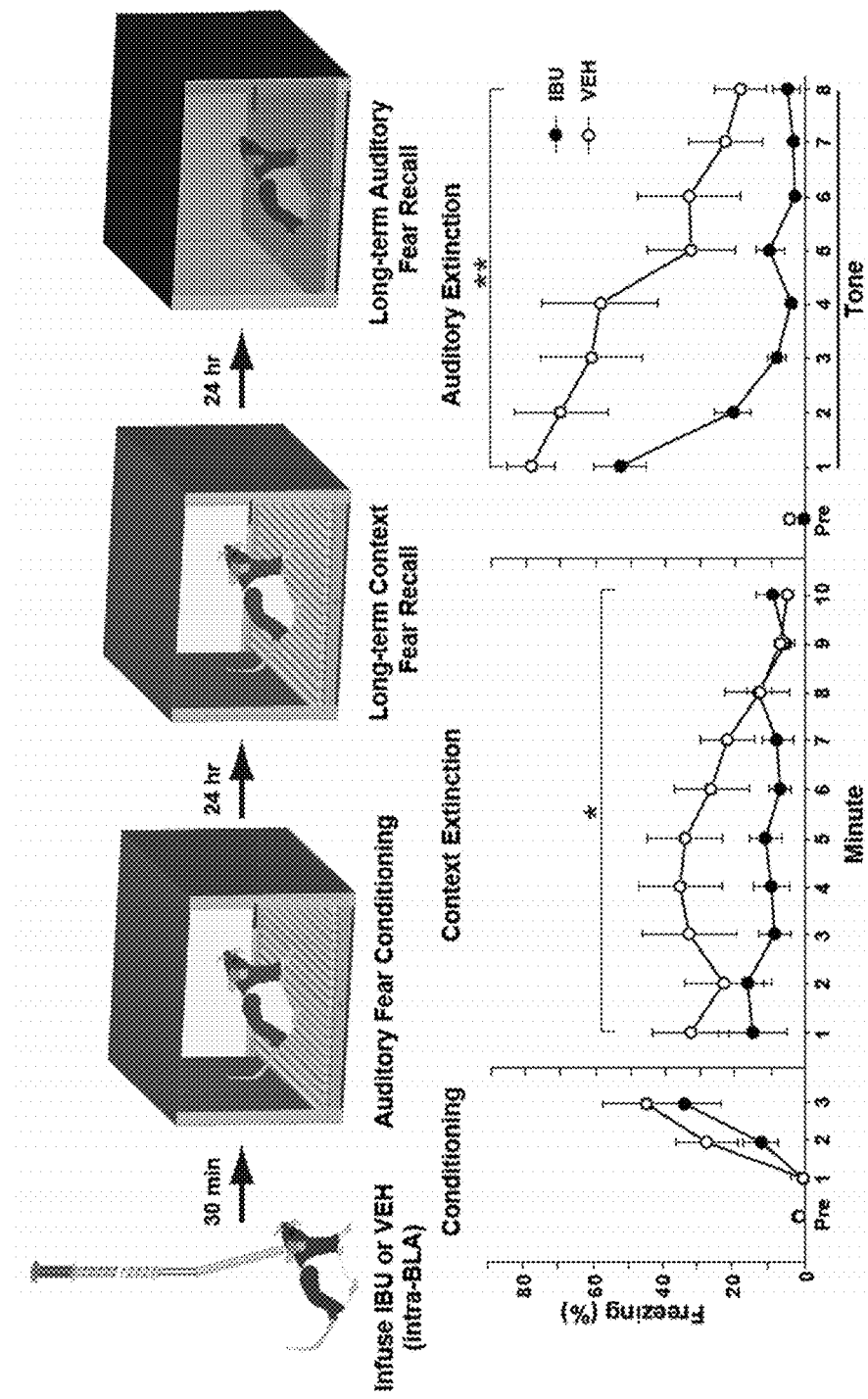
Figure 3C:
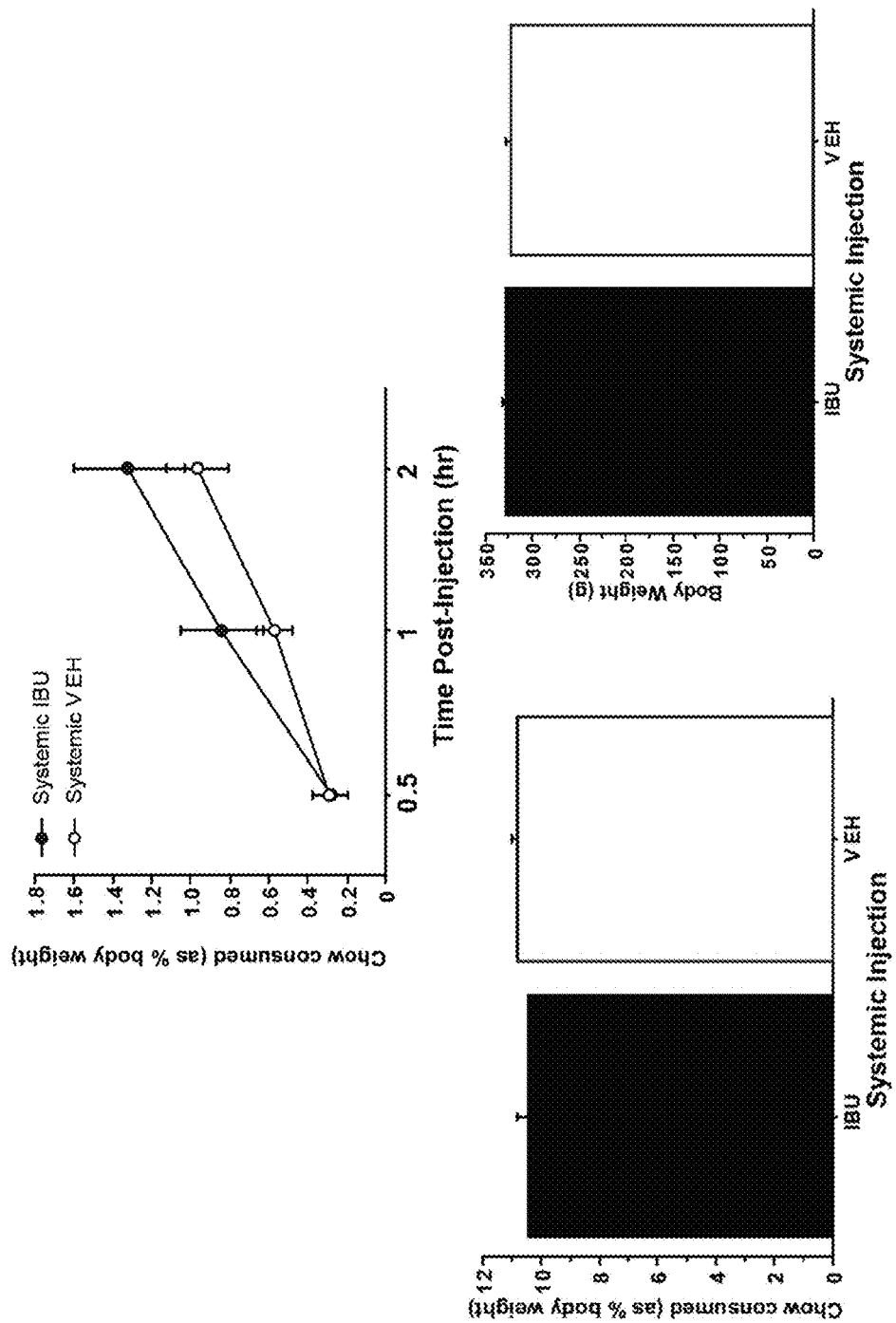
Figure 3D:
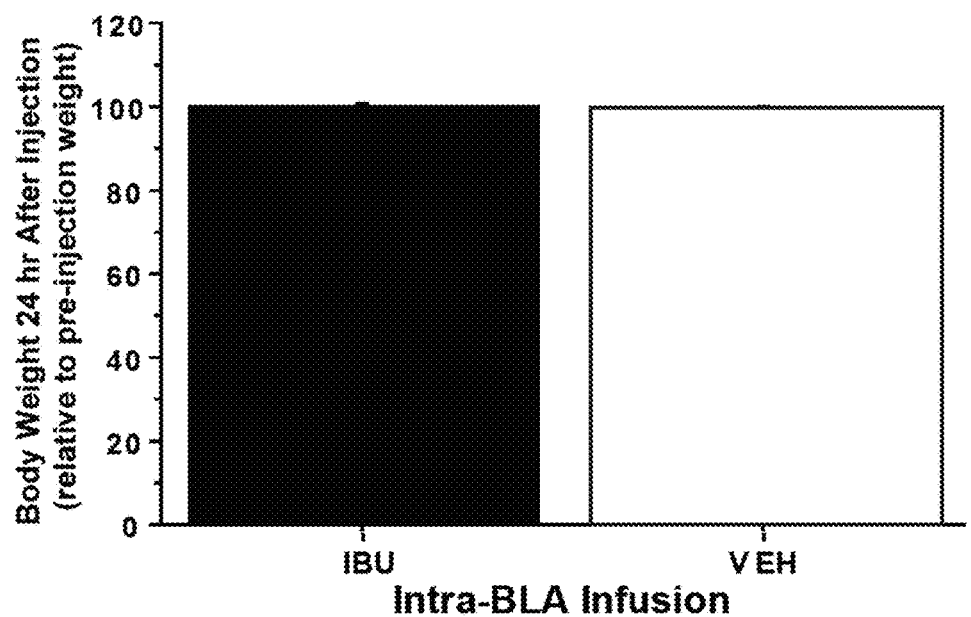
Figure 7A:
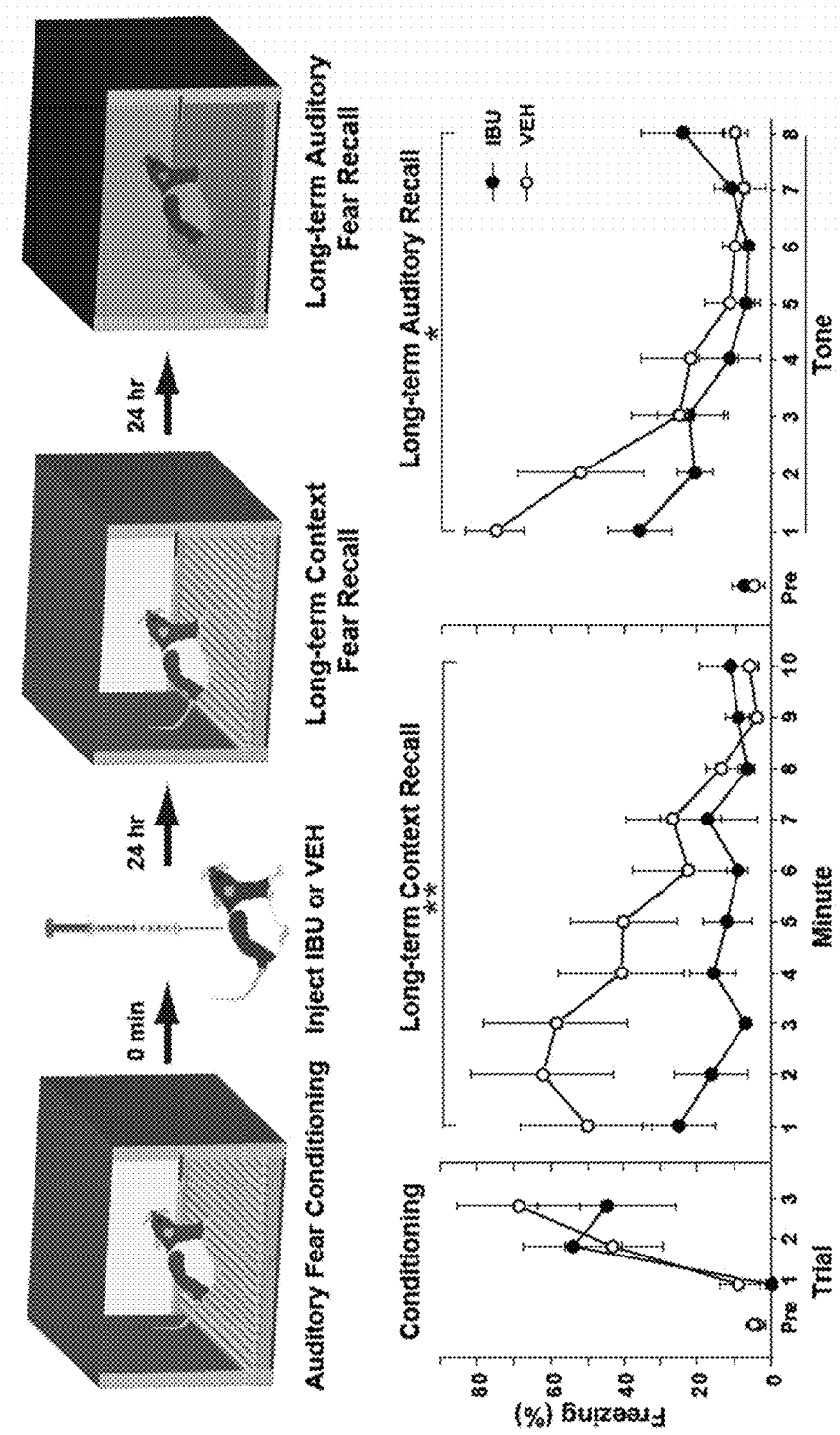
FIGS. 7A-B show the effects of systematic administration of a ghrelin receptor antagonist at different doses.
Figure 7B:
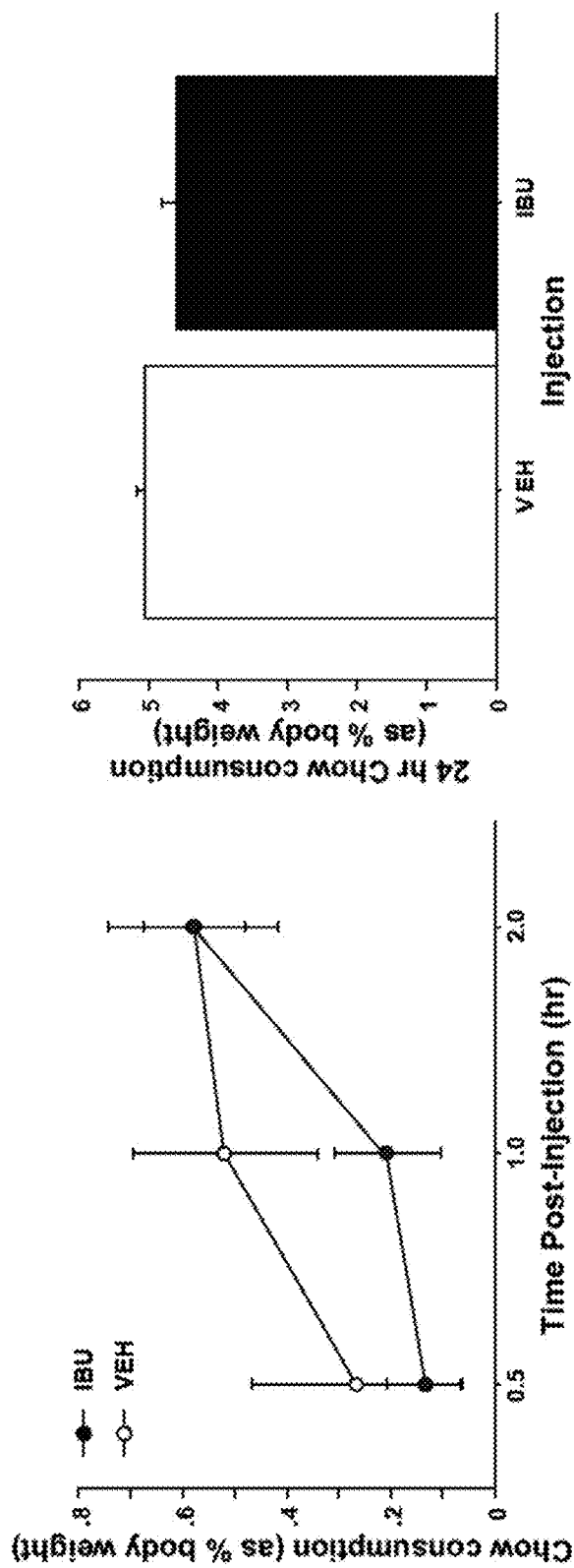

Because enhanced consolidation of fearful memories is thought to underlie the development of some trauma and stress-related disorders such as post-traumatic stress disorder (PTSD), interventions that reduce the consolidation of fear memories represent a promising strategy to prevent the development of these disorders[18]. Harnessing the power of an endogenous fear-inhibitory system such as ghrelin is especially promising because both ghrelin and pharmacological ghrelin receptor agonists have strong safety profiles in human subjects[19-22]. To determine whether fear memories can be further inhibited by artificially boosting the effects of endogenous acyl-ghrelin, ibutamoren mesylate (IBU), a pharmacological ghrelin receptor agonist[19], or vehicle (VEH) was administered 30 minutes prior to auditory Pavlovian fear conditioning (FIG. 3A, upper panel). The systemic administration of IBU produced significantly lower levels of long-term auditory fear memory without impacting fear acquisition or long-term contextual memory (FIG. 3A, lower panel). Similar results were observed when IBU was injected immediately following auditory fear conditioning (FIGS. 7A-B) or when IBU was infused directly into the BLA (FIG. 3B, lower panel): both long-term contextual and auditory fear memory were strongly inhibited, without any effect on fear acquisition. Critically, the ghrelin receptor agonist used here did not stimulate hunger or change body weight within the 24 hours after injection (FIGS. 3C-D), even when administered at a dose twenty times higher than was used to inhibit fear (FIG. 7B). Collectively, these results show that signaling through the ghrelin receptor during the memory consolidation period is critical for regulating fear memory strength, and also that the BLA is a critical site by which systemic ghrelin receptor agonists can inhibit fear memory consolidation.

Figure 4A:
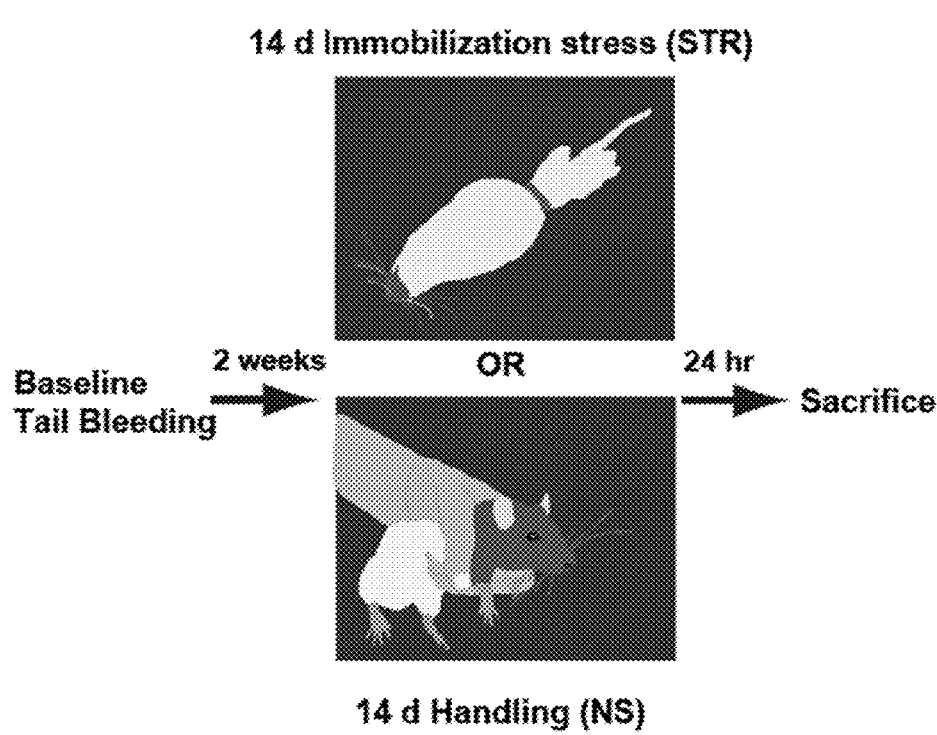
FIGS. 4A-F show chronic stress decreases ghrelin binding in the amygdala and renders animals insensitive to the fear-reducing effects of a ghrelin receptor agonist.
Figure 4B:
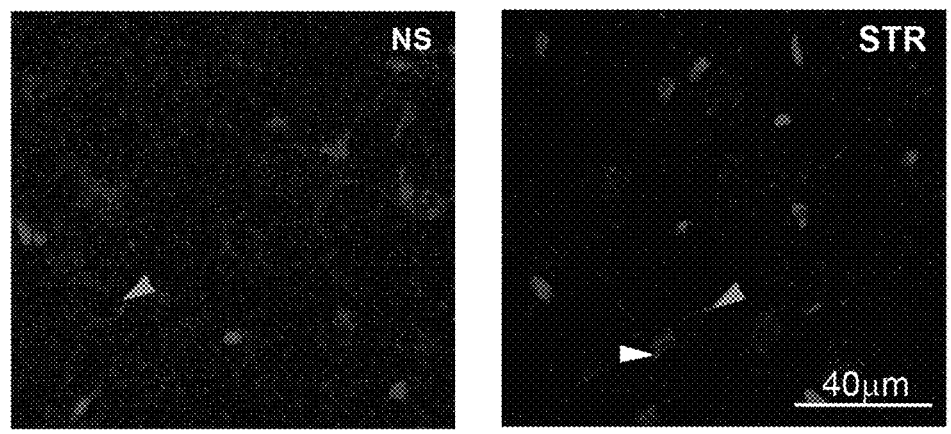
Figure 4C:
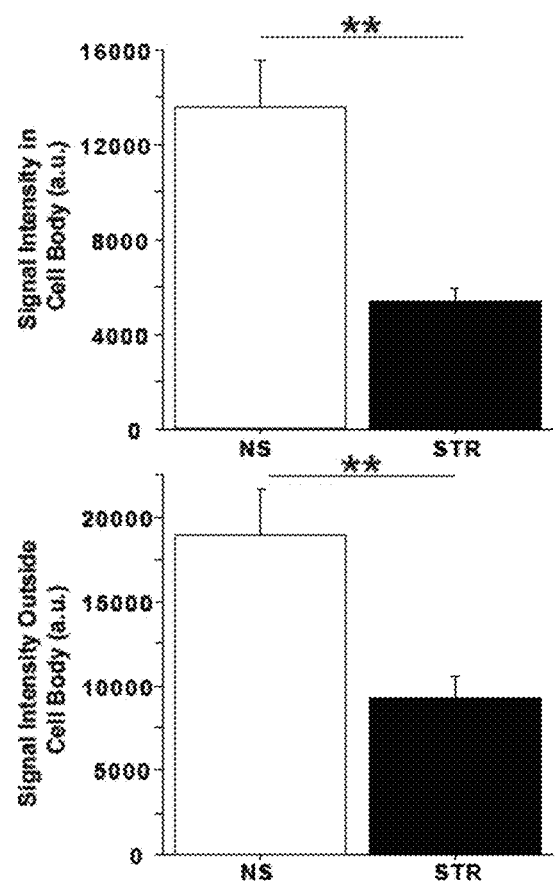
Figure 4D:
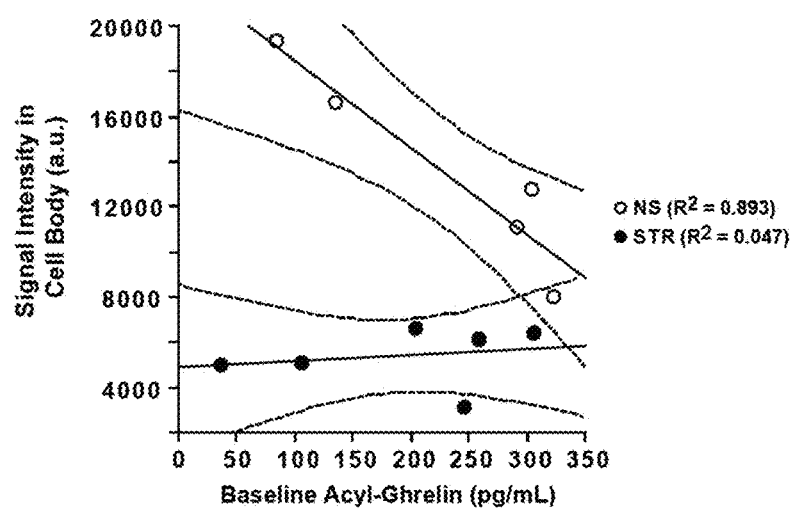

It is surprising that higher levels of GHSR signaling are associated with weaker fear memories. In rats exposed to chronic stress, elevated acyl-ghrelin[23] causes enhanced fear memory formation[10], whereas here, it is shown that in unstressed rats, higher levels of acyl-ghrelin are associated with weaker fear memories. Similar opposing effects of ghrelin have been noted for anxiety[24], a different form of aversive behavior, but the mechanism by which this occurs remains unknown. To explain the paradoxical effects of ghrelin in unstressed versus chronically stressed rodents, it was hypothesized that stress-induced elevation of acyl-ghrelin promotes central ghrelin resistance, where cells compensate for stress-induced upregulation of signaling through ghrelin-mediated pathways by downregulating expression of the ghrelin receptor. To assess this, rats were sacrificed one day following the last day of a two week period of either chronic immobilization stress or handling (FIG. 4A). Binding sites for acyl-ghrelin in the BLA were identified with biotin-labeled acyl-ghrelin in coronal brain sections (FIG. 4B); signal was absent in sections incubated without biotin-labeled acyl-ghrelin (FIG. 8). Ghrelin binding sites were dramatically downregulated in the BLA of stressed rats compared to that of unstressed rats (FIG. 4C). In unstressed rats, the availability of ghrelin binding sites exhibited a strong negative correlation with endogenous acyl-ghrelin levels measured 15 days prior to sacrifice (FIG. 4D); this correlation was lost in stressed rats, who exhibited levels of ghrelin binding sites that were uniformly lower than those observed in unstressed rats (FIG. 4D). These findings show that chronic stress produces ghrelin resistance in the BLA and provide a specific mechanism (loss of ghrelin receptor) by which this occurs. The study is the first to report a specific mechanism for central ghrelin resistance following high circulating acyl-ghrelin levels.

Figure 4E:
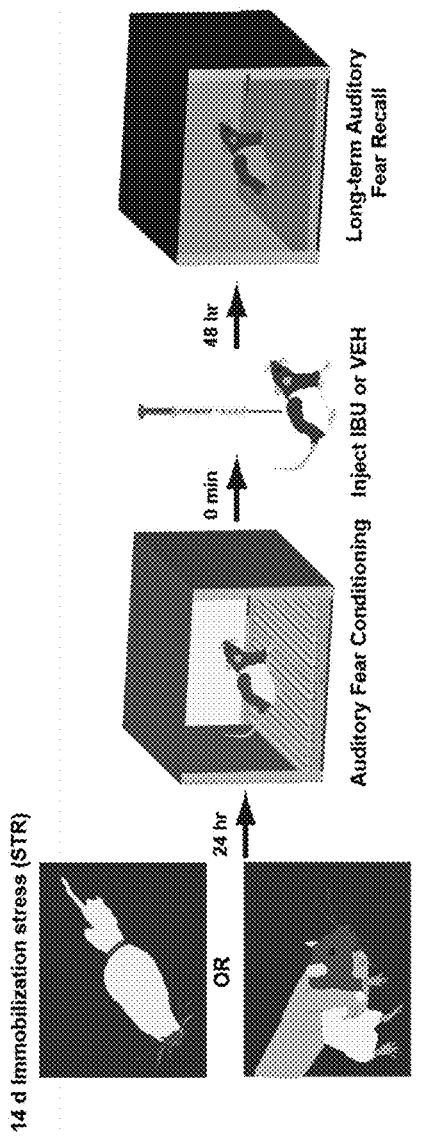
Figure 4F:
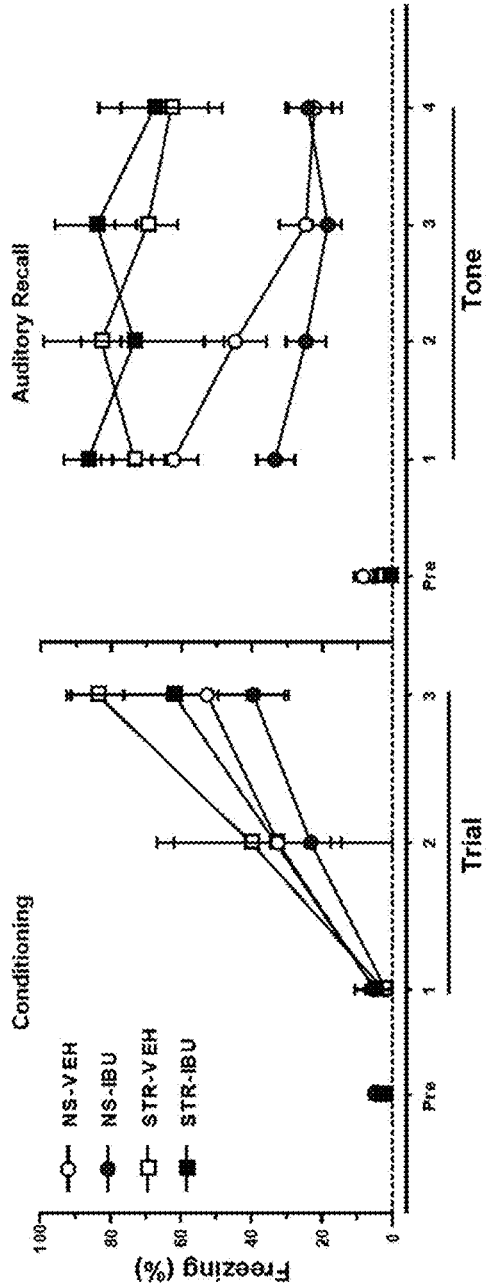

To determine whether the decrease in ghrelin binding sites in the BLA of chronically stressed rats exerts a functional impact, rats received either chronic immobilization stress or handling for two weeks followed by auditory fear conditioning (FIG. 4E). IBU, at the dose shown to reduce fear memory strength in unstressed rats (FIGS. 3A-D), or VEH was injected immediately after conditioning and long-term auditory fear memory was assessed two days later. While IBU reduced long-term auditory fear memory in unstressed rats, it had no effect on conditional freezing in stressed rats (FIG. 4F), supporting the idea that chronic stress promotes functional ghrelin resistance. These findings strongly support the idea that the excessive fear observed in chronically stressed rats, who also have high circulating ghrelin levels[10], likely arises, in part, from stress-induced loss of an inhibitory signal in the BLA.

The powerful correlation between individual levels of circulating ghrelin and long-term fear memory reported here is unexpected. While amygdala activity in humans at the time of emotional memory encoding has a strong correlation with subsequent long-term memory strength[27] no stress hormone has been shown to be a negative regulator of long-term fear memory strength. Interestingly, post-training levels of norepinephrine in the BLA show considerable variability across individuals and are a strong positive predictor of long-term aversive memory strength[28]. Thus, while norepinephrine accelerates the consolidation of aversive memory and confers susceptibility to "over-consolidation" of aversive experiences, ghrelin provides a previously unrecognized opposing force which confers resilience to the overconsolidation of aversive experiences. Post-training glucocorticoid levels do modulate fear memory strength[29-31], an effect replicated here, but the predictive power of ghrelin is significantly greater.

Figure 9:
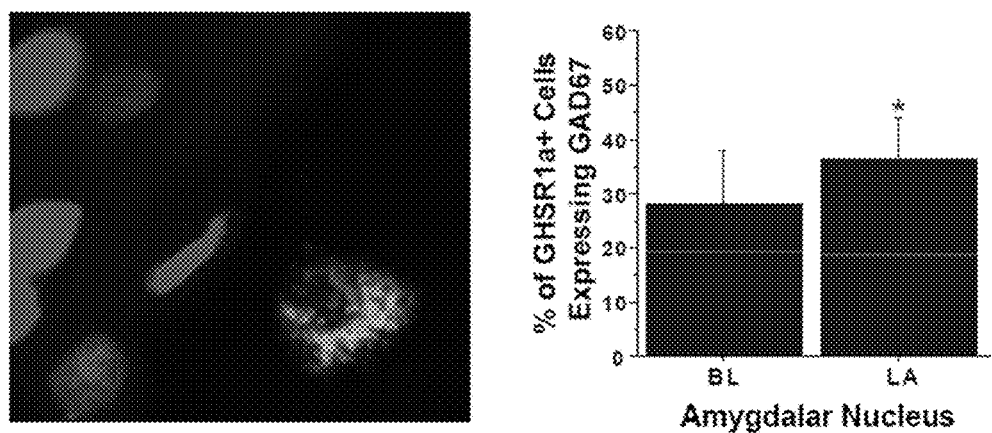
FIG. 9 shows ghrelin receptors are expressed in inhibitory interneurons in the amygdala.

It is also notable that ghrelin constrains memory consolidation and reduces fear memory strength, because it may have the opposite effect on hippocampus-dependent memory consolidation[32]. Indeed, transient elevation of ghrelin enhances glutamatergic neurotransmission and plasticity in hippocampus[32,33]. It is unclear why ghrelin-mediated signaling in the amygdala favors the reduction, rather than the enhancement, of fear memory. There are several potential mechanisms by which this could occur, including ghrelin-mediated excitation of inhibitory interneurons (FIG. 9), ghrelin-mediated excitation of glutamatergic projection neurons in the BLA that selectively inhibit fear memories[34], and recruitment of inhibitory G protein-mediated signaling cascades[35]. Future work will undoubtedly dissect the contribution of these complex mechanisms. Regardless of the mechanism by which ghrelin regulates memory consolidation, these findings contribute to an emerging literature supporting the idea that a neuromodulator may have very different effects on plasticity in different neural circuits.

It may seem counterintuitive that ghrelin modulates fear memory consolidation independent of a role in hunger or appetitive processing because ghrelin is a hunger hormone and hunger can exert potent influences on emotional tone[14,36]. However, it is important to note that endogenous acyl-ghrelin signals hunger as a large, acute spike over "background" acyl-ghrelin levels[4,37]. This suggests that hypothalamic hunger circuits are relatively insensitive to acyl-ghrelin, as large spikes in acyl-ghrelin are required to drive the subjective feeling of hunger. In contrast, reported here is that the ability of the BLA to modulate fear memory consolidation is sensitive to tonic, background levels of acyl-ghrelin. Here, it is shown that these levels of ghrelin have a powerful correlation with fear memory strength without impacting exploratory behavior, food consumption or body weight.

A few previous studies have examined the role of ghrelin in fear-related tasks, but these are difficult to directly compare to the findings here. In one study, intra-amygdala infusions of ghrelin were shown to enhance avoidance memory[38], seeming to conflict with the observations reported here. However this study targeted the central nucleus of the amygdala and the species of ghrelin was not indicated. Additionally, the surgical procedure to implant cannulae in the brain might have served as a chronic stressor which induced the loss of ghrelin-mediated inhibition in the amygdala. In a different study, transgenic mice with a knockout of the ghrelin 1a receptor exhibited a selective impairment in contextual fear memory levels measured one month after fear conditioning[39]. One potential caveat to interpreting these findings is that the developmental knockout may have led to compensation in ghrelin receptor-expressing brain regions such as the BLA. Additionally, it is not clear what memory-related process was affected, and thus what brain regions might be implicated. For example, the deficit in contextual fear at 30 days after the first extinction session could reflect enhanced fear extinction in the ghrelin knockout mice, or impaired fear incubation. Without further data, these findings are difficult to interpret in light of the present results. Results presented here are powerful because endogenous circulating levels of acyl-ghrelin were examined to reveal the relationship to fear memory strength.

REFERENCES

1. Kojima M, Hosoda H, Date Y, Nakazato M, Matsuo H, Kangawa K. Ghrelin is a growth-hormone-releasing acylated peptide from stomach. Nature 1999; 402(6762): 656-660.
2. Bednarek M A, Feighner S D, Pong S S, McKee K K, Hreniuk D L, Silva M V et al. Structure-function studies on the new growth hormone-releasing peptide, ghrelin:

minimal sequence of ghrelin necessary for activation of growth hormone secretagogue receptor 1a. J Med Chem 2000; 43(23): 4370-4376.
3. Guan X M, Yu H, Palyha O C, McKee K K, Feighner S D, Sirinathsinghji D J et al. Distribution of mRNA encoding the growth hormone secretagogue receptor in brain and peripheral tissues. Brain Res Mol Brain Res 1997; 48(1): 23-29.
4. Cummings D E, Purnell J Q, Frayo R S, Schmidova K, Wisse B E, Weigle D S. A preprandial rise in plasma ghrelin levels suggests a role in meal initiation in humans. Diabetes 2001; 50(8): 1714-1719.
5. Wren A M, Seal L J, Cohen M A, Brynes A E, Frost G S, Murphy K G et al. Ghrelin enhances appetite and increases food intake in humans. J Clin Endocrinol Metab 2001; 86(12): 5992.
6. Alvarez-Crespo M, Skibicka K P, Farkas I, Molnar C S, Egecioglu E, Hrabovszky E et al. The amygdala as a neurobiological target for ghrelin in rats: neuroanatomical, electrophysiological and behavioral evidence. PLoS One 2012; 7(10): e46321.
7. Kumar J, Chuang J C, Na E S, Kuperman A, Gillman A G, Mukherjee S et al. Differential effects of chronic social stress and fluoxetine on meal patterns in mice. Appetite 2013; 64: 81-88.
8. Song L, Zhu Q, Liu T, Yu M, Xiao K, Kong Q et al. Ghrelin modulates lateral amygdala neuronal firing and blocks acquisition for conditioned taste aversion. PLoS One 2013; 8(6): e65422.
9. Carlini V P, Monzon M E, Varas M M, Cragnolini A B, Schioth H B, Scimonelli T N et al. Ghrelin increases anxiety-like behavior and memory retention in rats. Biochem Biophys Res Commun 2002; 299(5): 739-743.
10. Meyer R M, Burgos-Robles A, Liu E, Correia S S, Goosens K A. A ghrelin-growth hormone axis drives stress-induced vulnerability to enhanced fear. Mol Psychiatry 2013.
11. Cowley M A, Smith R G, Diano S, Tschop M, Pronchuk N, Grove K L et al. The distribution and mechanism of action of ghrelin in the CNS demonstrates a novel hypothalamic circuit regulating energy homeostasis. Neuron 2003; 37(4): 649-661.
12. Dudai Y. The neurobiology of consolidations, or, how stable is the engram? Annu Rev Psychol 2004; 55: 51-86.
13. Finsterwald C, Alberini C M. Stress and glucocorticoid receptor-dependent mechanisms in long-term memory: from adaptive responses to psychopathologies. Neurobiol Learn Mem 2014; 112: 17-29.
14. Dietrich M O, Zimmer M R, Bober J, Horvath T L. Hypothalamic Agrp neurons drive stereotypic behaviors beyond feeding. Cell 2015; 160(6): 1222-1232.
15. Tschop M, Smiley D L, Heiman M L. Ghrelin induces adiposity in rodents. Nature 2000; 407(6806): 908-913.
16. Harrison L A, Ahn C, Adolphs R. Exploring the Structure of Human Defensive Responses from Judgments of Threat Scenarios. PLoS One 2015; 10(8): e0133682.
17. Natalucci G, Riedl S, Gleiss A, Zidek T, Frisch H. Spontaneous 24-h ghrelin secretion pattern in fasting subjects: maintenance of a meal-related pattern. Eur J Endocrinol 2005; 152(6): 845-850.
18. Parsons R G, Ressler K J. Implications of memory modulation for post-traumatic stress and fear disorders. Nat Neurosci 2013; 16(2): 146-153.
19. Nass R, Pezzoli S S, Oliveri M C, Patrie J T, Harrell F E, Jr., Clasey J L et al. Effects of an oral ghrelin mimetic on body composition and clinical outcomes in healthy older adults: a randomized trial. Ann Intern Med 2008; 149(9): 601-611.
20. Codner E, Cassorla F, Tiulpakov A N, Mericq M V, Avila A, Pescovitz O H et al. Effects of oral administration of ibutamoren mesylate, a nonpeptide growth hormone secretagogue, on the growth hormone-insulin-like growth factor I axis in growth hormone-deficient children. Clin Pharmacol Ther 2001; 70(1): 91-98.
21. Goldstone A P, Prechtl C G, Scholtz S, Miras A D, Chhina N, Durighel G et al. Ghrelin mimics fasting to enhance human hedonic, orbitofrontal cortex, and hippocampal responses to food. Am J Clin Nutr 2014; 99(6): 1319-1330.
22. Garin M C, Burns C M, Kaul S, Cappola A R. Clinical review: The human experience with ghrelin administration. J Clin Endocrinol Metab 2013; 98(5): 1826-1837.
23. Lutter M, Sakata I, Osborne-Lawrence S, Rovinsky S A, Anderson J G, Jung S et al. The orexigenic hormone ghrelin defends against depressive symptoms of chronic stress. Nat Neurosci 2008; 11(7): 752-753.
24. Spencer S J, Emmerzaal T L, Kozicz T, Andrews Z B. Ghrelin's Role in the Hypothalamic-Pituitary-Adrenal Axis Stress Response: Implications for Mood Disorders. Biol Psychiatry 2015; 78(1): 19-27.
25. Lockie S H, Dinan T, Lawrence A J, Spencer S J, Andrews Z B. Diet-induced obesity 456 causes ghrelin resistance in reward processing tasks. Psychoneuroendocrinology 2015; 457 62: 114-120.
26. Briggs D I, Lockie S H, Benzler J, Wu Q, Stark R, Reichenbach A et al. Evidence that diet-induced hyperleptinemia, but not hypothalamic gliosis, causes ghrelin resistance in NPY/AgRP neurons of male mice. Endocrinology 2014; 155(7): 2411-2422.
27. Cahill L, Haler R J, Fallon J, Alkire M T, Tang C, Keator D et al. Amygdala activity at encoding correlated with long-term, free recall of emotional information. Proc Natl Acad Sci USA 1996; 93(15): 8016-8021.
28. McIntyre C K, Hatfield T, McGaugh J L. Amygdala norepinephrine levels after training predict inhibitory avoidance retention performance in rats. Eur J Neurosci 2002; 16(7): 1223-1226.
29. Hui G K, Figueroa I R, Poytress B S, Roozendaal B, McGaugh J L, Weinberger N M. Memory enhancement of classical fear conditioning by post-training injections of corticosterone in rats. Neurobiol Learn Mem 2004; 81(1): 67-74.
30. Cordero M I, Sandi C. A role for brain glucocorticoid receptors in contextual fear conditioning: dependence upon training intensity. Brain Res 1998; 786(1-2): 11-17.
31. Marin M F, Hupbach A, Maheu F S, Nader K, Lupien S J. Metyrapone administration reduces the strength of an emotional memory trace in a long-lasting manner. J Clin Endocrinol Metab 2011; 96(8): E1221-1227.
32. Ghersi M S, Gabach L A, Buteler F, Vilcaes A A, Schioth H B, Perez M F et al. Ghrelin increases memory consolidation through hippocampal mechanisms dependent on glutamate release and NR2B-subunits of the NMDA receptor. Psychopharmacology (Berl) 2014.
33. Ribeiro L F, Catarino T, Santos S D, Benoist M, van Leeuwen J F, Esteban J A et al. Ghrelin triggers the synaptic incorporation of AMPA receptors in the hippocampus. Proc Natl Acad Sci USA 2014; 111(1): E149-158.
34. Jasnow A M, Ehrlich D E, Choi D C, Dabrowska J, Bowers M E, McCullough K M et al. Thy1-expressing neurons in the basolateral amygdala may mediate fear inhibition. J Neurosci 2013; 33(25): 10396-10404.
35. Sivertsen B, Holliday N, Madsen A N, Holst B. Functionally biased signalling properties of 7TM receptors—opportunities for drug development for the ghrelin receptor. Br J Pharmacol 2013; 170(7): 1349-1362.
36. Betley J N, Xu S, Cao Z F, Gong R, Magnus C J, Yu Y et al. Neurons for hunger and thirst transmit a negative-valence teaching signal. Nature 2015; 521(7551): 180-185.
37. Tolle V, Bassant M H, Zizzari P, Poindessous-Jazat F, Tomasetto C, Epelbaum J et al. Ultradian rhythmicity of ghrelin secretion in relation with GH, feeding behavior, and sleep-wake patterns in rats. Endocrinology 2002; 143(4): 1353-1361.
38. Carlini V P, Varas M M, Cragnolini A B, Schioth H B, Scimonelli T N, de Barioglio S R. Differential role of the hippocampus, amygdala, and dorsal raphe nucleus in regulating feeding, memory, and anxiety-like behavioral responses to ghrelin. Biochem Biophys Res Commun 2004; 313(3): 635-641.
39. Albarran-Zeckler R G, Brantley A F, Smith R G. Growth hormone secretagogue receptor (GHS-R1a) knockout mice exhibit improved spatial memory and deficits in contextual memory. Behav Brain Res 2012; 232(1): 13-19.
40. Brioni J D, Nagahara A H, McGaugh J L. Involvement of the amygdala GABAergic system in the modulation of memory storage. Brain Res 1989; 487(1): 105-112.
41. Wilensky A E, Schafe G E, LeDoux J E. Functional inactivation of the amygdala before but not after auditory fear conditioning prevents memory formation. J Neurosci 1999; 19(24): RC48.
42. Vaiva G, Thomas P, Ducrocq F, Fontaine M, Boss V, Devos P et al. Low posttrauma GABA plasma levels as a predictive factor in the development of acute posttraumatic stress disorder. Biol Psychiatry 2004; 55(3): 250-254.
43. Castellano C, Introini-Collison I B, McGaugh J L. Interaction of beta-endorphin and GABAergic drugs in the regulation of memory storage. Behav Neural Biol 1993; 60(2): 528 123-128.
44. Andero R, Brothers S P, Jovanovic T, Chen Y T, Salah-Uddin H, Cameron M et al. Amygdala-dependent fear is regulated by Oprl1 in mice and humans with PTSD. Sci Transl Med 2013; 5(188): 188ra173.
45. Holbrook T L, Galarneau M R, Dye J L, Quinn K, Dougherty A L. Morphine use after combat injury in Iraq and post-traumatic stress disorder. N Engl J Med 2010; 362(2): 110-117.
46. Jacks T, Smith R, Judith F, Schleim K, Frazier E, Chen H et al. MK-0677, a potent, novel, orally active growth hormone (GH) secretagogue: GH, insulin-like growth factor I, and other hormonal responses in beagles. Endocrinology 1996; 137(12): 5284-5289.
47. Lee G, Goosens K A. Sampling blood from the lateral tail vein of the rat. J Vis Exp 2015; (99): e52766.
48. Paxinos G, Watson C. The Rat Brain in Stereotaxic Coordinates—The New Coronal Set, Fifth Edition. Elsevier Academic Press: San Diego, 2005.
49. Myers R H. Classical and modern regression with applications. Duxbury Press: Boston, 1986.
50. Tibshirani R. Regression Shrinkage and Selection via the Lasso. J R Stat Soc: Ser B (Method) 1996; 58(1): 267-288.
51. Jacks T, Smith R, Judith F, Schleim K, Frazier E, Chen H et al. MK-0677, a potent, novel, orally active growth hormone (GH) secretagogue: GH, insulin-like growth factor I, and other hormonal responses in beagles. Endocrinology 1996; 137(12): 5284-5289.
52. Lee G, Goosens K A. Sampling blood from the lateral tail vein of the rat. J Vis Exp 2015; (99): e52766.
53. Paxinos G, Watson C. The Rat Brain in Stereotaxic Coordinates—The New Coronal Set, Fifth Edition. Elsevier Academic Press: San Diego, 2005.
54. Myers R H. Classical and modern regression with applications. Duxbury Press: Boston, 1986.
55. Tibshirani R. Regression Shrinkage and Selection via the Lasso. J R Stat Soc: Ser B (Method) 1996; 58(1): 267-288.
56. Hui G K, Figueroa I R, Poytress B S, Roozendaal B, McGaugh J L, Weinberger N M. Memory enhancement of classical fear conditioning by post-training injections of corticosterone in rats. Neurobiol Learn Mem 2004; 81(1): 67-74.
57. Cordero M I, Sandi C. A role for brain glucocorticoid receptors in contextual fear conditioning: dependence upon training intensity. Brain Res 1998; 786(1-2): 11-17.
58. Marin M F, Hupbach A, Maheu F S, Nader K, Lupien S J. Metyrapone administration reduces the strength of an emotional memory trace in a long-lasting manner. J Clin Endocrinol Metab 2011; 96(8): E1221-1227.
59. Tronson, N. C.; Taylor, J. R. (2007). "Molecular mechanisms of memory reconsolidation". Nature Reviews Neuroscience 8 (4): 262-275.
60. Bramham, C. R.; Messaoudi, E. (2005). "BDNF function in adult synaptic plasticity: The synaptic consolidation hypothesis". Progress in Neurobiology 76 (2): 99-125.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Articles such as "a," "an," and "the," as used herein, may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim or another portion of the description. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A method of treating a stress-sensitive psychiatric disease in a subject comprising administering to the subject a therapeutically effective amount of ghrelin or a functional ghrelin receptor (GHSR) agonist, within a memory consolidation period following a trauma exposure, wherein the stress-sensitive psychiatric disease is selected from the group consisting of: Post-traumatic Stress Disorder (PTSD), Depressive Disorder, Major Depressive Disorders, Bipolar Disorder, Acute Stress Disorder, Generalized Anxiety Disorder, Obsessive-Compulsive Disorder, Panic Disorders, and Trichotillomania, wherein the functional GHSR agonist is not adenosine.

2. The method of claim 1, wherein the ghrelin or the functional GHSR agonist is administered within 24 hours following the trauma exposure.

3. The method of claim 1, wherein the ghrelin or the functional GHSR agonist is administered within 48 hours following the trauma exposure.

4. The method of claim 1, wherein the ghrelin or the functional GHSR agonist is administered within 1 week following the trauma exposure.

5. The method of claim 1, wherein ghrelin is administered to the subject.

6. The method of claim 5, wherein the ghrelin is in the form of acyl-ghrelin.

7. The method of claim 1, wherein a functional GHSR agonist is administered to the subject.

8. The method of claim 7, wherein the functional GHSR agonist is selected from the group consisting of: alexamorelin, Anamorelin, Capromorelin, CP-464709, Cortistatin-14, Examorelin (hexarelin), Growth Hormone Releasing Peptide-1 (GHRP-1), Growth Hormone Releasing Peptide-3 (GHRP-3), Growth Hormone Releasing Peptide-4 (GHRP-4), Growth Hormone Releasing Peptide 5 (GHRP-5), Growth Hormone Releasing Peptide-6 (GHRP-6), Ibutamoren (MK-677), Ibutamoren mesylate (IBU), Ipamorelin, L-692585, LY-426410, LY-444711, Macimorelin, Pralmorelin, Relamorelin, SM-130,686, Tabimorelin, Ulimorelin, and combination thereof.

9. The method of claim 8, wherein the functional GHSR agonist is ibutamoren mesylate (IBU).

10. The method of claim 1, wherein the administering is via systemic administration, injection, or infusion directly into the BLA of the subject.

11. The method of claim 1, wherein the subject is unstressed.

12. The method of claim 1, wherein the subject is a human.

13. A method of treating a stress-sensitive psychiatric disease in a subject comprising administering to the subject a therapeutically effective amount of ghrelin or a functional ghrelin receptor (GHSR) agonist, within a memory re-consolidation period following re-activation of a memory of a previous trauma exposure,
wherein the stress-sensitive psychiatric disease is selected from the group consisting of: Post-traumatic Stress Disorder (PTSD), Depressive Disorder, Major Depressive Disorders, Bipolar Disorder, Acute Stress Disorder, Generalized Anxiety Disorder, Obsessive-Compulsive Disorder, Panic Disorders, and Trichotillomania, wherein the ghrelin agonist is not adenosine.

14. The method of claim 13, wherein the ghrelin or the functional GHSR agonist is administered within 24 hours following the re-activation of a memory of a previous trauma exposure.

15. The method of claim 13, wherein the ghrelin or the functional GHSR agonist is administered within 48 hours following the re-activation of a memory of a previous trauma exposure.

16. The method of claim 13, wherein the ghrelin or the functional GHSR agonist is administered within 1 week following the re-activation of a memory of a previous trauma exposure.

17. The method of claim 13, wherein ghrelin is administered to the subject.

18. The method of claim 17, wherein the ghrelin is in the form of acyl-ghrelin.

19. The method of claim 13, wherein a functional GHSR agonist is administered to the subject.

20. The method of claim 19, wherein the functional GHSR agonist is selected from the group consisting of: alexamorelin, Anamorelin, Capromorelin, CP-464709, Cortistatin-14, Examorelin (hexarelin), Growth Hormone Releasing Peptide-1 (GHRP-1), Growth Hormone Releasing Peptide-3 (GHRP-3), Growth Hormone Releasing Peptide-4

(GHRP-4), Growth Hormone Releasing Peptide 5 (GHRP-5), Growth Hormone Releasing Peptide-6 (GHRP-6), Ibutamoren (MK-677), Ibutamoren mesylate (IBU), Ipamorelin, L-692585, LY-426410, LY-444711, Macimorelin, Pralmorelin, Relamorelin, SM-130,686, Tabimorelin, Ulimorelin, and combination thereof.

21. The method of claim 20, wherein the functional GHSR agonist is ibutamoren mesylate (IBU).

22. The method of claim 13, comprising administering to the subject a therapeutically effective amount of ghrelin and a functional ghrelin receptor (GHSR) agonist.

23. The method of claim 13, wherein the administering is via systemic administration, injection, or infusion directly into the basolateral complex of the amygdala (BLA) of the subject.

24. The method of claim 13, wherein the subject is unstressed.

25. The method of claim 13, wherein the subject is a human.

26. The method of claim 13, wherein the memory of the previous trauma exposure is a long-term memory.

27. A method of treating a stress-sensitive psychiatric disease in a subject who has been exposed to chronic stress, comprising:
    (a) upregulating the endogenous level of ghrelin receptors (GHSRs) in the subject, the upregulating comprising administering to the subject a therapeutically effective amount of a ghrelin antagonist or a GHSR antagonist; and
    (b) administering to the subject a therapeutically effective amount of ghrelin or a functional GHSR agonist, within a memory consolidation period following a trauma exposure, wherein the stress-sensitive psychiatric disease is selected from the group consisting of: Post-traumatic Stress Disorder (PTSD), Depressive Disorder, Major Depressive Disorders, Bipolar Disorder, Acute Stress Disorder, Generalized Anxiety Disorder, Obsessive-Compulsive Disorder, Panic Disorders, and Trichotillomania.

28. The method of claim 27, wherein the ghrelin antagonist is an anti-ghrelin vaccine.

29. The method of claim 27, wherein the ghrelin antagonist inhibits ghrelin acylation.

30. The method of claim 27, wherein the ghrelin or the functional GHSR agonist is administered within 24 hours following the trauma exposure.

31. The method of claim 27, wherein the ghrelin or the functional GHSR agonist is administered within 48 hours following the trauma exposure.

32. The method of claim 27, wherein the ghrelin or the functional GHSR agonist is administered within 1 week following the trauma exposure.

33. The method of claim 27, wherein the functional GHSR agonist is selected from the group consisting of: Adenosine, alexamorelin, Anamorelin, Capromorelin, CP-464709, Cortistatin-14, Examorelin (hexarelin), Growth Hormone Releasing Peptide-1 (GHRP-1), Growth Hormone Releasing Peptide-3 (GHRP-3), Growth Hormone Releasing Peptide-4 (GHRP-4), Growth Hormone Releasing Peptide-5 (GHRP-5), Growth Hormone Releasing Peptide-6 (GHRP-6), Ibutamoren (MK-677), Ibutamoren mesylate (IBU), Ipamorelin, L-692585, LY-426410, LY-444711, Macimorelin, Pralmorelin, Relamorelin, SM-130,686, Tabimorelin, Ulimorelin, and combination thereof.

34. The method of claim 27, wherein the step of upregulating further comprises measuring the endogenous ghrelin levels in the subject.

35. The method of claim 27, wherein the subject who have been exposed to chronic stress has elevated endogenous ghrelin levels compared to that of a control.

36. The method of claim 35, wherein the control is a subject not exposed to chronic stress.

37. The method of claim 27, wherein the subject is a human.

38. The method of claim 29, wherein the ghrelin antagonist inhibits ghrelin O-acyltransferase (GOAT).

39. The method of claim 38, wherein the ghrelin antagonist is an anti-GOAT vaccine.

* * * * *